US011459396B2

United States Patent
Ober et al.

(10) Patent No.: US 11,459,396 B2
(45) Date of Patent: Oct. 4, 2022

(54) FUSION PROTEINS (SELDEGS) FOR SELECTIVELY DEPLETING ANTIGEN-SPECIFIC ANTIBODIES AND METHODS OF USE THEREOF

(71) Applicant: THE TEXAS A&M UNIVERSITY SYSTEM, College Station, TX (US)

(72) Inventors: Elizabeth Sally Ward Ober, College Station, TX (US); Venkata Siva Charan Devanaboyina, Fremont, CA (US); Raimund Johannes Ober, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 247 days.

(21) Appl. No.: 16/465,975

(22) PCT Filed: Dec. 1, 2017

(86) PCT No.: PCT/US2017/064186
§ 371 (c)(1),
(2) Date: May 31, 2019

(87) PCT Pub. No.: WO2018/102668
PCT Pub. Date: Jun. 7, 2018

(65) Prior Publication Data
US 2020/0031948 A1    Jan. 30, 2020

Related U.S. Application Data

(60) Provisional application No. 62/429,367, filed on Dec. 2, 2016.

(51) Int. Cl.
| | | |
|---|---|---|
| C07K 16/28 | (2006.01) | |
| A61K 38/00 | (2006.01) | |
| C07K 14/71 | (2006.01) | |
| A61K 51/10 | (2006.01) | |

(52) U.S. Cl.
CPC .......... *C07K 16/2881* (2013.01); *C07K 14/71* (2013.01); *A61K 38/00* (2013.01); *A61K 51/1027* (2013.01); *C07K 2317/52* (2013.01); *C07K 2317/569* (2013.01); *C07K 2317/71* (2013.01); *C07K 2317/72* (2013.01); *C07K 2317/76* (2013.01); *C07K 2317/77* (2013.01); *C07K 2317/92* (2013.01); *C07K 2319/30* (2013.01)

(58) Field of Classification Search
CPC ................ C07K 16/2881; C07K 14/71; C07K 2317/52; C07K 2317/569; C07K 2317/71; C07K 2317/72; C07K 2317/76; C07K 2317/77; C07K 2317/92; C07K 2319/30; A61K 38/00

See application file for complete search history.

(56) References Cited

U.S. PATENT DOCUMENTS

| | | |
|---|---|---|
| 2005/0249723 A1 | 11/2005 | Lazar |
| 2006/0235208 A1 | 10/2006 | Lazar et al. |
| 2016/0060358 A1 | 3/2016 | Hay |
| 2017/0334962 A1 | 11/2017 | Ober et al. |

FOREIGN PATENT DOCUMENTS

| | | |
|---|---|---|
| WO | WO 02/16414 | 2/2002 |
| WO | 2002044329 A2 | 6/2002 |
| WO | 2006130834 A2 | 12/2006 |
| WO | WO 2012/142515 | 10/2012 |
| WO | 20120150319 A1 | 11/2012 |
| WO | 20150100299 A1 | 7/2015 |

OTHER PUBLICATIONS

Devanaboyina S, et al. (May 31, 2017). Nature Communications. 6 pages plus 8 supplemental pages. (DOI: 10.1038/ncomms15314).*
Sun W, et al. (Mar. 2021). Molecular Therapy vol. 29(3). 12 pages plus 6 supplemental pages.(https://doi.org/10.1016/j.ymthe.2020.11.017).*
Khare P, et al. (2021) 13(1). 6 pages, (https://doi.org/10.1080/19420862.2021.1976705).*
International Search Report and Written Opinion dated Mar. 15, 2018 for corresponding International Application No. PCT/US2017/064186.
Battaini, F. et al. 2004 "Antibody response after vaccination with antigen-pulsed dendritic cells", International Journal of Biological Markers. vol. 19, No. 3, pp. 213-220.
Challa, D. et al 2016 "Antigen dynamics govern the induction ofCD4+ T cell tolerance during autoimmunity", Journal of Autoimmunity. vol. 72, pp. 84-94, Published Online: May 25, 2016.
Ha, J-H. et al. 2016 "Immunoglobulin Fe Heterodimer Platform Technology: From Design to Applications in Therapeutic Antibodies and Proteins", Frontiers in Immunology. vol. 7, Art. 394, pp. 1-16, Published: Oct. 6, 2016.
Mann, J. et al. 2012 "Transferrin conjugation confers mucosa! molecular targeting to a model HIV-1 trimeric gpl40 vaccine antigen", Journal of Controlled Release. vol. 158, pp. 240-249.
Neves, A. et al. 2014 "Imaging cell death", Journal of Nuclear Medicine. vol. 55, No. 1, pp. 1-4.

(Continued)

*Primary Examiner* — Robert S Landsman
(74) *Attorney, Agent, or Firm* — Edell, Shapiro & Finnan, LLC

(57) ABSTRACT

The present disclosure includes a fusion protein, called a "Seldeg", including a targeting component that specifically binds to a cell surface receptor or other cell surface molecule at near-neutral pH, and an antigen component fused directly or indirectly to the targeting component. The antigen component is configured to specifically bind a target antigen-specific antibody. The present disclosure also includes a method of depleting a target antigen-specific antibody from a patient by administering to the patient a Seldeg having an antigen component configured to specifically bind the target antigen-specific antibody.

20 Claims, 19 Drawing Sheets
Specification includes a Sequence Listing.

(56) References Cited

OTHER PUBLICATIONS

Saito, Y. et al. 1995 "Vector-mediated delivery of 125I-labeled b-amyloid peptide Abl-40 through the blood-brain barrier and binding to Alzheimer disease amyloid of the Abl-40/vector complex", Proc. Natl. Acad. Sci. USA. Vol. 92, pp. 10227-10231.

Wang, Y. et al. 2016 "Nanobody-derived nano biotechnology tool kits for diverse biomedical and biotechnology applications" International Journal of Nanomedicine. vol. 11, pp. 3287-3303. Published: Jul. 21, 2016.

Ward, E. et al. 2015 "Targeting FcRn for the modulation of antibody dynamics", Molecular Immunology. vol. 67, pp. 131-141.

Challa, D. K. et al. "Autoantibody depletion ameliorates disease in murine experimental autoimmune encephalomyelitis" *mAbs*, Sep./Oct. 2013, pp. 655-659, vol. 5, Issue 5.

* cited by examiner

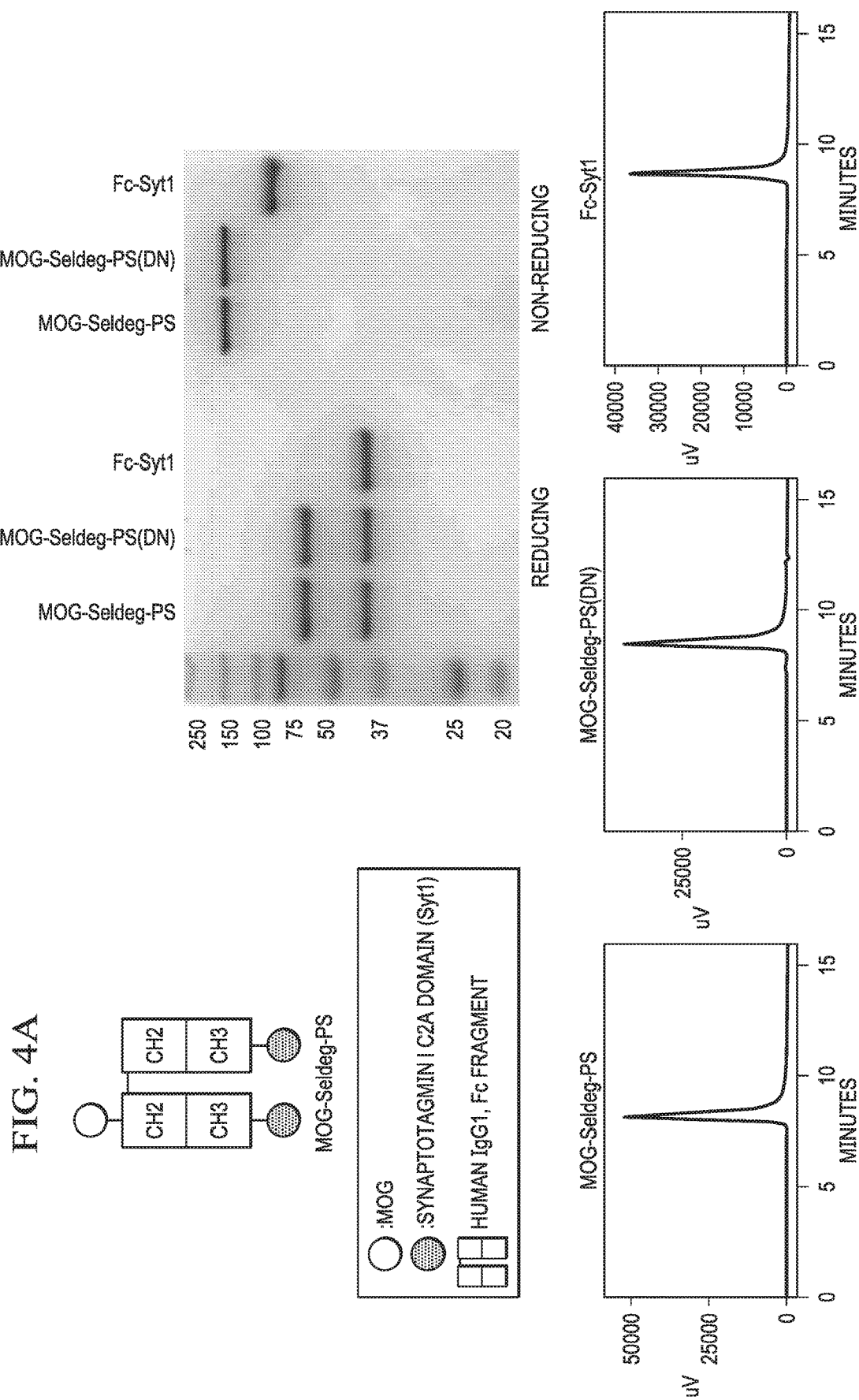

FUSION PROTEINS (SELDEGS) FOR SELECTIVELY DEPLETING ANTIGEN-SPECIFIC ANTIBODIES AND METHODS OF USE THEREOF

TECHNICAL FIELD

This disclosure relates to engineered proteins, and more specifically, to fusion proteins that selectively deplete target antigen-specific antibodies from the body ("Seldegs").

BACKGROUND

Antibodies are Y-shaped proteins present in blood and other body fluids of the human body and the bodies of mammals. Antibodies are a critical component of the body's immune system. They function by recognizing a unique part of a foreign target, called the antigen. An antibody is able to selectively recognize and trigger an immune response to an antigen through its two antigen-binding sites. Each antigen-binding site is at the end of each upper tip of the antibody's Y-shape. The target antigen may bind one or both antigen-binding sites. The base of an antibody's Y-shape is called an Fc fragment. When an antibody binds to its target, the Fc region can bring about target clearance through antibody effector functions. Such responses can include cellular processes to destroy the antigen. In certain autoimmune diseases and other illnesses, pathogenic antibodies may be created that target self-antigens in the body, contributing to pathogenesis. An antibody may be in either of two physical forms, a soluble form that is secreted from the cell and is free in the blood plasma, or a membrane-bound form that is attached to the outer-membrane of a B cell. The secreted antibodies cause pathology in diseases involving autoreactive antibodies. They can also contribute to transplant rejection or the elimination of protein-based therapeutics.

Due to their ability to bind specifically to target molecules, antibodies can be used to treat diseases such as cancer and autoimmunity. They also have applications in the detection of tumors during whole body imaging using, for example, radiolabeled antibodies in positron emission tomography (PET). However, their relatively long in vivo persistence can lead to high background in non-tumor tissue, resulting in poor contrast for tumor imaging and undesirable off-target effects.

SUMMARY

The present disclosure includes fusion proteins, herein referred to as "Seldegs", that are configured to allow selective clearance of antigen-specific antibodies. A Seldeg includes a targeting component that is configured to specifically bind to a cell surface receptor or other cell surface molecule, and an antigen component that is configured to specifically bind to an antigen-specific antibody or a variant thereof.

The targeting component of the Seldeg includes a protein or a protein fragment that is configured to specifically bind to a cell surface receptor or other cell surface molecule. The antigen component of the Seldeg includes one molecule of an antigen or antigen fragment or antigen mimetic configured to specifically bind a target antigen-specific antibody. The antigen component is fused directly or indirectly to the targeting component.

The present disclosure also includes a method of depleting a target antigen-specific antibody from a patient by administering to the patient a Seldeg in an amount sufficient to remove at least 50% of the target antigen-specific antibody from the circulation or a target tissue in the patient.

The above Seldegs and methods may further include the following details, which may be combined with one another unless clearly mutually exclusive: i) the targeting component can bind to the cell surface receptor or cell surface molecule with a dissociation constant of less than 10 μM at near-neutral pH, ii) near-neutral pH may be greater than 6.8 and less than 7.5; iii) the Seldeg can comprise at least a first targeting component and a second targeting component, wherein the protein or protein fragment of the first targeting component is configured to bind to a different cell surface receptor or a different cell surface molecule than the protein or protein fragment of the second targeting component; iv) the targeting component may include a heterodimer of two immunoglobulin Fc fragments in which one immunoglobulin Fc fragment of the heterodimer is fused to the antigen component and the other immunoglobulin Fc fragment may not be; v) the immunoglobulin Fc fragment may have substantially reduced binding or no detectable binding to Fc gamma receptors; vi) the immunoglobulin Fc fragments can be derived from an immunoglobulin class or isotype that does not bind to Fc gamma receptors or complement; vii) the immunoglobulin Fc fragments can be configured to bind to Fc gamma receptors and complement; viii) at least one of the immunoglobulin Fc fragments can be modified to have a higher binding affinity for FcRn at near-neutral pH than an unmodified immunoglobulin Fc fragment; ix) the antigen component may be fused to one immunoglobulin Fc fragment at an N-terminus or a C-terminus of a hinge-$CH_2$—CH domain of the immunoglobulin Fc fragment; x) the immunoglobulin Fc fragments may be modified to have no binding affinity for Fc gamma receptors and/or complement (C1q), or lower binding affinity for Fc gamma receptors and/or complement (C1q) than unmodified immunoglobulin Fc fragments; xi) the targeting component may include one or more antibody variable regions or fragments thereof that are configured to specifically bind to the cell surface receptor or the cell surface molecule; xii) the antibody variable region or fragment thereof may include at least one nanobody, xiii) the nanobody may be a nanobody multimer in which one nanobody is fused to the antigen component and all other nanobodies in the nanobody multimer may not be; xiv) the targeting component may be configured to dissociate from the cell surface receptor or cell surface molecule following entry into an endosome of a complex comprising the Seldeg and the cell surface receptor or cell surface molecule; xv) the antigen component may be fused to an N-terminal location or a C-terminal location on the targeting component; xvi) the antigen component may be fused to a non-terminal location on the targeting component; xvii) the antigen component may be fused to the targeting component via a chemical reaction, through a linker, or during formation of a single combined antigen component-targeting component fusion protein; xviii) the targeting component can be one or more albumin molecules, albumin fragments or mutated albumin variants that are configured to specifically bind to a FcRn; xix) the targeting component can include one or more antibody variable domains or nanobodies that are configured to bind to a transferrin receptor; xx) the targeting component can include one or more protein molecules or protein domains configured to bind to a transferrin receptor; xxi) the targeting component can include one or more protein molecules or protein domains configured to bind to a phosphatidylserine; xxii) the targeting protein component can include one or more antibody variable domains or nanobodies configured to bind to a phosphatidylserine; xxiii) the one or more protein molecules or protein domains can be configured to bind the phosphatidylserine via a calcium-dependent mechanism; xxiv) the targeting component can include a C2A domain of synaptotagmin 1; xxv) the Seldeg can include at least a first antigen component and a second antigen component, wherein the one molecule of the antigen, antigen fragment or antigen mimetic of the first antigen component is different to the one molecule of the antigen molecule, antigen fragment or antigen mimetic of the second antigen component; xxvi) the Seldeg can include at least a first antigen component and a second antigen component, wherein the one molecule of the antigen, antigen fragment or antigen mimetic of the first antigen component is the same as the one molecule of the antigen molecule, antigen fragment or antigen mimetic of the second antigen component; xxvii) the method may include administering an amount sufficient of Seldeg to remove at least 50% of the target antigen-specific antibody from the circulation or the target tissue in the patient within five hours of administration; xxviii) the method may include administering a Seldeg having a targeting component that includes a protein or protein fragment configured to bind to the cell surface receptor or other cell surface molecule with a dissociation constant of less than 10 μM at near neutral pH; xxix) the amount sufficient of Seldeg administered may be an amount at least equimolar to the amount of target antigen-specific antibody to be depleted, xxx) the method may include administering the Seldeg in an amount sufficient to remove at least 90% of the target antigen-specific antibody from the circulation or target tissue in the patient within two hours of administration; xxxi) the Seldeg may be administered in an amount sufficient to remove at least 50% of the target antigen-specific antibody from the circulation or target tissue in the patient within one hour of administration; xxxii) the Seldeg may be re-administered whenever 50% of patients are expected to have regenerated a threshold amount of target antigen-specific antibody in the circulation or target tissue; xxxiii) the Seldeg may remove less than 10% of non-target antibodies in the circulation or in the tissue targeted by the target antigen-specific antibody; xxxiv) the Seldeg may remove an amount of non-targeted antibodies in the circulation or in the target tissue of the patient that does not cause a clinically adverse effect in the patient; xxxv) the Seldeg may remove less than 1% of non-target antibodies in the circulation or in a tissue targeted by the target antigen-specific antibody; xxxvi) the Seldeg may cause degradation of the target antigen-specific antibody by a cell expressing the cell surface receptor or cell surface molecule; xxxvii) the Seldeg may be administered to a patient with an autoimmune disease and the target antigen-specific antibody may specifically bind to an autoantigen; xxxviii) the Seldeg may be administered to a patient receiving a transplanted organ and the target antigen-specific antibody may specifically bind to an antigen on the transplanted organ; xxxix) the Seldeg may be administered to increase contrast during tumor imaging and the target antigen-specific antibody may specifically bind to a tumor antigen; xl) the Seldeg may be administered to a patient who has received a biologic and the target antigen-specific antibody may be the biologic; xli) the Seldeg may be administered to a patient prior to the delivery of a therapeutic agent, if the patient has antibodies specific for the therapeutic agent, and the Seldeg is configured to target the antibodies specific for the therapeutic agent; xlii) the Seldeg may be administered to provide a PET image contrast agent; xliii) the target antigen-specific antibody may be an anti-MOO antibody; xliv) the target antigen-specific antibody may be an anti-HER2 antibody; xlv) the Seldeg may include proteins having amino acid sequences of at least one of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34, or a homolog thereof; xlvi) the Seldeg may include a heterodimer of proteins having amino acid sequences of SEQ ID NO: 2 plus SEQ ID NO: 6, SEQ ID NO: 4 plus SEQ ID NO: 6, SEQ ID NO: 8 plus SEQ ID NO: 10, SEQ ID NO: 12 plus SEQ ID NO: 14, SEQ ID NO: 16 plus SEQ ID NO: 18 plus SEQ ID NO: 20, SEQ ID NO: 20 plus SEQ ID NO: 22 plus SEQ ID NO: 24, SEQ ID NO: 26 plus SEQ ID NO: 28, SEQ ID NO: 30 plus SEQ ID NO: 6, SEQ ID NO: 32 plus SEQ ID NO: 6, or SEQ ID NO: 34 plus SEQ ID NO: 6, or homologs thereof.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which:

FIG. 1 is a schematic diagram of selected cellular events that lead to the degradation of antigen-specific antibodies in the presence of Seldegs;

FIG. 2A is a schematic diagram of a Seldeg including an antigen fused to a N-terminal location of an Fc fragment, FIG. 2B is a schematic diagram of a Seldeg including an antigen fused to a C-terminal location of an Fc fragment;

FIG. 2C is a schematic diagram of a Seldeg including an antigen fused to a non-terminal location of an Fc fragment;

FIG. 2D is a schematic diagram of a Seldeg including an antigen fused to a terminal location of a protein or protein fragment that binds to a cell surface receptor or cell surface molecule;

FIG. 2E is a schematic diagram of a Seldeg including an antigen fused to a non-terminal location of a protein or protein fragment that binds to a cell surface receptor or cell surface molecule;

FIG. 2F is a schematic diagram of a Seldeg including an antigen fused to a N-terminal location of an Fc fragment and protein or protein fragments that bind to a cell surface protein or cell surface receptor fused to the C-termini of the Fc fragment;

FIG. 2G is a schematic diagram of a Seldeg including an antigen fused to a C-terminal location of an Fc fragment and protein or protein fragments that bind to a cell surface protein or cell surface receptor fused to the N-termini of the Fc fragment, FIG. 2H is a schematic diagram of a Seldeg including an antigen fused to a C-terminal location of an antibody that binds to a cell surface protein or cell surface receptor, FIG. 2I is a schematic diagram of a Seldeg including an antigen fused to a C-terminal location of an Fc fragment and scFv fragments that bind to a cell surface protein or cell surface receptor fused to the N-termini of the Fc fragment.

FIG. 2J is a schematic diagram of a Seldeg including an antigen fused to a N-terminal location of an Fc fragment and scFv fragments that bind to a cell surface protein or cell surface receptor fused to the C-termini of the Fc fragment;

FIG. 2K is a schematic diagram of a Seldeg including two different antigens fused to the N-terminal locations of an Fc fragment;

FIG. 2L is a schematic diagram of a Seldeg comprising two different antigens fused to the N-terminal locations of an Fc fragment and protein or protein fragments that bind to a cell surface protein or cell surface receptor fused to the C-termini of the Fc fragment;

FIG. 4A shows in the upper left panel a schematic diagram of an exemplary Seldeg referred to as MOG-Seldeg-PS comprising an antigen fused to targeting protein (C2A domain of synaptotagmin 1, Syt1) that binds to phosphatidylserine (PS); in the upper right panel FIG. 4A shows exemplary SDS-PAGE gels (reducing and non-reducing conditions) of recombinant proteins of MOG-Seldeg-PS, MOG-Seldeg-PS(DN) with mutations that substantially reduce binding to PS, and Fc-Syt1 that has no antigen (MOG) attached; in the lower panel, FIG. 4A shows exemplary HPLC profiles of the recombinant proteins that are shown in the upper right FIG. 4A, MOG-Seldeg-PS, MOG-Seldeg-PS(DN) and Fc-Syt1;

FIG. 4B shows additional graphs reporting exemplary normalized blood and body count versus time, showing clearance of an antigen-specific antibody by an exemplary PS-targeting Seldeg;

FIG. 5A shows graphs reporting exemplary data showing the accumulation of antigen-specific antibodies in cells in the presence of exemplary FcRn-targeting Seldegs and control proteins;

FIG. 5B is an exemplary series of microscopic images of an exemplary FcRn-targeting Seldeg and control protein in the presence of target antigen-specific antibodies, with microscopic images of representative endosomes cropped, expanded, and presented in the top right-corner insets;

FIG. 5C is another series of exemplary microscopic images of an exemplary FcRn-targeting Seldeg and control protein in the presence of target antigen-specific antibodies, with microscopic images of representative endosomes cropped, expanded, and presented in the top right-corner insets;

FIG. 6A is another series of exemplary microscopic images of an exemplary FcRn-targeting Seldeg and control protein in the presence of target antigen-specific antibodies, with microscopic images of representative lysosomes cropped, expanded, and presented in the top right-corner insets;

FIG. 6B is another series of exemplary microscopic images of exemplary FcRn-targeting Seldegs in the presence of antigen-specific antibodies that do not recognize the antigen that is being targeted by the Seldeg, with microscopic images of representative lysosomes cropped, expanded, and presented in the top right-corner insets;

FIG. 7 shows graphs reporting exemplary data showing the accumulation of antigen-specific antibodies in cells in the presence of exemplary PS-targeting Seldegs and control proteins;

FIG. 8 is a schematic diagram of an exemplary Seldeg including an antigen fused to targeting protein (antibody) that binds to the transferrin receptor (TfR), HPLC profiles of the recombinant proteins are shown, including an analysis of the targeting protein (antibody) without antigen (MOG) attached;

FIG. 9 is a graph reporting exemplary data showing the accumulation of antigen-specific antibodies in cells in the presence of an exemplary TfR-targeting Seldeg and control protein;

FIG. 10A is an exemplary series of positron emission tomography (PET) analyses of tumors in mice following delivery of radiolabeled HER2-specific antibody and treatment with an exemplary FcRn-targeting Seldeg, control protein or vehicle control.

FIG. 10B shows a graph reporting contrast measures for tumor:thoracic regions of tumor-bearing mice following delivery of radiolabeled HER2-specific antibody and treatment with an exemplary FcRn-targeting Seldeg, control protein or vehicle control.

DETAILED DESCRIPTION

This disclosure relates to engineered proteins, and more specifically, to Seldegs, which are fusion proteins that are configured to selectively target antigen-specific antibodies for depletion from the body. Seldegs cause the selective degradation of the targeted antigen-specific antibodies by binding to the antigen-specific antibodies and directing them to late endosomes or lysosomes, which contain degradative enzymes. A Seldeg is a fusion protein or molecule that includes at least a targeting component and an antigen component. The targeting component includes a protein or protein fragment or other molecule that is configured to bind to a cell surface receptor or other cell surface molecule. The antigen component includes one molecule of an antigen, antigen fragment or antigen mimetic that is recognized by the targeted antigen-specific antibody.

Upon binding of the antigen-specific antibody to the antigen component, a complex is formed comprising the Seldeg and the antigen-specific antibody. The complex is also configured to bind to the cell surface receptor or other cell surface molecule, allowing cellular internalization of a complex that includes the Seldeg, the antigen-specific antibody, and the targeted cell surface receptor or other cell surface molecule (see FIG. 1). The targeted cell surface receptor or cell surface molecule may dissociate from the complex upon entry into the endosomes, due to acidic pH, low calcium concentrations and/or other conditions that distinguish the endosomal environment from the extracellular environment. Internalization into endosomes and lysosomal entry results in the selective degradation of the complex.

Figure 1:
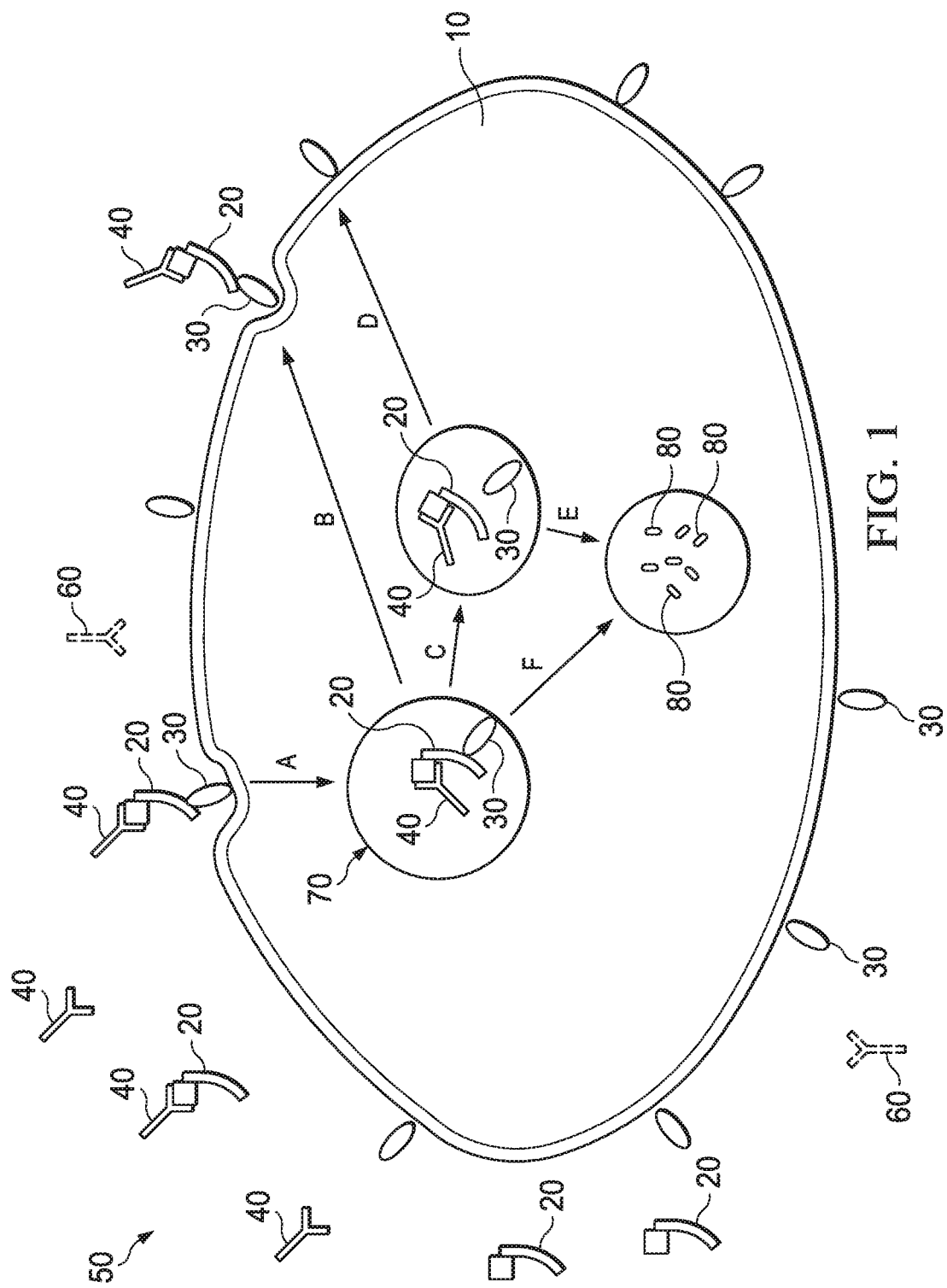

The term "antigen-specific antibody" as used herein refers to an antibody or antibody that binds to a particular antigen, antigen fragment or antigen mimetic.

The term "antigen fragment" as used herein refers to a part of the antigen that can be recognized by the antigen-specific antibody.

The term "antigen mimetic" as used herein refers to a protein, protein fragment, peptide or other molecule that has the same overall shape and properties as the part of the antigen that is recognized by an antigen-specific antibody.

The term "cell surface molecule" as used herein refers to a protein or other biological molecule (e.g. phospholipid, carbohydrate) that is exposed on the plasma membrane of a cell.

Seldegs may include an antigen fused to an Fc fragment of an IgG antibody (herein also referred to as "immunoglobulin Fc fragment"), an FcRn-specific nanobody-antigen fusion molecule, an FcRn-specific antibody that binds to FcRn through its variable region fused to an antigen, an albumin-antigen fusion protein, a PS-binding protein, a TfR-specific antibody or other protein, protein fragment or other molecule that is configured to bind to a cell surface receptor or other cell surface molecule identifiable by skilled persons upon reading of the present disclosure.

Examples of Seldegs described herein include targeting components that are configured to bind to cell surface molecules such as human FcRn, exposed phosphatidylserine (PS) or the transferrin receptor (TfR) with affinities (dissociation constants) of less than 10 μM at near neutral pH.

FcRn and TfR are proteins, and PS is a phospholipid, that may be found on the surface and within multiple different cell types within the body. This invention is not limited to targeting these receptors or cell surface molecules, and many other targets could be envisaged such as the low density lipoprotein receptor, high density lipoprotein receptor, asialoglycoprotein receptor, inhibitory Fc gamma receptors, T cell receptor, B cell receptor, G-protein coupled receptors, insulin receptor, glucagon receptors, galactose receptors, mannose receptors, VEGF receptors, mannose receptors among others identifiable by those skilled in the art. Other targets can be identified in, for example, the following publications or databases. Cell surface receptor protein atlas (Bausch-Fluck, D., Hofmann, A., Bock, T., Frei, A. P., Cerciello, F., Jacobs, A., Moest, H., Omasits, U., Gundry, R. L., Yoon, C., Schiess, R., Schmidt, A., Mirkowska, P., Härtlova, A., Van Eyk, J. E., Bourquin, J P., Aebersold, R., Boheler, K. R., Zandstra, P., Wollscheid, B. (2015) A mass spectrometric-derived cell surface protein atlas. PLoS One 10: e0121314), and the Human protein atlas (https://www.proteinatlas.org/humanproteome/secretome).

The targeting component can bind the cell surface receptor or other cell surface molecule with an affinity (dissociation constant) of less than 10 μM at near-neutral pH.

Accordingly, the targeting component of a Seldeg can include any type of molecule that is configured to specifically bind to a cell surface receptor or other cell surface molecule. Such molecules can include proteins, protein fragments, polynucleotides such as ribonucleic acids or deoxyribonucleic acids, polypeptides, polysaccharides, lipids, amino acids, peptide, sugars and/or other small or large molecules and/or polymers identifiable by skilled persons upon reading of the present disclosure. For example, the targeting component of a Seldeg can include a polynucleotide that is a ligand for a cellular receptor.

The Seldeg can comprise at least a first targeting component and a second targeting component, wherein the protein or protein fragment of the first targeting component is configured to bind to a different cell surface receptor or a different cell surface molecule than the protein or protein fragment of the second targeting component.

As shown in FIG. 1, a Seldeg 20 may reversibly bind to cell surface receptor or other molecule 30 on the surface of a cell 10. A target antigen-specific antibody 40, present in extracellular space 50, may reversibly bind to Seldeg 20. This binding typically occurs at near-neutral pH, such as at a pH greater than 6.8 and less than 7.5, because that is the typical pH of extracellular space 50. Non-target antibodies 60 do not bind to Seldeg 20, or bind with such low affinities that any binding is non-specific. Cell surface receptor or molecule 30 with attached Seldeg 20 and target antigen-specific antibody 40 are internalized into the cell 10 through receptor-mediated uptake into endosome 70 via pathway A. The receptor or other molecule can be recycled back to the surface of the cell. Accordingly, on pathway 8, receptor or molecule 30 with attached Seldeg 20 and target antigen-specific antibody 40 are cycled back to the surface of cell 10. Target antigen-specific antibody 40 may then be released and may reattach from Seldeg 20 to the same or another Seldeg, or it may remain attached. Similarly, Seldeg 20 may then be released from receptor or molecule 30 and may reattach to the same or another cell surface receptor or molecule. For some Seldegs, the complex of Seldeg 20 and antibody 40 may dissociate from the receptor or other molecule 30 in the early or late endosome due to the acidic pH or low $Ca^{2+}$ concentrations in this compartment (pathway C). Accordingly, in pathway D, receptor or cell surface molecule may recycle back to the cell surface whereas the Seldeg 20 bound to antibody 40 enters the lysosomes and is degraded into fragments 80 in pathway E. For some Seldegs, at some point following internalization into cell 10, receptor or molecule 30 with attached Seldeg 20 and target antigen-specific antibody 40 enters the late endosomal/lysosomal in pathway F, in which at least target antigen-specific antibody 40 is degraded into fragments 80. This entry into lysosomes is expected to be increased if Seldeg 20 cross-links receptor or molecule 30 into dimers or higher order aggregates.

Through this mechanism of selective depletion, Seldegs target and selectively deplete antigen-specific antibodies from the body without adversely affecting the levels of antibodies of non-targeted specificities.

In particular, Seldegs as described herein can target and selectively deplete antigen-specific antibodies from the body without having an adverse clinical effect in the patient due to the depletion of antibodies of non-targeted specificities Such adverse clinical effects include, for example, immunosuppression, and symptoms thereof, such as pinkeye, bronchitis, ear infections, sinus infections, cold, diarrhea, pneumonia, yeast infection, meningitis, skin infections, and other opportunistic infections, particularly opportunistic infection normally controlled through antibody mediated immune responses; and blood disorders, such as low platelet counts or anemia, and hypogammaglobulinemia and symptoms thereof, such as abdominal pain, bloating, nausea, vomiting, diarrhea, or weight loss.

In general, Seldegs according to this disclosure are configured to specifically bind a cell surface receptor/molecule at near-neutral pH via a targeting component and also specifically bind to an antigen-specific antibody at near-neutral pH via an antigen component that is fused directly or indirectly to the targeting component. The term "specifically bind" as used herein refers to a detectable selective intermolecular interaction between the targeting component and the cell surface receptor/molecule, or between the antigen component and the antigen-specific antibody. For example, to specifically bind, the antigen needs to show a detectable interaction with the antibodies that are being targeted, whilst not showing a detectable interaction with other antibodies. Techniques for detecting specific binding are known within the art, such as ELISA, surface plasmon resonance analyses and other methods identifiable by skilled persons.

Accordingly, Seldegs allow at least a portion of the antigen-specific antibody in the circulation of a patient to be internalized into cells that express the targeted cell surface receptor or targeted other cell surface molecule and thereafter intracellularly degraded.

Seldegs according to this disclosure may avoid immune responses by containing one copy, otherwise referred herein as "one molecule", of each type of antigen, antigen fragment or antigen mimetic, per Seldeg, which in combination with the insertion of mutations to reduce or eliminate Fc gamma receptor binding and/or complement binding, is expected to decrease antibody cross-linking and the formation of potentially inflammatory immune complexes. In particular, at least 99% of Seldegs, at least 99.5% of Seldegs., or at least 99.9% of Seldegs may contain only one copy of antigen, antigen fragment, or antigen mimetic per Seldeg at near-neutral pH. Other Seldegs according to the present disclosure can contain more than one molecule of an antigen, antigen fragment, or antigen mimetic. The bivalent nature of the antibodies that are bound by Seldegs that contain one molecule of antigen per Seldeg molecule may result in complexes of two Seldeg molecules per antibody, which through target receptor dimerization is expected to increase the efficiency of lysosomal delivery of Seldeg-antibody complexes.

Seldegs can include at least a first antigen component and a second antigen component, wherein the one molecule of the antigen, antigen fragment or antigen mimetic of the first antigen component is different to the one molecule of the antigen molecule, antigen fragment or antigen mimetic of the second antigen component. Accordingly, Seldegs comprising at least a first antigen component and a second antigen component allow clearance of antigen-specific antibodies of more than one specificity.

Seldegs can include at least a first antigen component and a second antigen component, wherein the one molecule of the antigen, antigen fragment or antigen mimetic of the first antigen component is the same as the one molecule of the antigen molecule, antigen fragment or antigen mimetic of the second antigen component.

Accordingly, Seldegs can include, for example, one or more antigen components fused to a C-terminus and/or an N-terminus of a targeting component, wherein the one molecule of the antigen, antigen fragment or antigen mimetic antigen components of the respective antigen components can be the same or different.

In addition, Seldegs may contain human or humanized proteins or protein fragments to avoid or decrease the possibility of an immune reaction to the Seldeg when administered to a human. The antigen, antigen fragment, or antigen mimetic of the antigen component is preferably a human protein or protein fragment for administration of the Seldeg to a human. The targeting component is also preferably a human protein or protein fragment, such as a human antibody fragment or human albumin or albumin fragment, or a humanized antibody or humanized antibody fragment for administration of the Seldeg to a human. If a Seldeg is developed for use in a non-human animal, then proteins or protein fragments derived from or engineered to be immunologically compatible with that animal may be used instead.

Figure 2A:
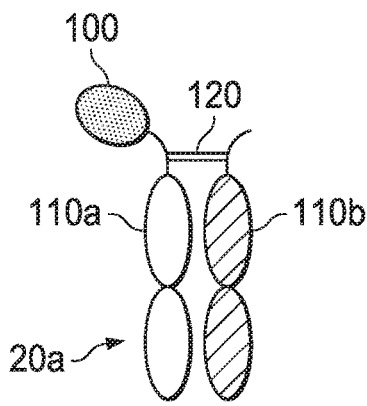
FIG. 2M is a schematic diagram of a Seldeg comprising two antigen molecules fused to the N-terminal locations of an Fc fragment.
FIG. 2N is a schematic diagram of a Seldeg comprising two antigen molecules fused to the N-terminal locations of an Fc fragment and protein or protein fragments that bind to a cell surface protein or cell surface receptor fused to the C-termini of the Fc fragment.

FIG. 2A is a schematic representation of the activity of a Seldeg 20a including antigen 100 fused to a targeting component having the Fc fragment of IgG 110. As understood by persons skilled in the art, the Fc fragment of an IgG is all of the lower base of the antibody's Y-shape, which is the sulfhydryl-bridged hinge region and the CH2 and CH3 domains. Seldegs can have an Fc fragment that does not have the hinge region, or the hinge region does not have sulfydryl bridges. Fc fragment 110 allows Seldeg 20a to bind an FcRn molecule on an FcRn-expressing cell. In the example shown in FIG. 2A, antigen 100 may be fused to Fc fragment 110a at the N-terminus of the hinge-CH$_2$—CH$_3$ 120. When antigen 100 is fused to Fc fragment 110a and the resulting antigen-Fc fragment dimerizes with another Fc fragment 110b lacking an antigen, using the knobs-into-holes strategy (for example, as described in Moore, G. L., Bautista, C., Pong E., Nguyen, D. H., Jacinto, J., Eivazi, A., Muchhal, U. S., Karki, S., Chu, S. Y., Lazar, G. A., 2011). A novel bispecific antibody format enables simultaneous bivalent and monovalent co-engagement of distinct target antigens. MAbs 3, 546-557), a heterodimeric Seldeg molecule 20a as shown is produced. Seldeg 20a has an Fc fragment with a monomeric display of antigen 100, which avoids the formation of multimeric immune complexes that can cause inflammation and other adverse effects. Although Seldegs containing only antigen 100 fused to Fc fragment 110a may be produced and used in some circumstances, due to the tendency of an Fc fragment to dimerize, a dimer will typically be produced. In order to avoid Fc fragment dimers in which both Fc fragments 110a have a fused antigen 100, which can lead to the formation of multimeric immune complexes, Seldegs are designed with knobs-into-holes mutations and/or electrostatic steering mutations (for example, as described in Gunasekaran, K., Pentony, M., Shen, M., Garrett, L., Forte, C., Woodward, A., Ng, S. B., Born, T., Retter, M., Manchulenko, K., Sweet, H., Foltz, I. N., Wittekind, M., Yan, W. (2010) Enhancing antibody Fc heterodimer formation through electrostatic steering effects: applications to bispecific molecules and monovalent IgG. J. Biol Chem 285, 19637-19646) to promote heterodimer formation, so there is only one Fc with one antigen fused. Other approaches can also be used to generate heterodimers, such as the insertion of a $(G_4S)_{13}$ linker peptide between the C-terminus of the antigen-Fc fusion and N-terminus of a second Fc fragment (for example, as described in Zhou, L., Wang, H Y., Tong, S., Okamoto, C. T., Shen, W C., Zaro, J. L. (2016) Single chain Fc-dimer-human growth hormone fusion protein for improved drug delivery. Biomaterials, 117, 24-31). DNA and protein sequences of several examples of Seldegs comprising knobs-into-holes mutations, electrostatic steering mutations, and/or arginine mutations or other mutations that reduce Fc gamma receptor and complement binding are described in Example 10.

Additional examples of knobs-into-holes mutations include Y349T/T394F:S364H/F405A and Y349T/F405F:S364H/T394F (for example as described in Moore, G. L., Bautista, C., Pong, E., Nguyen, D. H., Jacinto, J., Eivazi, A., Muchhal, U.S., Karki, S., Chu, S. Y., Lazar, G. A. (2011) A novel bispecific antibody format enables simultaneous bivalent and monovalent co-engagement of distinct target antigens. MAbs 3, 546-557) and T366W:T366S:L368A/Y407V (for example as described in Atwell, S., Ridgway, J. B. B., Wells, J. A., Carter, P (1997) Stable heterodimers from remodeling the domain interface of a homodimer using a phage display library. J. Mol. Biol., 270, 26-35) among others identifiable by persons skilled in the art. The residue numbering of these exemplary knobs into holes mutations refers to the EU antibody numbering system, as would be understood by persons skilled in the art.

Additional examples of electrostatic steering mutations include E356K/D399K:K392D/K409D and K409D/K370D: D357K/D399K (for example as described in Gunasekaran, K., Pentony, M., Shen, M., Garrett, L., Forte, C., Woodward, A., Ng, S. B., Born, T., Retter, M., Manchulenko, K., Sweet, H., Foltz, I. N., Wittekind, M., Yan, W. (2010). Enhancing antibody Fc heterodimer formation through electrostatic steering effects: applications to bispecific molecules and monovalent IgG. J. Biol Chem 285, 19637-19646) among others identifiable by persons skilled in the at. The residue numbering of these exemplary electrostatic steering mutations refers to the EU antibody numbering system, as would be understood by persons skilled in the art.

Additional examples of arginine mutations or other mutations to reduce binding to Fc gamma receptors and complement (C1q) include G236R/L328R (for example as described in Horton, H. M., Bernett, M. J., Pong, E., Peipp, M., Karki, S., Chu, S. Y., Richards, J. O., Vostiar, I., Joyce, P. F., Repp, R., Desjarlais, J. R., Zhukosky, E. (2010) Potent in vitro and in vivo activity of an Fc-engineered anti-CD19 monoclonal antibody against lymphoma and leukemia. Cancer Res., 68, 8049-8057; Moore, G. L., Bautista, C., Pong, E., Nguyen, D. H., Jacinto, J., Eivazi, A., Muchhal, U. S., Karki, S., Chu, S. Y., Lazar, G. A. (2011). A novel bispecific antibody format enables simultaneous bivalent and monovalent co-engagement of distinct target antigens. MAbs 3, 546-557), N297A or N297Q (for example as described in Tao, M H., Morrison, S. L. (1989) Studies of aglycosylated chimeric mouse-human IgG: role of carbohydrate in the structure and effector functions mediated bu the human IgG constant region. J Immunol., 143, 2595-2601; Lux. A., Yu, X., Scanlan, C. N., Nimmerjahn, F. (2013) Impact of immune complex size and glycosylation on IgG binding to human FcγRs. J. Immunol., 190, 4315-4323), D265A (for example as described in Lux, A., Yu, X., Scanlan, C. N., Nimmerjahn, F (2013) Impact of immune complex size and glycosylation on IgG binding to human FcγRs. J. Immunol, 190, 4315-4323; Clynes, R. A., Towers, T. L., Presta, L. G., Ravetch, J. V. (2000) Inhibitory Pc receptors modulate in vivo cytotoxicity against tumor targets. Nat. Med. 6, 443-446). L234A/L235A (for example as described in Wines, B. D., Powell, M. S., Parren, P. W. H. I., Barnes, N., Hogarth, P. M. (2000) The IgG Fc contains distinct Fc receptor (FcR) binding sites: the leukocyte receptors FcγRI and FcγRIIa bind to a region in the Fc distinct from that recognized by neonatal FcR and protein A. J. Immunol., 164, 5313-5318), and L234A/L235A/P329G (for example as described in Schlothauer, T., Herter, S., Koller, C. F., Grau-Richards, S., Steinhart, V., Spick, C., Kubbies, M., Klein, C., Umana, P., Mossner, E. (2016) Novel human IgG1 and IgG4 Fc-engineered antibodies with completely abolished effector functions PEDS, 29, 457-466), among others identifiable by persons skilled in the art. The residue numbering of these exemplary arginine mutations or other mutations to reduce binding to Fc gamma receptors and complement (C1q) refers to the EU antibody numbering system, as would be understood by persons skilled in the art.

Other mutations to ablate FcγR and/or complement binding that target residues at, or in proximity to, the location of the FcγR and complement binding sites can be used. These sites on the Fc region of IgG have been localized (for example, as described in Jefferis, R., Lund, J. (2002) Interaction sites on human IgG-Fc for FcγR: current models. Immunol. Letts., 82, 57-65; Duncan, A. R., Winter. G (1988) The binding site for C1q on IgG. Nature, 332, 738-740; Idusogie, E. E., Presta, L. G., Gazzano-Santoro, H., Totpal, K., Wong, P. Y., Ultsch, M., Meng, G., Mulkerrin, M. G. (2000) Mapping of the C1q binding site on rituxan, a chimeric human antibody with a human IgG1 Fc. J. Immunol., 164, 4178-4184; Hogarth, P. M., Anania, J., Wines, B. D. (2014) The FcγR of humans and non-human primates and their interaction with IgG: implications for induction of inflammation, resistance to infection and the use of therapeutic monoclonal antibodies. Cur. Top. Microbiol. Immunol., 382, 321-352).

Seldegs may include Fc fragments derived from immunoglobulin classes or isotypes that do not bind, or have very weak binding, to Fc gamma receptors or complement such as human IgG2 or human IgG4.

For some applications such as diagnostic imaging, Seldegs may include Fc fragments with binding sites for Fc gamma receptors and/or complement to increase inflammatory responses against the antigen that is present in the Seldeg.

Fc fragment 110 may be modified to substantially increase its binding affinity for FcRn at near-neutral pH as compared to unmodified Fc fragments. For example, the dissociation constant between Fc fragment 110 and FcRn at a pH greater than 6.8 and less than 7.5 may be less than 10 μM as determined by surface plasmon resonance or other biophysical method. However, Fc fragment 110 may have a similar or increased affinity for FcRn as compared to an unmodified Fc fragment at acidic endosomal pH (about 6.0), or it may be modified to have a much lower or negligible binding affinity for FcRn at endosomal pH as compared to an unmodified Fc fragment. This increase in binding affinity at near neutral pH allows each Seldeg to cause its bound target antigen-specific antibody to be efficiently internalized and trafficked into late endosomes or lysosomes in FcRn-expressing cells. Enhanced binding affinity of the Fc fragment for FcRn may be achieved by insertion of mutations. Naturally-occurring IgGs have a substantially higher binding affinity for FcRn at acidic pH levels as opposed to near-neutral pH. This property is essential for the recycling and transport of IgG within FcRn-expressing cells. In contrast, an increase in binding affinity for FcRn at pH 7.4, for example, results in receptor-mediated internalization into cells and lysosomal delivery.

Fc fragment 110 may also be modified to eliminate or substantially reduce the binding affinity for Fc gamma receptors and complement (C1q). This modification prevents inflammatory responses caused by the formation of multimeric immune complexes. For example, as described in Example 10, the Fc regions can be mutated (G236R/L328R; EU numbering) (for example as described in Moore, G. L., Bautista, C., Pong, E., Nguyen, D. H., Jacinto, J., Eivazi, A., Muchhal, U. S., Karki, S., Chu, S. Y., Lazar, G. A. (2011). A novel bispecific antibody format enables simultaneous bivalent and monovalent co-engagement of distinct target antigens. MAbs 3, 546-557) (EU numbering), herein also referred to as "arginine mutations", so that they do not bind Fc gamma receptors. In Example 10, these mutations correspond to residues 22 and 114 of Fc-Syt1 (see SEQ ID NO: 10), and residues 144 and 236 of MOG-Seldeg-PS (see SEQ ID NO: 8). Other examples of mutations that substantially reduce or ablate binding to Fc gamma receptors and complement include N297A or N297Q (E U numbering; for example as described in Tao, M H., Morrison, S. L. (1989) Studies of aglycosylated chimeric mouse-human IgG: role of carbohydrate in the structure and effector functions mediated by the human IgG constant region. J. Immunol., 143, 2595-2601; Lux, A., Yu, X., Scanlan, C. N., Nimmerjahn, F.

(2013) impact of immune complex size and glycosylation on IgG binding to human FcγRs. J. Immunol., 190, 4315-4323), D265A (E U numbering; for example as described in Lux, A., Yu, X., Scanlan, C. N., Nimmerjahn, F. (2013) Impact of immune complex size and glycosylation on IgG binding to human FcγRs. J. Immunol., 190, 4315-4323; Clynes, R. A., Towers, T. L., Presta, L. G., Ravetch, J. V. (2000) Inhibitory Fc receptors modulate in vivo cytotoxicity against tumor targets. Nat. Med. 6, 443-446), L234A/L235A (EU numbering; for example as described in Wines, B. D., Powell, M. S., Parren, P. W. H. I., Barnes, N., Hogarth, P. M. (2000) The IgG Fc contains distinct Fc receptor (FcR) binding sites: the leukocyte receptors FcγRI and FcγRIIa bind to a region in the Fc distinct from that recognized by neonatal FcR and protein A. J. Immunol., 164, 5313-5318), L234A/L235A/ P329G (EU numbering; for example as described in Schlothauer, T., Herter, S., Koller, C. F., Grau-Richards, S., Steinhart, V., Spick, C., Kubbies, M., Klein, C., Umana, P., Mossner, E. (2016) Novel human IgG1 and IgG4 Fc-engineered antibodies with completely abolished effector functions. PEDS, 29, 457-466), among others identifiable by persons skilled in the art. A reduction in binding affinity for Fc gamma receptors of at least 10-fold is preferred.

Figure 2B:
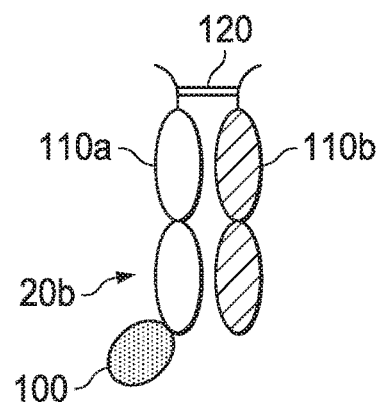
Figure 2C:
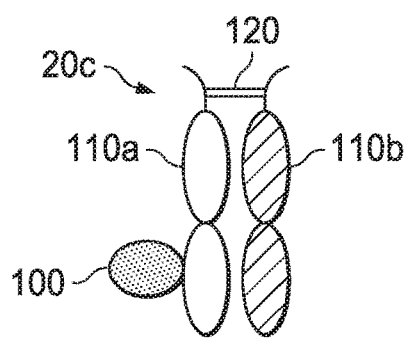

As shown in FIG. 2B, in Seldeg 20b antigen 100 may be attached to Fc fragment 110a at another terminal location, or as shown in FIG. 2C, in Seldeg 20c, antigen 100 may be attached at a non-terminal location. Any location that does not prevent specific FcRn binding is suitable. Such locations include amino acid residues that are sufficiently distant from the FcRn interaction site (encompassing residues 252-256, 309-311, 433-436 at the CH2-CH3 domain interface; EU numbering) so as not to either directly or sterically block FcRn binding, as would be identifiable by skilled persons.

Antigen 100 may be fused to Fc fragment 110 in any suitable manner, including attachment via a chemical reaction, attachment through a linker, or during formation of a single combined antigen-Fc fragment protein. Examples of chemical coupling that could be used are: amine-to-amine (NHS esters), sulfhydryl-to-sulfhydryl (maleimide), amine-to-sulfhydryl (NHS ester/maleimide), sulfhydryl-to-carbohydrate (maleimide/hydrazide), or attachment via an unnatural amino acid with the desired chemical reactivity. This unnatural amino acid can be inserted during recombinant production of the Fc fragment and/or antigen. Polyethyleneglycol (PEG) spacers can also be inserted between the chemically conjugated proteins, protein fragments or other molecules. Possible linkers include repeats of glyine-serine linker peptides, or other more rigid linker peptides, that are encoded in the recombinant expression plasmid for the antigen-Fc fusion. Linkage chemistry, sites of linkage and choice of peptide can be guided by molecular modeling, and can be designed to minimize loss of binding activity of the antigen or the protein/protein fragment targeting the cell surface molecule, as would be understood by skilled persons.

Figure 2D:
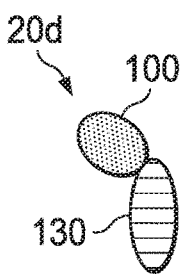

FIG. 2D is a schematic representation of Seldeg 20d in which antigen 100 is attached to antibody variable region 130. Antibody variable region 130 specifically binds to a cell surface receptor or cell surface molecule. Antibody variable region 130 may be an entire variable region or a fragment thereof, so long as it can specifically bind to a cell surface receptor or cell surface molecule. Antibody variable region 130 may include portions of a non-variable region of an antibody that is configured to bind to a cell surface receptor or cell surface molecule. For example, antibody variable region 130 may be a single-domain antibody (sdAb) or camelid-derived VHH domain (also commonly referred to as a nanobody). Such variable regions have the overall fold of an immunoglobulin domain, comprising two anti-parallel β-sheets, and can also include domains from other members of the immunoglobulin superfamily such as T cell receptor variable domains, constant region domains of antibodies or domains of the coreceptor, CD4, among others identifiable by persons skilled in the art. Antibody variable region 130 may be present as a monomer as shown in FIG. 2D, or as a multimer. For example, if antibody variable region 130 is present as a nanobody, it may be engineered with a linker peptide such as GSSGGSGGGGS (SEQ ID NO: 35) between the C-terminus of the first nanobody and the N-terminus of the second nanobody to form a dimer, resulting in increased binding avidity for target receptor/molecule. If antibody variable region 130 is a nanobody or another protein that is engineered to form multimers, variants without antigen 100 may be included during Seldeg formation so that multimers contain only one copy of antigen 100, just as described above for Seldegs containing Fc fragments. Antibody variable regions can also include heterodimers of heavy chain variable (VH) domains linked by peptide linkers to light chain variable (VL) domains to form scFv fragments. The linker sequences that are used to link VH and VL domains are well known to those with skill in the art and include the GGGGSGGGGSGGGGS [(G$_4$S)$_3$] (SEQ ID NO: 36) sequence that connects the C-terminus of the VH domain to the N-terminus of the VL domain. In some embodiments, the C-terminus of the VL domain can be connected to the N-terminus of the VH domain with similar linker sequences. ScFvs that bind to a cell surface receptor or other cell surface molecule can be isolated from libraries of scFvs using phage display, yeast display or other antibody display approaches. The targeting protein component of a Seldeg could also include Fab fragments of an antibody that can be isolated from libraries of Fab fragments using phage display, yeast display etc. For nanobodies, scFvs and Fab fragments, affinities for binding to a cell surface receptor or cell surface molecule can be increased by randomly mutating residues in the complementarity determining regions (CDRs), or by using error-prone polymerase chain reaction, to generate libraries of mutated nanobodies or variable domains. Exemplary CDR residues that would be targeted are those in CDR3 of the light chain variable domain (residues 89-97; Kabat numbering) and CDR3 of the heavy chain variable domain (residues 95-102; Kabat numbering). These libraries can be displayed on phage or yeast and higher affinity variants selected using approaches known to those with skill in the art.

Although FIG. 2D illustrates antigen 100 at a terminal location of antibody variable region 130, it may instead be located at a non-terminal location. Antigen 100 may be fused to antibody variable region 110 in any suitable manner, including attachment via a chemical reaction, attachment through a linker, or during formation of a single combined antigen-antibody variable region fusion protein.

Figure 2E:
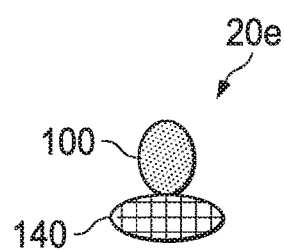

A Seldeg may also contain an antigen component fused to targeting component that includes a protein other than an antibody or antibody fragment, providing that this protein is configured to bind to a cell surface receptor or other cell surface molecule. For example, as shown in FIG. 2E, Seldeg 20e includes antigen 100 fused to albumin or an albumin fragment 140 able to bind FcRn. The albumin or albumin fragment may be mutated or modified so that it binds with increased affinity to FcRn. For example, mutations can be inserted into the FcRn binding domain (DIII) of (human serum) albumin using error prone PCR followed by display of libraries of mutated albumin variants on yeast or phage, and selection of higher affinity variants. Alternatively, higher affinity variants can be generated by mutating residues at or near the albumin:FcRn interface and either selecting or screening for albumin variants with increased binding affinity. Although FIG. 2E illustrates antigen 100 at a non-terminal location of albumin or albumin fragment 140, it may instead be located at a terminal location. Antigen 100 may be fused to albumin or albumin fragment 140 in any suitable manner, including attachment via a chemical reaction, attachment through a linker, or during formation of a single combined antigen-FcRn-binding protein.

Figure 2F:
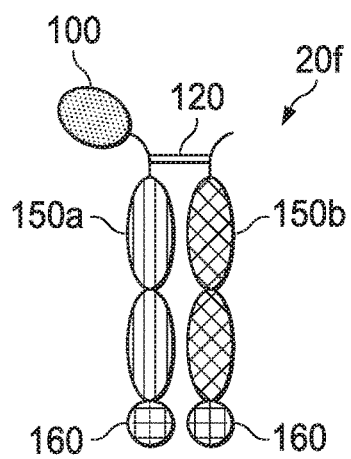
Figure 2G:
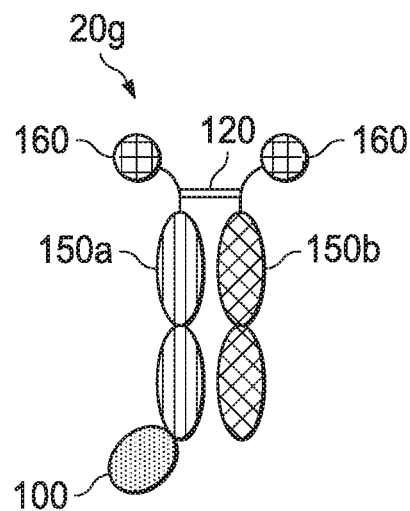

FIG. 2F is a schematic representation of exemplary Seldeg 20f including antigen 100 attached to the N-terminus of an Fc fragment 150. In the example shown in FIG. 2F, protein or protein fragments 160 that bind to a cell surface receptor or cell surface molecule are attached to the C-terminus of Fc fragment 150a. For example, the protein or protein fragment may be the C2A domain of synaptotagmin that binds to phosphatidylserine (PS). Fc fragment 150 can be engineered to bind to FcRn with increased affinity and may be mutated so that it binds to Fc gamma receptors and complement with very low or no detectable binding affinity. In order to avoid Fc fragment homodimers having two Fc fragments 150a with fused antigen 100, which can lead to the formation of multimeric immune complexes, Seldegs as shown in FIG. 2F are designed with knobs-into-holes mutations and/or electrostatic steering mutations to promote heterodimer formation, so there is only one Fc with one Fc-antigen. In FIG. 2F, both Fc fragments 150a and 150b have proteins or protein fragments that bind to the cell surface protein or other cell surface molecule fused to them; alternatively, only one such protein or protein fragment may be present. In the exemplary Seldeg shown in FIG. 2G, the antigen 100 and protein or protein fragments 160 that bind to a cell surface receptor or cell surface molecule are fused to the C- and N-termini of the Fc fragments 150a and 150b, respectively, to generate Seldeg 20g.

Figure 2H:
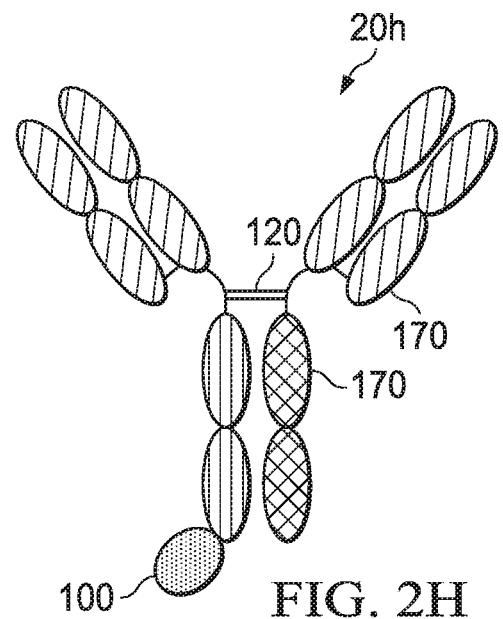

FIG. 2H is a schematic representation of exemplary Seldeg 20h including antigen 100 attached to the C-terminus of an antibody 170 that binds to a cell surface protein or cell surface molecule. The Fc fragment (Fc) in the antibody can be engineered to bind to FcRn with increased affinity and may be mutated so that it binds to Fc gamma receptors and complement with very low or no detectable binding affinity. In order to avoid antibody homodimers in which both Fc fragments have a fused antigen 100, which can lead to the formation of multimeric immune complexes, Seldegs as shown in FIG. 2H are designed with knobs-into-holes mutations and/or electrostatic steering mutations to promote heterodimer formation, so there is only one antibody heavy chain per antibody molecule with attached antigen 100. Both Fab fragments of the antibody may bind to the same cell surface protein or other cell surface molecule; alternatively, they could bind to two or more different cell surface proteins or molecules.

Figure 2I:
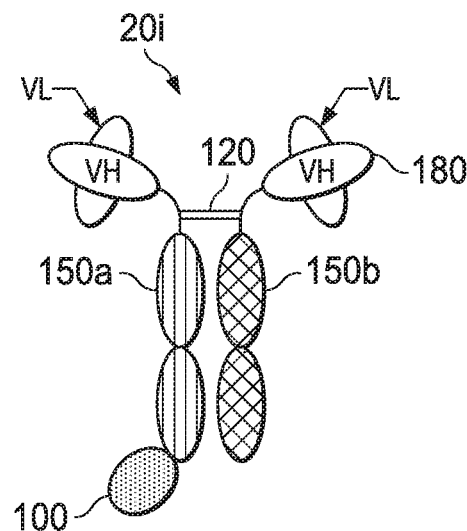

FIG. 2I is a schematic representation of exemplary Seldeg 20i comprising antigen 100 attached to the C-terminus of a scFv (180)-Fc fusion that binds to a cell surface protein or cell surface molecule. The Fc fragment (Fc) in the antibody can be engineered to bind to FcRn with increased affinity and may be mutated so that it binds to Fc gamma receptors and complement with very low or no detectable binding affinity. In order to avoid antibody homodimers in which both Fc fragments have a fused antigen 100, which can lead to the formation of multimeric immune complexes, Seldegs as shown in FIG. 2I are designed with knobs-into-holes mutations and/or electrostatic steering mutations to promote heterodimer formation, so there is only one antibody heavy chain-scFv fusion per molecule with attached antigen 100. Both scFv fragments of the antibody may bind to the same cell surface protein or other cell surface molecule; alternatively, they could bind to two or more different cell surface proteins or molecules.

Figure 2J:
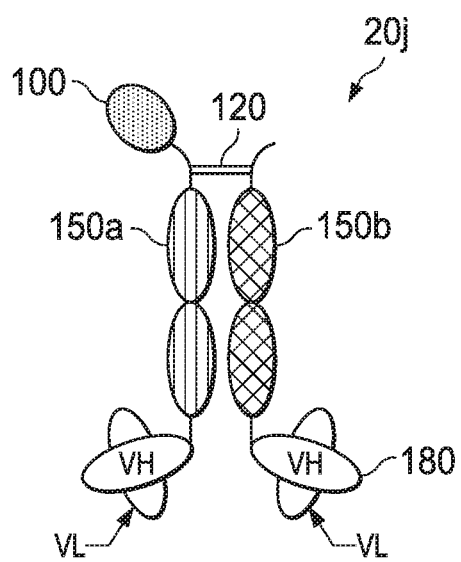

FIG. 2J is a schematic representation of exemplary Seldeg 20j comprising antigen 100 attached to the N-terminus of an -Fc-scFv (180) fusion that binds to a cell surface protein or cell surface molecule. The Fc fragment (Fc) in the antibody can be engineered to bind to FcRn with increased affinity and may be mutated so that it binds to Fc gamma receptors and complement with very low or no detectable binding affinity. In order to avoid antibody homodimers in which both Fc fragments have a fused antigen 100, which can lead to the formation of multimeric immune complexes, Seldegs as shown in FIG. 2.1 are designed with knobs-into-holes mutations and/or electrostatic steering mutations to promote heterodimer formation, so there is only one antibody heavy chain-scFv fusion per molecule with attached antigen 100. Both scFv fragments of the antibody may bind to the same cell surface protein or other cell surface molecule; alternatively, they could bind to two or more different cell surface proteins or molecules.

Figure 2K:
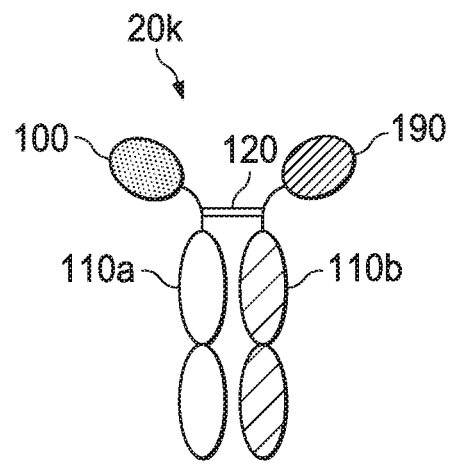

As shown in FIG. 2K, in exemplary Seldeg 20k two antigen components (100, 190) may be attached to a targeting component, for example Fc fragment 110a and Fc fragment 110b at an N-terminal or other location to generate a Seldeg that can clear antigen-specific antibodies of different specificities. Seldegs as shown in FIG. 2K are designed with knobs-into-holes mutations and/or electrostatic steering mutations to promote heterodimer formation, so there is an antigen molecule of each type (100, 190) in each Seldeg molecule.

Figure 2L:
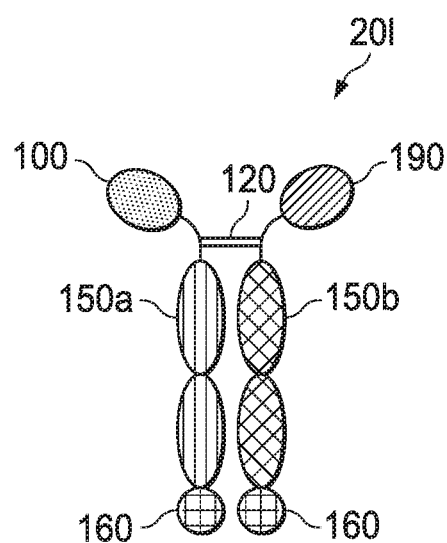

FIG. 2L is a schematic representation of exemplary Seldeg 20l comprising antigen 100 and antigen 190 attached to the N-termini of an Fc fragment 150. In the exemplary embodiment shown in FIG. 2L, protein or protein fragments 160 that bind to a cell surface receptor or cell surface molecule are attached to the C-termini of Fc fragment 150a and 150b. Seldegs as shown in FIG. 2L are designed with knobs-into-holes mutations and/or electrostatic steering mutations to promote heterodimer formation, so there is an antigen molecule of each type (100, 190) in each Seldeg molecule. In FIG. 2L, both Fc fragments 150a and 150b have proteins or protein fragments that bind to the cell surface protein or other cell surface molecule fused to them, but in other embodiments, only one such protein or protein fragment may be present.

Figure 2M:
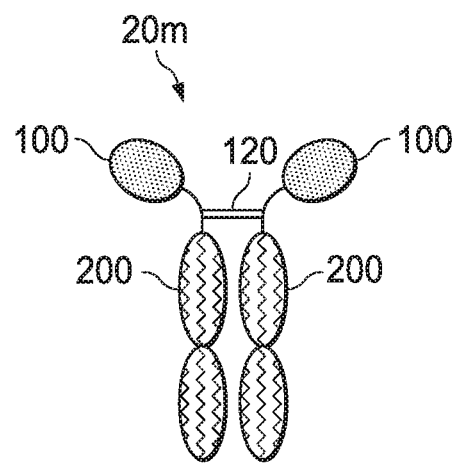

As shown in FIG. 2M, in exemplary Seldeg 20m two molecules of the same antigen (100) may be attached to Fc fragment 200 at N-terminal or other locations to generate exemplary Seldeg 20m. This exemplary Seldeg is a homodimer that contains mutations to enhance binding to FcRn, and does not contain knobs-into-holes and/or electrostatic steering mutations.

Figure 2N:
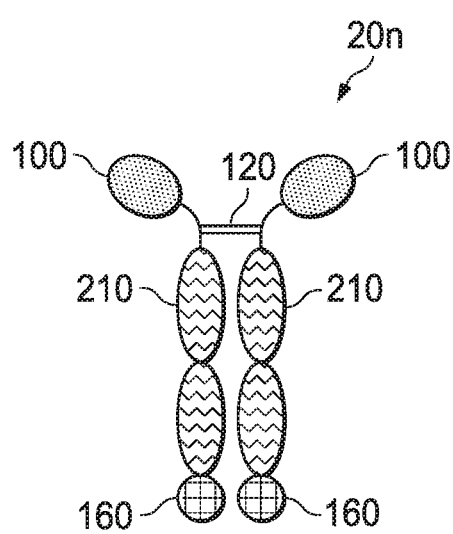

FIG. 2N is a schematic representation of exemplary Seldeg 20n comprising two molecules of the same antigen (100) attached to the N-termini of an Fc fragment 210. In the exemplary embodiment shown in FIG. 2N, protein or protein fragments 160 that bind to a cell surface receptor or cell surface molecule are attached to the C-terminus of Fc fragment 210. This exemplary Seldeg is a homodimer and does not contain knobs-into-holes and/or electrostatic steering mutations. In FIG. 2N, the homodimeric Fc fragment 200 has proteins or protein fragments that bind to the cell surface protein or other cell surface molecule fused to both polypeptide chains, but in other embodiments, only one such protein or protein fragment may be present.

For Seldegs that target FcRn, similar principles may be applied to other proteins able to bind FcRn. In addition, the FcRn-targeting Seldeg or methods of forming it may be affected by properties of the FcRn-binding protein. Although albumin tends to not form dimers or other multimers, other FcRn-binding proteins may, in which case the final Seldeg may be formed in a manner to those containing antibody fragments so that each Seldeg contains only one copy of the antigen. In the examples shown in FIG. 2A, 2B, 2C, 2F, 2G, 2H, 2I, 2J, 2K, 2L, the Seldeg has two antibody Fc fragments that are engineered with knobs-into-holes mutations and/or electrostatic steering mutations to drive the formation of heterodimers comprising one antigen linked to one Fc fragment and one Fc fragment with no antigen attached. The Fc fragment can be further engineered to bind to FcRn with increased affinity at near neutral pH (FIG. 2A, 2B, 2C, 2K, 2M) or connected to one or more proteins, scFv fragments. Fab fragments or other molecules that target one or more cell surface receptors or molecules (FIGS. 2F, 2G, 2H, 2I, 2J, 2L, 2N). The Fc fragments in the examples shown in FIG. 2F, 2G, 2H, 2I, 2J, 2L, 2N can also be engineered to bind with higher affinity to FcRn so that they target both FcRn and one or more cell surface receptors or molecules.

Albumin binds more strongly to FcRn at acidic pH than at neutral pH. However, albumin may also be modified to alter its binding affinities at near-neutral or endosomal pH to encourage degradation of the target antigen-specific antibody and recycling of the Seldeg. Similarly, antibody variable region FcRn-binding proteins may be affected by pH in a manner specific to that protein, but they may still be modified to alter its binding affinities at near-neutral or endosomal pH to encourage degradation of the target antigen-specific antibody. These FcRn-binding proteins can be isolated from libraries of immunoglobulin variable domains, scFv (VH:VL heterodimers in which VH and VL domains are connected to each other by linker peptides such as GGGGSGGGGSGGGGS) (SEQ ID NO: 36) or Fab fragments using phage display, yeast display or other technologies known to those with skill-in-the-art. These libraries can either be derived from naturally occurring antibody variable genes, or can be generated using approaches that result in 'semi-synthetic' libraries wherein complementarity determining regions (CDRs) are produced using randomized oligonucleotide sequences. Further increases to their affinities can be achieved by, for example, inserting random mutations in the CDRs using error-prone PCR followed by selection using phage display or yeast display. Exemplary CDR residues that would be targeted are those in CDR3 of the light chain variable domain (residues 89-97; Kabat numbering) and CDR3 of the heavy chain variable domain (residues 95-102; Kabat numbering). Similar methods can be used to isolate antibody-based proteins or scaffold-based proteins that bind to other cell surface receptors/molecules.

Seldegs may include any targeting component that is configured to specifically bind to a receptor or other molecule on the cell surface (FIG. 2D. 2E. 2F, 2G, 2H, 2I, 2J, 2L or 2N,). The targeting component is fused directly or indirectly (e.g., via a linker) to an antigen component having one molecule of each type of antigen, antigen fragment or antigen mimetic to reduce antibody-mediated crosslinking. The term "type of antigen" as used herein refers to an antigen that binds to a specific antibody. Accordingly, a Seldeg can include more than one antigen type, wherein each Seldeg has only one molecule of each antigen type. If the targeting protein contains an immunoglobulin-derived Fc fragment, the Fc region can be mutated so that it does not bind, or binds at substantially reduced levels, to Fc gamma receptors and complement. Several different possible configurations of Seldegs are shown in FIG. 2A-N; these are shown as examples and are not limiting, since multiple other configurations can also be envisaged by those with skill-in-the-art.

Seldegs may include Fc fragments that bind to Fc gamma receptors and complement. The presence of the Fc gamma and complement binding sites may be desired in the context of particular application areas, when an immune response against the antigen in the Seldeg is desirable (for example, in tumor imaging). In such applications, Seldegs that are configured to bind to Fc gamma receptors and complement may be preferred. For example, Seldegs that include Fc fragments lacking engineered mutations to have decreased binding affinity or no binding affinity for Fc gamma receptors and/or complement (C1q) described herein, such as arginine mutations, may be configured to elicit such an immune response. Seldegs that include Fc fragments with mutations known to those with skill in the art to increase binding to Fc gamma receptors and or complement (C1q) may also be configured to elicit such an immune response. Such Seldegs may also be configured to comprise more than one antigen molecule per Seldeg (FIG. 2K, 2L, 2M or 2N) to enhance immune complex formation.

For example, Seldegs can have variations in numbers of targeting domains or antibody fragments (e.g. Fab fragments or scFv fragments) that range from 1-3 targeting domains or antibody fragments (FIG. 2). These targeting domains or antibody fragments can be linked to immunoglobulin Fc fragments, whereas in others, the targeting domains or antibody fragments may be linked to each other; the antigen and antibody fragments can be fused to Fc fragments or each other in different orientations (FIG. 2); Seldegs can include linker sequences that vary in length and composition between the fusion proteins, domains or fragments can be used e.g. IEGRMD (SEQ ID NO: 37), GGGGS (SEQ ID NO: 38) or 2-3 repeats of this linker; antigen mimetics such as small molecules or peptides can be used; the Fc fragment in Seldegs may be mutated so that it has substantially reduced binding affinity for Fc gamma receptors, complement, and increased affinity for binding to FcRn; The Fc fragments of a Seldeg may have mutations such as knobs-into-holes and/or electrostatic steering mutations so that heterodimers of antigen-linked and non-antigen-linked Fc fragments or containing two different antigens are formed.

Seldegs can include the following antigens that include proteins, glycoproteins and nucleic acids associated with autoimmune disease, including autoimmune encephalitides: myelin oligodendrocyte glycoprotein (MOG), myelin basic protein, proteolipid protein, myelin-associated glycoprotein, myelin-associated oligodendrocyte basic protein, transaldolase, acetylcholine receptor, muscle specific kinase, low density lipoprotein receptor related protein 4, insulin, islet antigen 2, glutamic acid decarboxylase 65, zinc transporter 8, citrullinated antigens, carbamylated antigens, collagen, cartilage gp39, gp130-RAPS, 65 kDa heat shock protein, fibrillarin, small nuclear protein (snoRNP), aquaporin 4, thyroid stimulating factor receptor, nuclear antigens, DNA, histones, glycoprotein gp70, ribosomes, pyruvate dehydrogenase dehydrolioamide acetyltransferase, hair follicle antigens, human tropomyosin isoform 5, N-Methyl-D-aspartate (NMDA) receptor, α-amino-3-hydroxy-5-methyl-4-isoxazolepropionic acid (AMPA) receptor, $GABA_A$ and $GABA_B$ receptors, glycine receptor, dipeptidyl-peptidase-like protein 6 (DPPX), glutamate receptor (GluR5), voltage gated potassium channel, Hu, Thyroid peroxidase, thyroglobulin, thyroid stimulating hormone (TSH) receptor, thyroid hormones T3 and T4, desmoglein 1 and 3, among others identifiable by skilled persons. The following antigens are examples of antigens that are associated with tumors and can be incorporated into Seldegs to clear tumor-specific antibodies during diagnostic imaging: HER2, prostate specific membrane antigen (PSMA), prostate stem cell associated antigen (PSCA), c-Met, EpCAM, carcinoembryonic antigen (CEA). Other antigens include therapeutics for which patients have specific antibodies, or transplantation antigens that are recognized by antibodies in transplant recipients. In addition, it is possible to generate molecular mimics (synthetic, protein fragments etc.) of antigens, and these can also be used to generate Seldegs. The above antigens are examples and are not limiting to additional types of possible antigens identifiable by persons skilled in the art upon reading of the present disclosure.

In several examples described herein, the Seldeg can be a heterodimer of fusion proteins comprising the amino acid sequences of SEQ ID NO: 2 plus SEQ ID NO: 6, SEQ ID NO: 4 plus SEQ ID NO: 6, SEQ ID NO: 8 plus SEQ ID NO: 10, SEQ ID NO: 12 plus SEQ ID NO: 14, SEQ ID NO: 16 plus SEQ ID NO: 18 plus the antibody light chain SEQ ID NO: 20, SEQ ID NO: 22 plus SEQ ID NO: 24 plus the antibody light chain SEQ ID NO: 20, SEQ ID NO: 26 plus SEQ ID NO: 28, SEQ ID NO: 30 plus SEQ ID NO: 6, SEQ ID NO: 32 plus SEQ ID NO: 6, or SEQ ID NO: 34 plus SEQ ID NO: 6, or homologs thereof.

The Seldeg can be a fusion protein comprising an amino acid sequence having at least 50%, identity with SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18. SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34.

As used herein, "sequence identity" or "identity" in the context of two nucleic acid or polypeptide sequences makes reference to the nucleotide bases or residues in the two sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A functionally equivalent residue of an amino acid used herein typically refers to other amino acid residues having physiochemical and stereochemical characteristics substantially similar to the original amino acid. The physiochemical properties include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

A person skilled in the art would understand that similarity between sequences is typically measured by a process that includes the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two optimally aligned sequences over a comparison window, wherein the portion of the polynucleotide sequence in the comparison window may include additions or deletions (gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein or protein fragment A reference sequence can be, for example, a sequence identifiable in a database such as GenBank and UniProt and others identifiable to those skilled in the art.

As understood by those skilled in the art, determination of percent identity between any two sequences can be accomplished using a mathematical algorithm. Computer implementations of suitable mathematical algorithms can be utilized for comparison of sequences to determine sequence identity. Such implementations include, but are not limited to: CLUSTAL, ALIGN, GAP, BESTFIT, BLAST, FASTA, among others identifiable by skilled persons.

For example, Seldegs according to the present disclosure can have an amino acid sequence having at least 50% sequence identity, preferably at least 80%, more preferably at least 90%, most preferably at least 95% sequence identity compared to SEQ ID NO: 2, SEQ ID NO: 4, SEQ ID NO: 6, or SEQ ID NO: 8, or SEQ ID NO: 10, or SEQ ID NO: 12, or SEQ ID NO: 14, or SEQ ID NO: 16, or SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34.

The antigen-specific antibodies that are targeted by Seldegs can be autoantibodies that are present in a patient, antibodies that bind to therapeutics, antibodies that recognize transplant and modified (e.g. radiolabeled) antibodies or fragments/engineered forms that are used in diagnostic imaging, among others identifiable by persons skilled in the art.

As shown in the examples below, Seldegs are able to selectively deplete target antigen-specific antibodies with specificity for their fused antigen, for example, the target antigen-specific antibodies HER2-specific trastuzumab or pertuzumab ("TZB" or "PZB") and MOG-specific antibody ("8-18C5") As shown in the examples below, Seldegs are able to selectively deplete the target antigen-specific antibodies without negatively affecting the total IgG levels or eliciting an adverse immune reaction. These findings stand in contrast to other approaches, in which treatment results in depletion of total IgGs, through the use of FcRn inhibitors or antibodies that destroy B-cells. Such approaches adversely affect antibodies of non-targeted specificities or B-cell function because they lack the selectivity provided by Seldegs.

Based on this unique selectivity, the Seldeg platform has many applications because Seldegs may be created with many other targeting proteins and antigens. Examples of such applications include treatment of autoimmune disorders, treatment of antibody-mediated rejection prior to or during transplantation, increasing contrast during whole body imaging of tumors (e g., the tumor antigens PSMA, EpCAM, and CEA may be used as antigens for developing additional Seldegs), depleting the bodily concentration of a particular biologic after administration, for instance, if an adverse reaction is observed, removal of antibodies to clear antibodies that recognize a therapeutic prior to delivery of the therapeutic.

Seldegs may be administered in any way able to deliver them to cells expressing the receptor or other molecule on the cell surface that is being targeted, such as via injection, particularly intravenous, subcutaneous or intramuscular injection, or injection into a tissue targeted by the antigen-specific antibody that is to be depleted Seldegs can also be expressed in cells that have been genetically engineered to contain expression constructs encoding Seldegs. In particular, cells can be genetically engineered by introducing expression constructs that encode Seldeg proteins that include proteins or peptides that allow secretion of Seldegs from the engineered cells in situ. For example, patient-derived cells could be transfected with expression constructs encoding Seldegs and the transfected cells delivered back into the patient, using similar approaches to those described for chimeric antigen-receptor (CAR) T cell therapy. The expression constructs would comprise an expression vector known to those with skill in the art and may, for example, contain genes encoding MOG-Seldeg (SEQ ID NO: 1 and 5), with secretion leader peptides such as those derived from immunoglobulin genes linked to the 5' end of the coding sequence for the mature MOG-Seldeg (SEQ ID NO: 1) and Fc (SEQ ID NO: 5).

Seldegs may be administered in an amount that does not block every targeted receptor/cell surface molecule, allowing normal function of the cell surface receptor/molecule. The dose of Seldeg used may be similar to the amount of antibody being targeted for clearance, which will depend, for example, on the specifics of the antibody-mediated disease, or whether Seldegs are being used to improve contrast in diagnostic imaging. The amount of Seldeg used is expected to be less than the total number of receptor types being targeted, so that the normal function of the targeted receptor is not adversely affected. In addition, Seldegs can be designed so that they do not compete with the natural ligand of the cell surface receptor or cell surface molecule for binding, for example, by using nanobodies (VHH) that bind to FcRn at a site that does not overlap with the IgG binding site (for example as described in Andersen, J. T., Gonzalez-Pajuelo, M., Foss, S., Landsverk, O. J. B., Pinto, D., Szyroki, A., de Haard. H. J., Saunders, M., Vanlandshoot, P., Sandlie, I. (2012) Selection of nanobodies that target human neonatal receptor Sci. Rep., 3, 1118) In addition, Seldegs may remove less than 10%, less than 5%, less than 1%, or less than 0.1% of non-targeted antibodies in the circulation or in a tissue targeted by the antigen-specific antibody that is to be depleted. Retention of non-targeted antibodies during and after Seldeg treatment may be important in normal immune function and the avoidance of infections, among other effects as described herein.

Seldegs may be administered daily, weekly, or whenever 50% of patients are expected to have regenerated a threshold amount of targeted antigen-specific antibody in the circulation or in a tissue recognized by the targeted antigen-specific antibody. The levels of targeted antigen-specific antibody can be determined by using enzyme-linked immunosorbent assays (ELISAs) to analyze serum samples. Alternatively, other methods that are well known to those with skill in the art can be used.

In transplant patients at risk for antibody-mediated rejection, the Seldegs may be administered before or after transplantation. An emergency dose of Seldegs may be administered if the target antigen-specific antibody reaches a threshold amount of target antigen-specific antibody in the circulation or in a tissue recognized by the target antigen-specific antibody. The levels of targeted antigen-specific antibody can be determined by using enzyme-linked immunosorbent assays (ELISAs) to analyze serum samples. Alternatively, other methods that are well known to those with skill in the art can be used.

In patients that have antibodies specific for a therapeutic, such as a protein-based therapeutic, the Seldegs may be administered before the delivery of the therapeutic to deplete such antibodies. This is expected to overcome problems associated with rapid antibody-mediated clearance of therapeutics if they have elicited an immune response during prior delivery, or if preexisting antibodies specific for the therapeutic are present in the patient. Pre-existing or induced antibodies specific for the protein-based therapeutic can be detected using a number of different methods (for example such as those described in Xue, L., Clements-Egan, A., Amaravadi, L., Birchler, M., Gorovits, B., Liang, M., Myler, H., Purushothama, S., Manning, M. S., Sung, C. (2017) Recommendations for the assessment and management of pre-existing drug-reactive antibodies during biotherapeutic development. AAPS, 19, 1576-1586).

In diagnostic/theranostic imaging, it is expected that delivery of the radiolabeled imaging antibody will be followed by a period to allow tumor localization. Subsequently, Seldegs can be used to clear radiolabeled antibody from off-target sites (e.g. circulation) to result in improved contrast. For example, this approach can include the following steps' first, a patient is injected with radiolabeled (or other label) antibody that binds to a tumor antigen. Second, following a period (e.g. 16-24 hours) to allow the radiolabeled antibody to bind to the tumor, the Seldeg is injected in an amount that is equivalent in molar amounts to the injected dose of imaging agent. Following a clearance period (e.g. 4-24 hours), the patient is imaged using positron emission tomography or other whole body imaging modality.

The Seldeg may be administered in an amount sufficient to deplete at least 50%, at least 80% or at least 90% of the concentration of the target antigen-specific antibody in the circulation or in a tissue recognized by the target antigen-specific antibody within one hour, two hours, five hours, 24 hours or 48 hours or longer of administration. The persistence of the Seldeg in the body will be a determinant of how long it has activity in depleting antigen-specific antibody. Seldegs can be designed to have different in vivo half-lives by the behavior of the cell surface receptor or cell surface molecule that they target. The affinity of the Seldeg for this cell surface receptor or cell surface molecule can also be modified using mutagenesis and approaches known to those with skill in the art, to result in Seldegs that have different persistence in the circulation and/or tissues. In particular, the Seldeg may be administered in an amount at least approximately equimolar with the amount of antigen-specific antibody to be depleted. The Seldeg can be administered in an amount that is, for example, in an approximately 1:1, 2:1, 3:1, 4:1, 5:1, 6:1, 7:1, 8:1, 9:1, 10:1 or higher molar ratio to the target antigen-specific antibody. In particular, for example, wherein a Seldeg targets an antibody that is administered to a patient (e.g. anti-MOG, or anti-HER2 antibodies, and the like) a Seldeg can be administered in a dose that is for example, in an approximately 1:1, 2:1, 3:1, 4:1, 5:1, 6:1, 7:1, 8:1, 9:1, 10:1 or higher molar ratio to the administered target antigen-specific antibody.

EXAMPLES

The following examples are provided to further illustrate specific embodiments of the disclosure. They are not intended to disclose or describe each and every aspect of the disclosure in complete detail and should be not be so interpreted. Unless otherwise specified, designations of cell lines and compositions are used consistently throughout these examples.

Example 1—Expression and Purification of Seldegs that Bind to FcRN

Figure 3A:
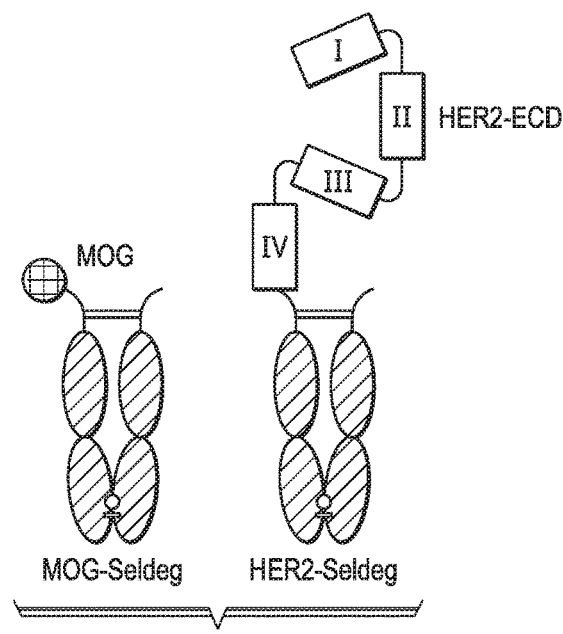
FIG. 3A is a schematic diagram of two exemplary FcRn-targeting Seldegs, a human epidermal growth factor receptor 2 Seldeg ("HER2-Seldeg") and a myelin oligodendrocyte glycoprotein Seldeg ("MOG-Seldeg")

Seldegs that target FcRn on cells contain a recombinant antigen as a monomer linked to a dimeric, human IgG1-derived Fc fragment (FIG. 3A) with mutations to eliminate interactions with human FcγRs and to enhance the binding affinity of the Seldeg Fc fragment to FcRn at near-neutral pH Heterodimer formation of these two Seldegs is achieved by inserting 'knobs-into-holes' mutations in the CH3 domains.

Expression constructs to generate the exemplary HER2-Seldeg (SEQ ID NOS: 3, 4, 5 and 6) were made as follows: to express the polypeptide chain with HER2 fused to an engineered Fc fragment (SEQ ID NO: 3), the gene encoding the HER2 leader peptide and extracellular domain (ECD consisting of 630 residues) was isolated from a HER2-overexpressing breast cancer cell line (BT-474) employing standard molecular biology techniques. This gene was fused via a IEGRMD linker peptide to the N-terminus of the hinge region of a gene encoding the human IgG1-derived Fc fragment using splicing by overlap extension. Mutations to ablate binding to FcγRs (G236R/L328R; EU numbering), enhance binding to FcRn (MST-HN; M252Y/S254T/T256E/H433K/N434F; EU numbering) and generate 'knobs-into-holes' (Y349T/T394F; EU numbering) were inserted into the Fc fragment gene using standard methods. Cysteine (C220; EU numbering) in the hinge region that bridges with cysteine in the light chain constant region was also mutated to serine. Fc fragment genes with FcRn-enhancing mutations, mutations to ablate FcγR binding and without fused antigen were generated with complementary knobs-into-holes mutations (S364H/F405A; EU numbering) (SEQ ID NO: 5). Recombinant proteins were expressed in HEK-293F (Life Technologies) cells following transient transfection with the Gibco Expi293™ expression system kit (Life Technologies) The HER2-Seldeg was purified from culture supernatants using an anion exchange column (SOURCE-15Q, GE Healthcare) at pH 8.0 and a linear salt gradient (0-0.5 M NaCl). Alternatively, HER2-Seldeg can be purified using protein A-Sepharose and standard methods. Following elution from the column (ion exchange or protein A-Sepharose) HER2-Seldeg was dialyzed against phosphate buffered saline (PBS). HER2-Seldeg was further purified using size exclusion chromatography (SEC) (GE Healthcare) in PBS (Lonza) prior to use in experiments. Expression plasmids for other Seldegs were made using analogous methods, and recombinant proteins expressed in transfected HEK-293F cells. Seldegs without FcRn-enhancing mutations (e.g. MOG-Seldeg-PS, MOG-Seldeg-TfR; SEQ ID NOS: 7, 8, 9, 10, 11, 12, 13, 14, 15, 16, 17, 18, 19 and 20) were purified using protein G-Sepharose.

Seldegs targeting antibodies specific for two antigens were generated: (1) the HER2-Seldeg; and (2) the MOG-Seldeg. The antigen HER2 is a well-defined target for therapy and also for diagnostic imaging of HER2-overexpressing tumors with HER2-specific antibodies, such as trastuzumab (TZB) or pertuzumab (PZB). The antigen MOG is recognized by autoreactive antibodies in both animal models of multiple sclerosis (MS) and MS in humans.

Figure 3B:
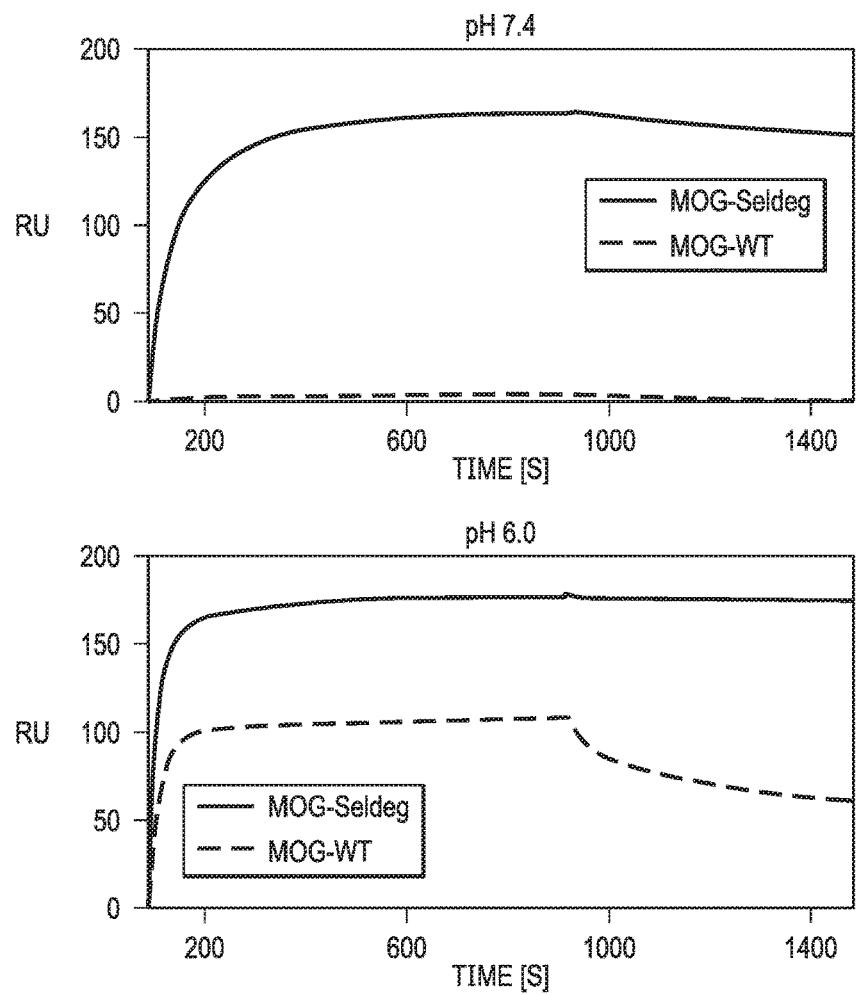
FIG. 3B shows the increased binding of an exemplary FcRn-targeting Seldeg to FcRn at pH 6.0 and 7.4.

The HER2-Seldeg and MOG-Seldeg maintain a significantly higher binding affinity for FcRn at neutral pH and at an acidic pH, in contrast to recombinant fusion proteins comprising HER2 or MOG fused to Fc fragments to generate analogous constructs ("HER2-WT" and "MOG-WT", respectively) to the HER2-Seldeg and MOG-Seldeg, except they lack the FcRn-enhancing MST-HN mutations (M252Y, S254T, T256E, H433K, N434F; EU numbering) that increase binding affinity at near-neutral pH (FIG. 3B). Surface plasmon resonance experiments to analyze the interactions of the recombinant proteins with FcRn were carried out using a BIAcore T200 (GE Healthcare) Binding of Seldeg/WT to recombinant mouse FcRn was analyzed by injecting 100 nM MOG/HER2-Seldeg or MOG/HER2-WT over immobilized FcRn (coupled at ~600 RU on a CM5 sensor chip) in PBS (pH 6.0 or 7.4) plus 0.01% v/v Tween-20 at a flow rate of 10 μl/minute. Flow cells were regenerated following each injection and dissociation phase using 0.15 M NaCl, 0.1 M sodium bicarbonate, pH 8.5. Data were zero-adjusted and background-subtracted (background obtained by injection over a flow cell coupled with buffer only during coupling reaction).

Mutations to increase FcRn binding such as MST-HN were identified using the following approach: residues in proximity to amino acids (e.g. 253, 435) that are known to be essential for FcRn binding were randomly mutated in an Fc fragment gene and the libraries of mutated Fc fragments displayed on phage. Fc fragments with increased binding affinity for FcRn were selected using phage display technology (Ghetie, V., Popov, S., Borvak, J., Radu, C., Matesoi, D., Medesan, C., Ober, R. J., Ward, E. S. (1997) Increasing the serum persistence of an IgG fragment by random mutagenesis, Nature Biotech., 15, 637-640; Dall'Acqua, W. F., Woods, R. M., Ward, E. S., Palaszynski, S. R., Patel, N. K., Brrewah, Y. A., Wu, H., Kiener, P. A., Langermann, S. (2001) Increasing the affinity of a human IgG1 for the neonatal receptor: biological consequences, J. Immunol., 169, 5171-5180). Alternatively, these residues can be mutated to every other possible amino acid and Fc fragments with higher affinity for FcRn identified using methods such as ELISA or surface plasmon resonance binding analyses.

Figure 3C:
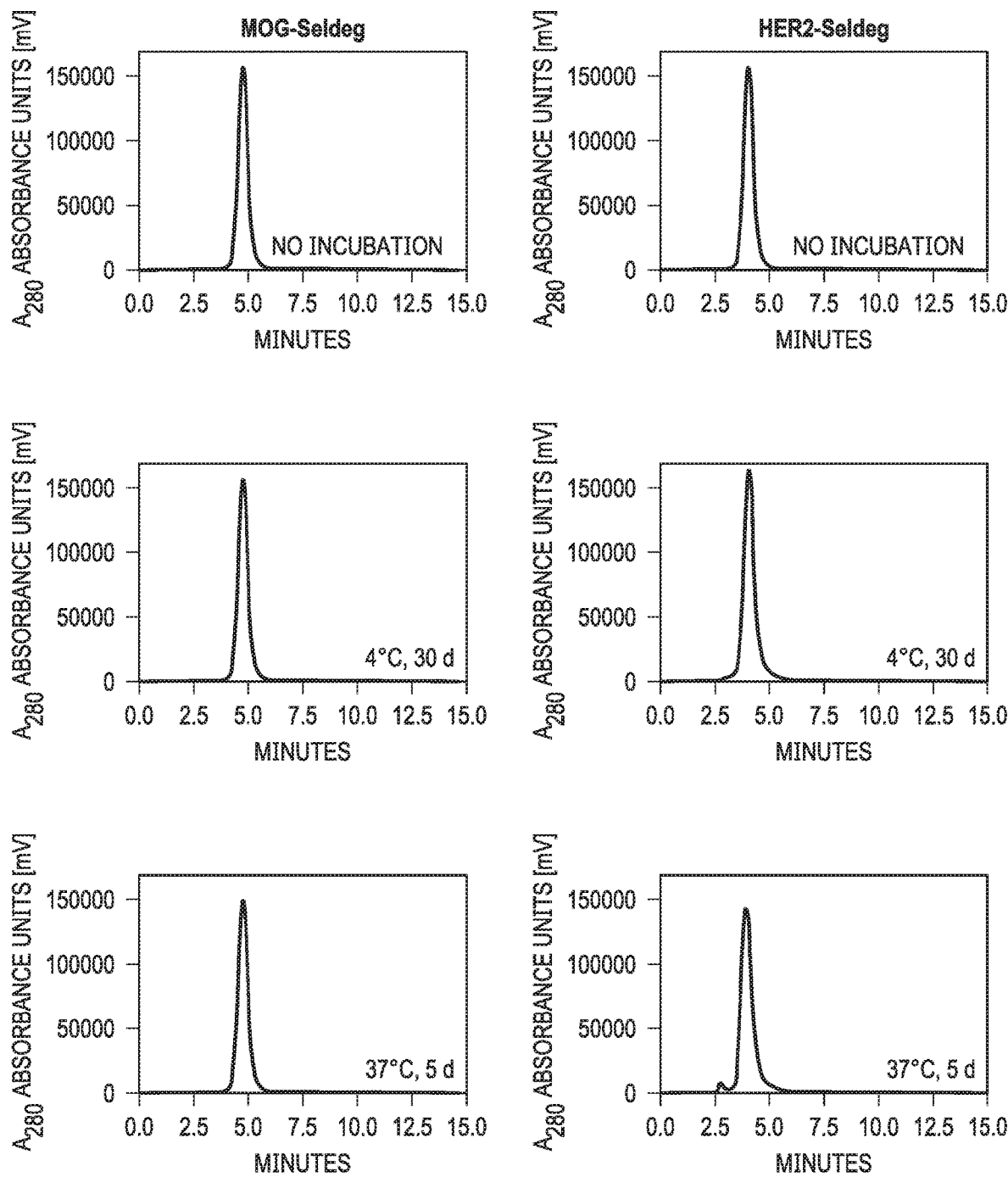
FIG. 3C shows HPLC analyses of two exemplary FcRn-targeting Seldegs following incubation at 4° C. (30 days) and 37° C. (5 days) to evaluate their storage stability.

Size exclusion analyses indicate that the recombinant proteins comprising the Seldegs do not form aggregates following incubation in phosphate buffered saline when incubated for up to 30 days at 4° C. or 5 days at 37° C. (FIG. 3C).

Example 2—Ability of Seldegs that Target FcRn to Deplete Target Antigen-Specific Antibodies in Mice that Transgenically Express Human FcγRs (huFcγR Mice)

To determine the ability of Seldegs to deplete target antigen-specific antibodies, mice that transgenically express human FcγRs (huFcγR mice; Smith, P., DiLillo, D. J., Bournazos, S., Li, F., Ravetch, J. V. (2012). Mouse model recapitulating human Fcγ receptor structural and functional diversity. Proc. Natl. Acad. Sci. USA 109, 6181-6186. were injected with 15 μg of radiolabeled ($^{125}$I-labeled) MOG-specific antibody 8-18C5. 24-hours after the huFcγR mice were injected with 8-18C5, 125 μg or 31 μg of MOG-Seldeg or a control protein was administered via injection.

Figure 3D:
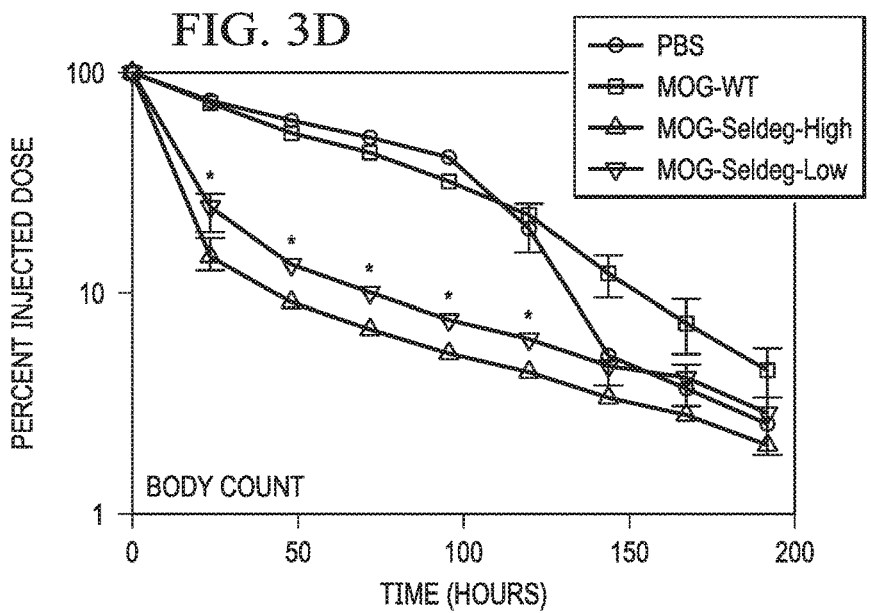
FIG. 3D shows a graph reporting exemplary normalized body counts versus time, showing clearance of an antigen-specific antibody by an exemplary FcRn-targeting Seldeg.

In FIG. 3D, "MOG-Seldeg-High" corresponds to the 125 μg dose and "MOG-Seldeg-Low" corresponds to the 31 μg dose. The controls are phosphate-buffered saline ("PBS") and unmodified MOG-Fc fusion protein ("MOG-WT"). MOG-WT is an analogous construct to the MOG-Seldeg, except it lacks the FcRn-enhancing MST-HN mutations that increase binding affinity at near-neutral pH.

To generate the data of FIG. 3D whole body counts of radiolabeled 8-18C5 were taken at the indicated times. Counts per minute ("CPM") obtained 24 hours after 8-18C5 administration, immediately prior to Seldeg or control delivery, are taken as 100% for each mouse and CPM of whole body obtained thereafter are normalized to this time point. The error bars indicate standard deviations and statistically significant differences were determined using two-way ANOVA with Tukey's multiple comparisons, with $p<0.05$ and n=6 mice/group.

Doses of 125 μg and 31 μg of MOG-Seldeg are approximately 2 to 8-fold lower (on a molar basis) than a dose of 500 μg, a MST-HN Abdeg, which has been shown to globally eliminate IgG levels in mice. Such lower doses of MOG-Seldeg were used to minimize effects on IgGs that were not specific for the fused antigen through competition with the Seldeg for FcRn binding. The doses of 125 μg or 31 μg represent an approximate 16 and 4-fold molar excess, respectively, over the 8-18C5 target antigen-specific antibody.

FIG. 3D provides a graph of normalized body counts of radiolabeled 8-18C5 (the target antigen-specific antibody) versus time. Administration of MOG-Seldeg resulted in a rapid, dose-dependent decrease in 8-18C5 in normalized whole body counts (FIG. 3D), which demonstrates the ability of MOG-Seldeg to selectively deplete 8-18C5 from the body. In contrast, the injection of control MOG-WT, lacking the FcRn-enhancing MST-HN mutations, had no effect on 8-18C5 antibody depletion. This demonstrates the importance of the MST-HN mutations to confer a high binding affinity for FcRn at pH 6.0-7.4.

Figure 3E:
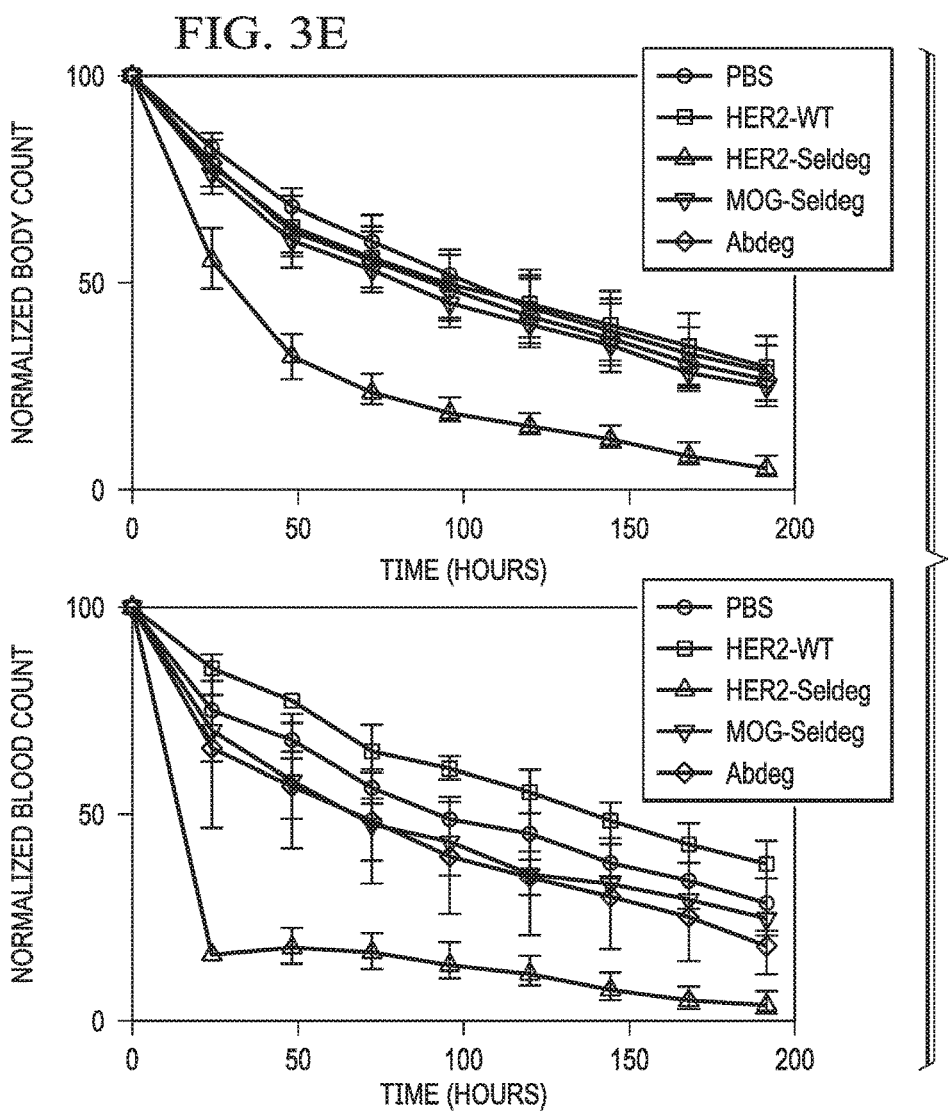
FIG. 3E shows additional graphs reporting exemplary normalized blood and body count versus time, showing clearance of an antigen-specific antibody by an exemplary FcRn-targeting Seldeg.

Example 3—Specificity of Seldegs that Target FcRn and their Ability to Induce a Significant Decrease in Target Antigen-Specific Antibodies Levels, Both in Blood and Throughout the Body To analyze the specificity of Seldegs and their effect on antibodies with different antigen recognition properties, the behavior of the HER2-specific antibody TZB was investigated in the presence of both HER2-Seldeg and MOG-Seldeg (FIG. 3E). To generate the data of FIG. 3E, huFcγR mice were intravenously injected with 15 μg of radiolabeled ($^{125}$I-labeled) TZB and subsequently with a 4-fold molar excess of HER2-Seldeg, or, as a control for antigen specificity, MOG-Seldeg. Additional controls are phosphate-buffered saline ("PBS"), Abdeg and a recombinant fusion protein comprising HER2 fused to an Fc fragment to generate an analogous construct ("HER2-WT") to the HER2-Seldeg, except it lacks the FcRn-enhancing MST-HN mutations that increase binding affinity at near-neutral pH. In contrast to a Seldeg, an "Abdeg" is a human IgG1-derived antibody with the MST-HN mutations that non-selectively depletes antibodies. Such proteins are called Abdegs because they are antibodies that generally cause IgG degradation.

To generate the data of FIG. 3E, the mice were bled and blood and whole body counts were taken at the indicated times. Counts per minute ("CPM") obtained 24-hours after TZB administration, immediately prior to Seldeg or control delivery, are taken as 100% for each mouse and CPM of blood and whole body obtained thereafter are normalized to this time point. The error bars indicate standard deviations and statistically significant differences were determined using two-way ANOVA with Tukey's multiple comparisons, with $p<0.05$ and n=6 mice/group.

FIG. 3E provides graphs of normalized blood and body counts of radiolabeled TZB (the target antigen-specific antibody) versus time. Administration of HER2-Seldeg caused a significant decrease in normalized body counts of TZB, both in blood and whole body counts, which demonstrates the ability of HER2-Seldeg to selectively deplete TZB from the body. In contrast, the control proteins demonstrated similar behavior to that observed for the PBS control (FIG. 3E).

Example 4—Ability, of Seldegs that Target FcRn to Rapidly Deplete Target Antigen-Specific Antibodies Mice were intravenously administered with radiolabeled ($^{125}$I) TZB (15 μg) and 24 hours later HER2-Seldeg (51 μg; four-fold molar excess over TZB) was delivered intravenously. Additional controls are phosphate-buffered saline ("PBS") and Abdeg (60 μg).

Figure 3F:
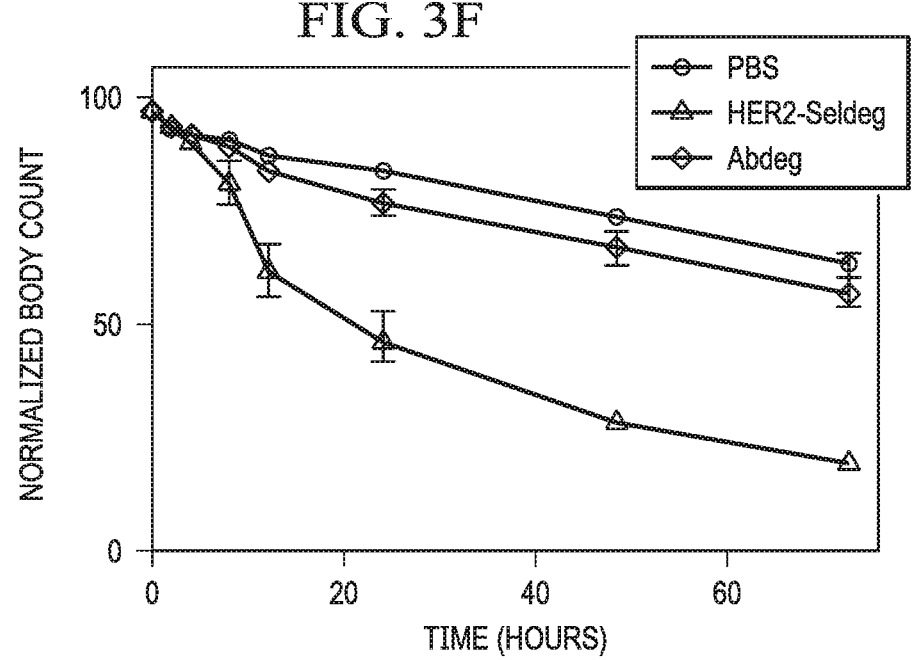
FIG. 3F shows additional graphs reporting exemplary normalized blood and body count versus time, showing clearance of an antigen-specific antibody by an exemplary FcRn-targeting Seldeg.
Figure 3F:
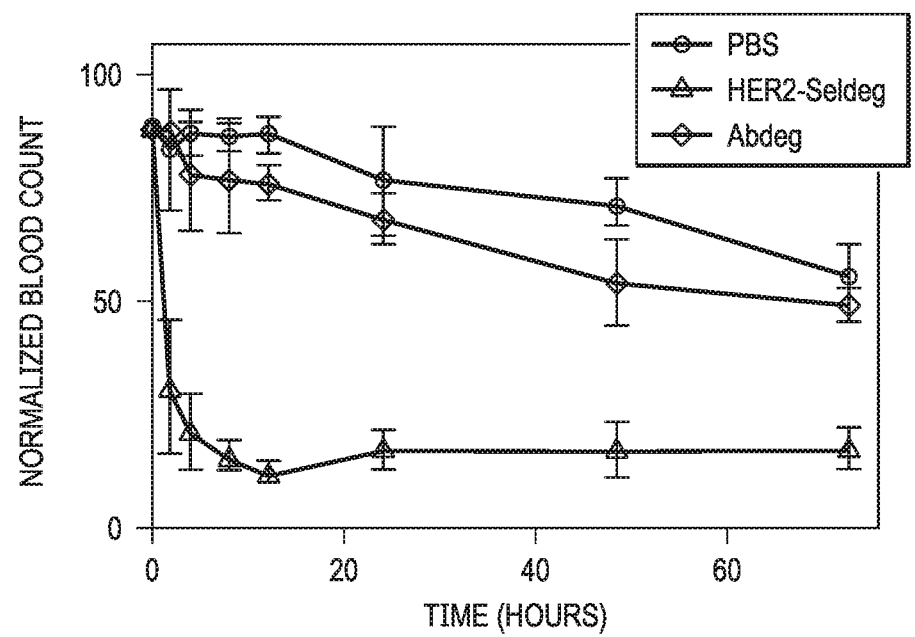

To generate the data of FIG. 3F, the mice were bled and blood and whole body counts were taken at the indicated times. Counts per minute ("CPM") obtained 24-hours after TZB administration, immediately prior to Seldeg or control delivery, are taken as 100% for each mouse and CPM of blood and whole body obtained thereafter are normalized to this time point. The error bars indicate standard deviations and statistically significant differences were determined using two-way ANOVA with Tukey's multiple comparisons, with $p<0.05$ and n=5-6 mice/group.

FIG. 3F provides graphs of normalized blood and body counts of radiolabeled TZB (the target antigen-specific antibody) versus time. Administration of HER2-Seldeg caused a rapid decrease in normalized body and blood counts of TZB, which demonstrates the ability of the HER2-Seldeg to rapidly deplete TZB from the body. Notably, the blood counts of TZB were reduced close to background levels within two hours of Seldeg administration (FIG. 3F), further supporting the ability of the HER2-Seldeg to deplete target antigen-specific antibodies rapidly from the blood. In contrast, at a dose of 60 μg/mouse, delivery of Abdeg resulted in similar behavior to that observed for the PBS control (FIG. 3F).

Example 5—Activity of Seldegs that Target Exposed Phosphatidylserine (PS) on the Cell Surface We also investigated the ability of a Seldeg in which the targeting protein is the C2 domain of synaptotagmin 1 (Syt1) to selectively deplete antibodies specific for MOG in huFcγR mice. Syt1 binds to exposed PS on cells, and the Seldeg is therefore designed MOG-Seldeg-PS and is shown schematically (FIG. 4A). MOG-Seldeg-PS(DN) that does not bind to PS due to the presence of the 'DN' mutations (D173N, D179N, D231N, D233N and D239N) was also generated. MOG-Seldeg-PS and MOG-Seldeg-PS(DN) were purified from culture supernatants of transfected HEK-293F cells using protein G-Sepharose and standard methods Heterodimer formation was achieved by inserting knobs-into-holes and electrostatic steering mutations into the Fc regions, and size exclusion analyses indicate that the recombinant proteins are well behaved (FIG. 4A).

Figure 4B:
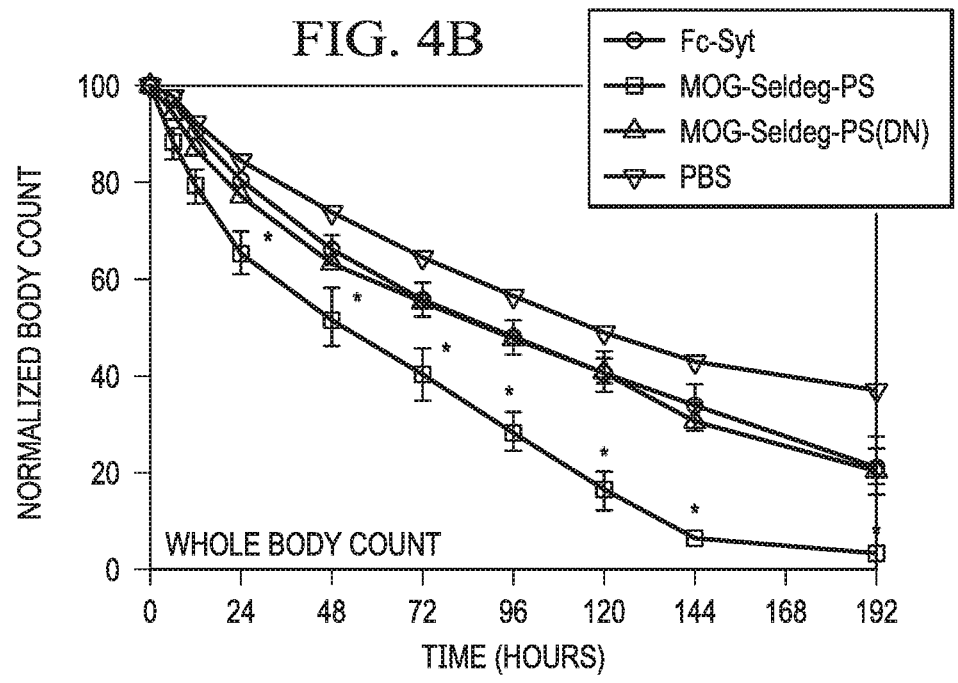
Figure 4B:
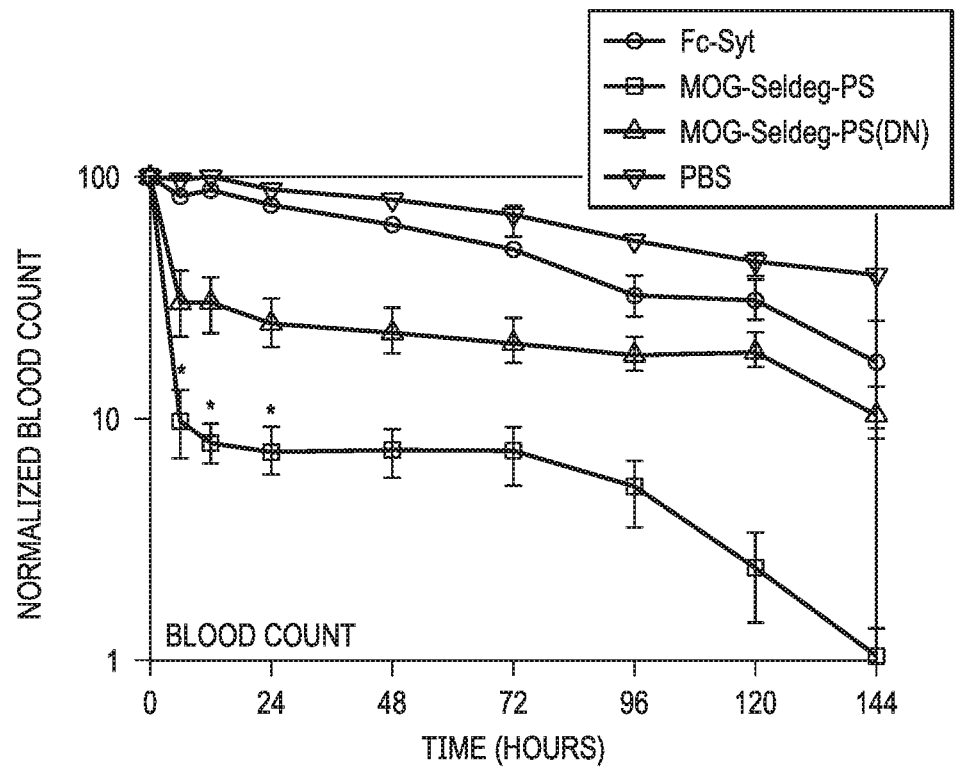
Figure 5A:
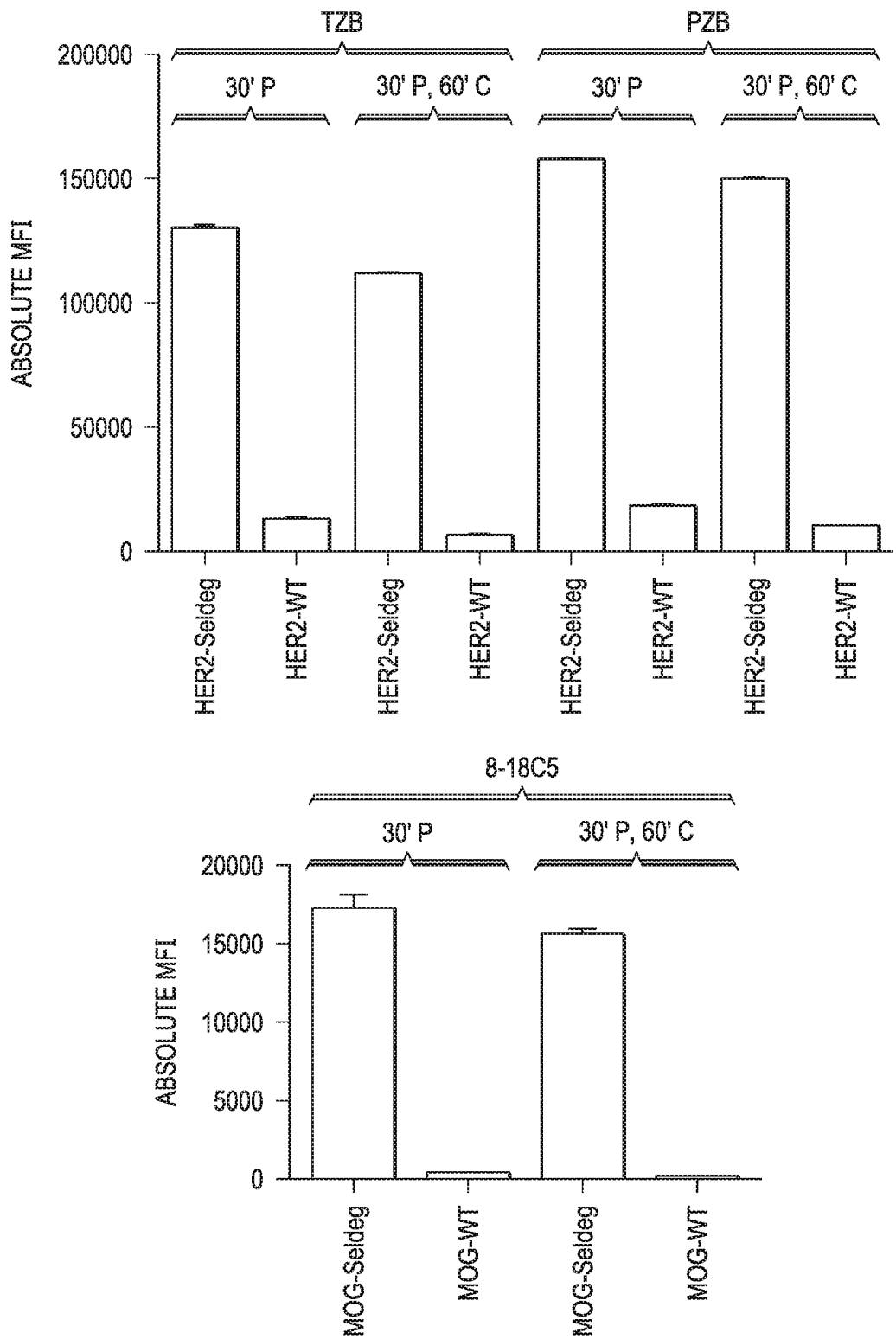
Figure 5B:
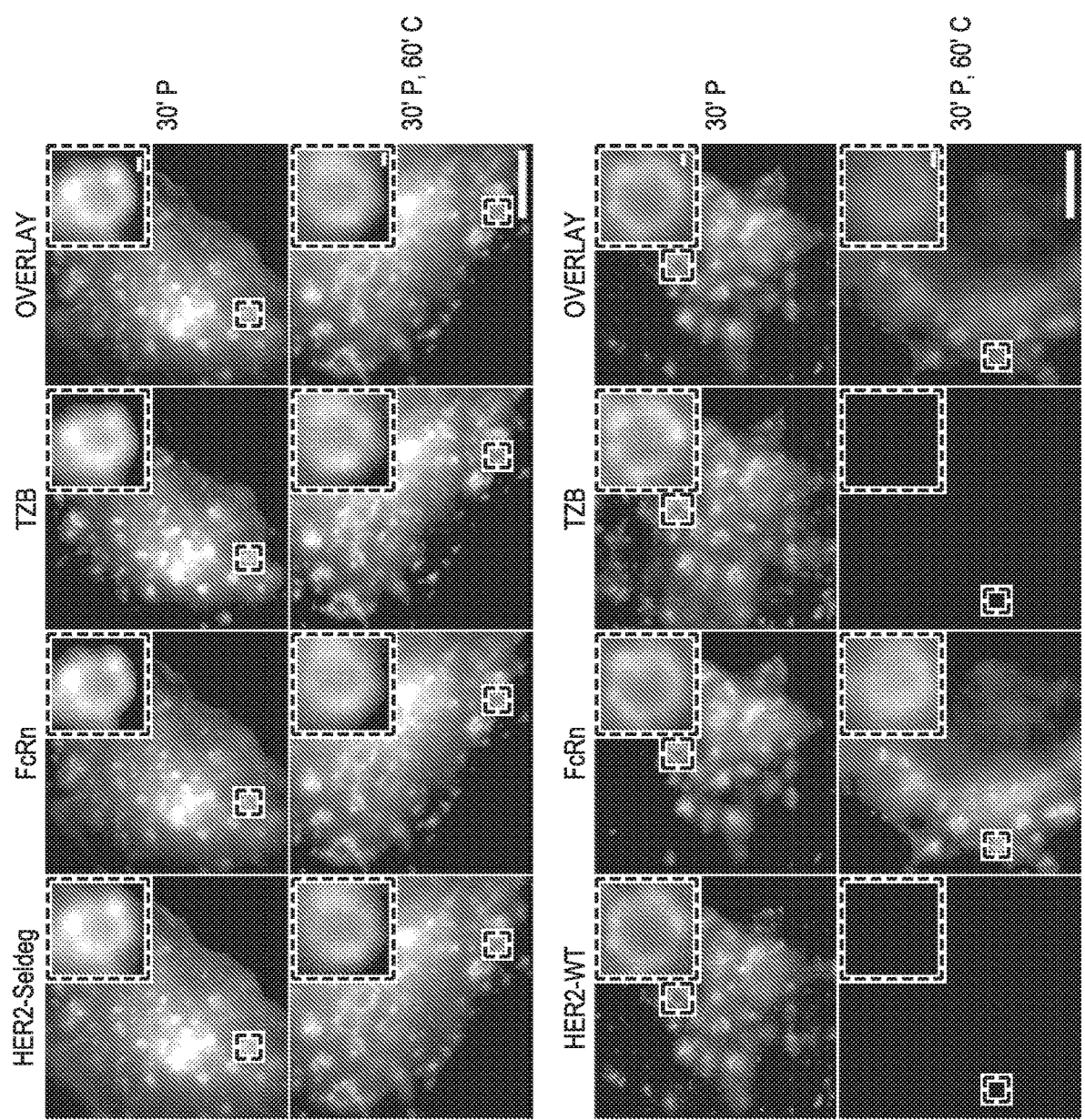
Figure 5C:
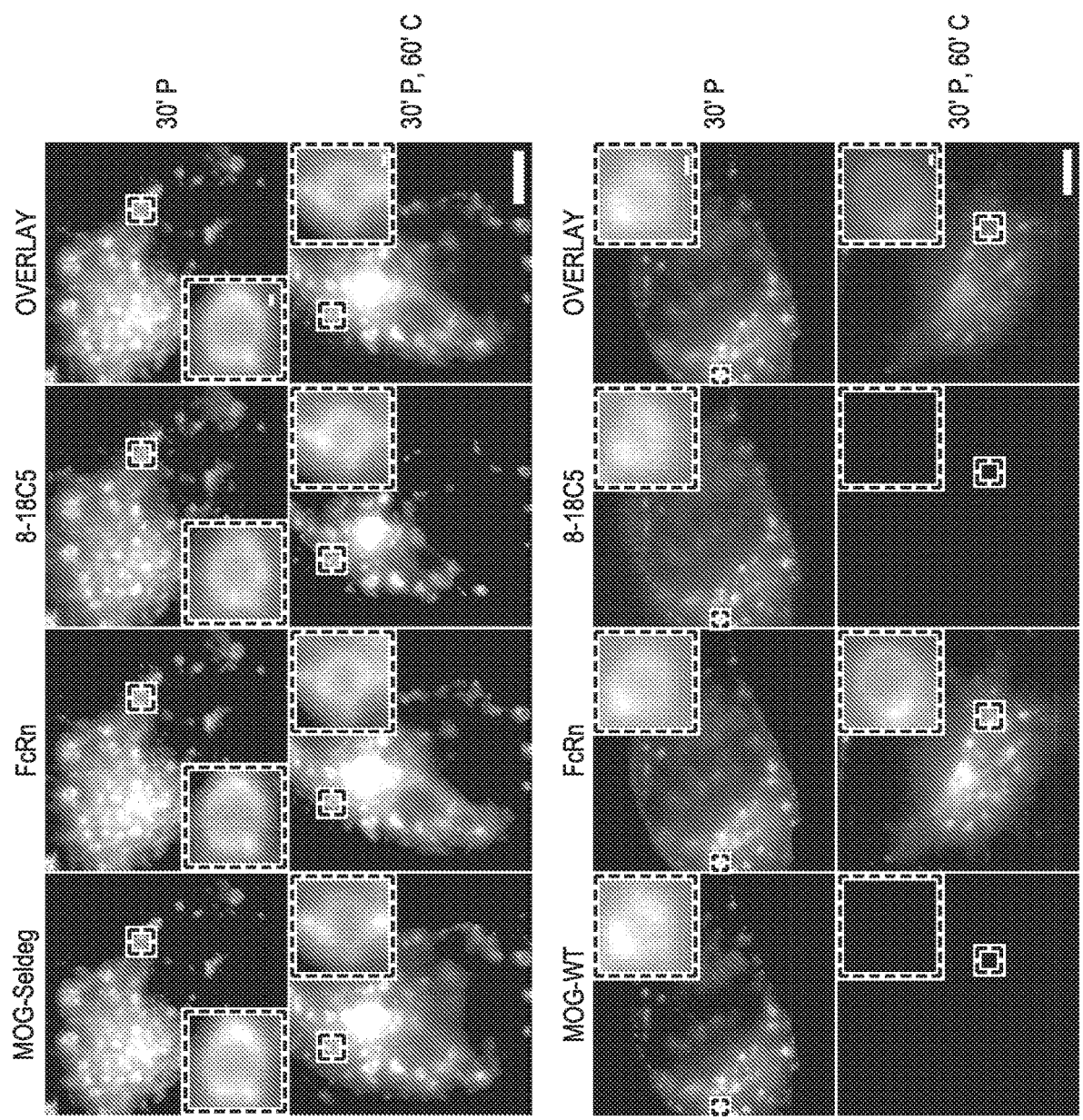
Figure 6A:
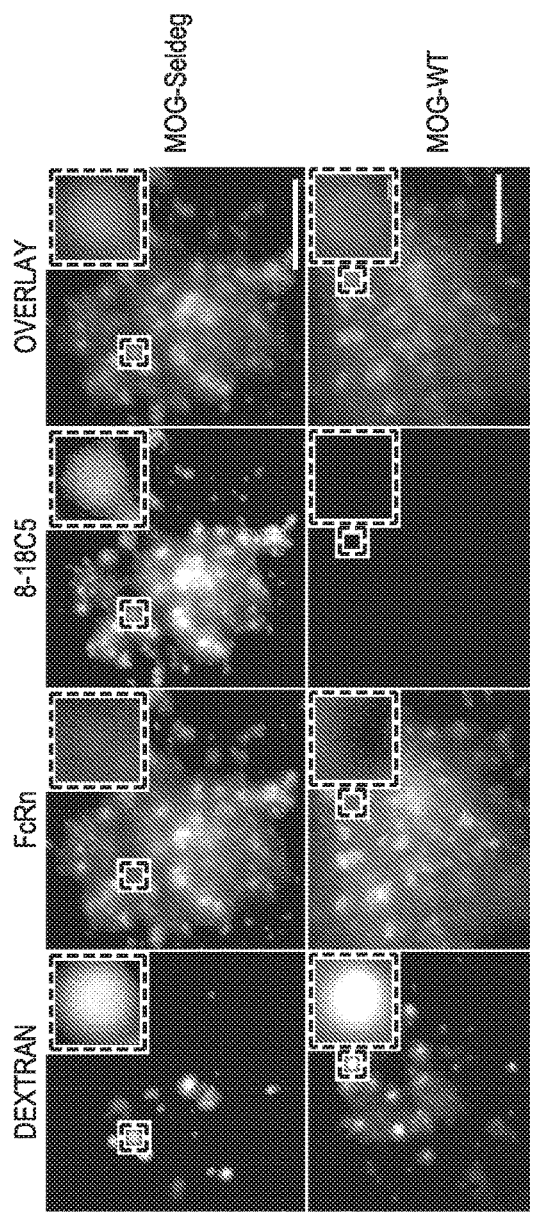
Figure 6B:
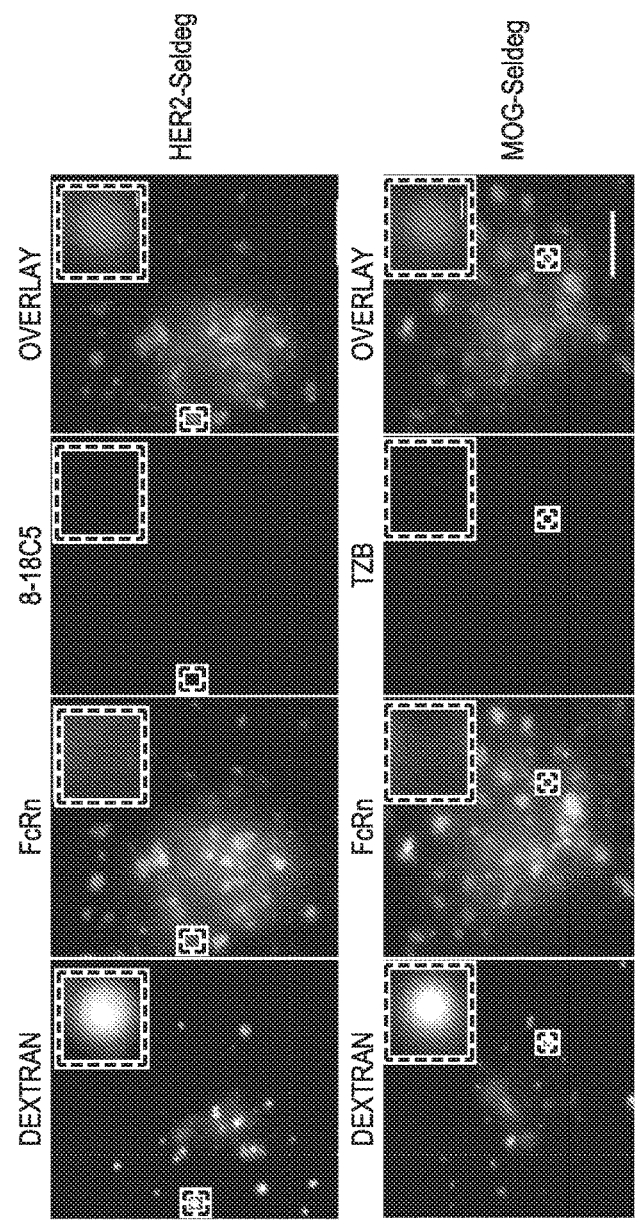
Figure 7:
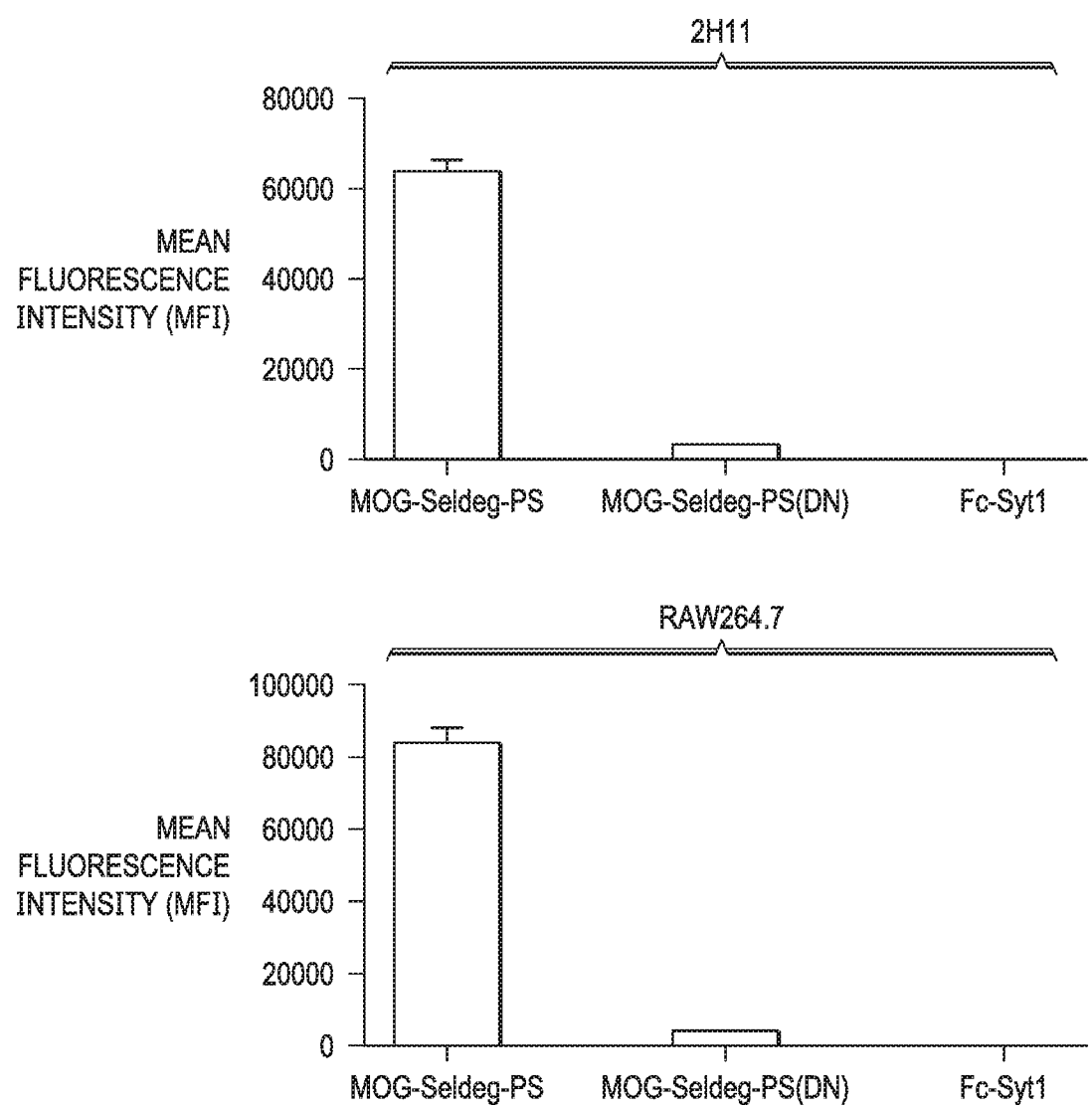

To generate the data shown in FIG. 4B, mice were intravenously injected with radiolabeled ($^{125}$I) chimeric 8-18C5 (human constant/mouse variable domains; MOG-specific; 15-20 µg) and 24 hours later phosphate-buffered saline (PBS), 40 µg MOG-Seldeg-PS or as controls, 34 µg Fc-Syt1 (no MOO attached) or 40 µg MOG-Seldeg-PS(DN) were delivered intravenously. Radioactivity levels were determined at the indicated times Whole body CPM or blood CPM levels obtained immediately prior to MOG-Seldeg-PS or control delivery were taken as 100% and all subsequent CPM that were obtained were normalized against these CPM levels. Error bars indicate the standard error of the mean (SEM) and statistically significant differences between MOG-Seldeg-PS treated group and control groups (Fc-Syt1, MOG-Seldeg-PS(DN) and PBS) are indicated by * ($p<0.05$, two-way ANOVA with Tukey's multiple comparisons; n=5-6 mice/group).

Administration of MOG-Seldeg-PS caused a significant decrease in normalized body counts of 8-18C5, both in blood and whole body counts, which demonstrates the ability of MOG-Seldeg-PS to selectively deplete 8-18C5 from the body, in contrast, the control protein Fc-Syt1 demonstrated similar behavior to that observed for the PBS control, and although MOG-Seldeg-PS(DN) induced a decrease in 8-18C5 (due to residual binding to PS), the effect was much lower than that of MOG-Seldeg-PS (FIG. 4B).

Example 6—Ability of Seldegs that Target FcRn to Efficiently Internalize Target Antigen-Specific Antibodies into Endosomes and Cause Degradation Via Delivery to Lysosomes To determine the mechanism of activity of Seldegs at the cellular level, flow cytometry and fluorescence microscopy were performed to analyze the effects of Seldegs on the internalization and accumulation of target antigen-specific antibodies TZB, PZB and 8-18C5. First, human endothelial cells (HMEC-1) were transfected with a human FcRn-GFP expression construct, which was mutated so that its binding properties are analogous to mouse FcRn.

The Seldegs efficiently internalized bound target antigen-specific antibodies into endosomes within cells, and following 8 hours of incubation, the target antigen-specific antibodies were delivered to lysosomes.

FIG. 5A is a graph of mean fluorescence intensity ("MFI") and FIG. 5B and FIG. 5C are microscopic images of Seldeg activity in the presence of target antigen-specific antibodies, with microscopic images of representative endosomes cropped, expanded, and presented in the top right-corner insets. FIGURE SA shows a greater MFI in the presence of, respectively, Alexa 647-labeled TZB with HER2-Seldeg and Alexa 647-labeled 8-18C5 with MOG-Seldeg. This greater MFI indicates that co-incubation of HER2- and MOG-Seldeg, respectively, with TZB and 8-18C5 (400 nM Seldeg or WT control plus 100 nM antigen-specific antibody; 30 minute pulse, no chase or 60 minute chase, labeled 30' P or 30' P, 60' C, respectively, in FIGS. 5A, 5B and 5C) results in high levels of TZB and 8-18C5 entering cells. Similar results were obtained when the HER2-specific antibody pertuzumab (PZB) was used instead of TZB in the presence of HER2-Seldeg (FIG. 5A). Further, the majority of each target antigen-specific antibody is retained by the cells during a 60 minute chase. In contrast, the accumulation of target antigen-specific antibodies within cells is substantially lower in the presence of negative controls HER2-WT (selective for TZB or PZB) and MOG-WT (selective for 8-18C5).

FIGS. 5B and C show that antigen-specific antibodies accumulate in cells and are associated with FcRn in endosomes in the presence of Seldegs. To generate the microscopic images of FIG. 5B, HMEC-1 cells were pulsed with 100 nM Alexa 647-labeled TZB (HER2-specific) in complex with 400 nM Alexa 555-labeled HER2-Seldeg or HER2-WT (as indicated) for 30 minutes, washed and either immediately fixed, or washed, chased in medium for 60 minutes, followed by fixation. Fixed cells were imaged using fluorescence microscopy. The data in FIG. 5C was generated using the same approach, except that 100 nM Alexa 647-labeled 8-18C5 (MOG-specific) in complex with 400 nM Alexa 555-labeled MOG-Seldeg or MOG-WT was used Bars in each of the microscopic images are 5 μm, and bars in each of the microscopic image insets are 0.25 μm. The data shown in FIGS. 5B and 5C demonstrates that antigen-specific antibodies accumulate to substantially higher levels in FcRn-expressing cells in the presence of Seldegs that bind to FcRn compared with in the presence of control (WT) proteins.

FIG. 6A shows microscopic images of Seldeg activity in the presence of target antigen-specific antibodies, with microscopic images of representative lysosomes cropped, expanded, and presented in the top right-corner insets. For FIG. 6A, HMEC-1 cells were pre-pulsed with Alexa 555-labeled Dextran for 2 hours and washed, and then pulsed with 100 nM Alexa 647-labeled 8-18C5 (MOG-specific) in complex with 400 nM MOG-Seldeg or MOG-WT (as indicated) for 30 minutes, followed by an 8 hour chase and then washed, fixed and imaged. To generate the microscopic images of FIG. 6B, HMEC-1 cells were pre-pulsed with Alexa 555-labeled Dextran for 2 hours and washed, and then pulsed with either 100 nM Alexa 647-labeled TZB or 8-18C5 antibodies, and 400 nM MOG-Seldeg or HER2-Seldeg (as indicated) for 30 minutes followed by an 8 hour chase, and then washed, fixed and imaged. For each overlay image (shown in the right column), GFP, Alexa 555 and Alexa 647 are pseudo-colored green, red and blue, respectively Bars in each of the microscopic images are 5 μm, and bars in each of the microscopic image insets are 0.25 μm Notably, FIG. 6B shows that the cells do not accumulate TZB and 8-18C5 in lysosomes in the presence of MOG-Seldeg or HER2-Seldeg, respectively, which indicates the antigen specificity of their effects.

Example 7—Ability of Seldegs that Target Phosphatidylserine to Efficiently Internalize Target Antigen-Specific Antibodies into Cells FIG. 7 shows that MOG-Seldeg-PS efficiently internalizes MOG-specific antibodies (chimeric 8-18C5) into endothelial cells and macrophages and uptake is dependent on PS-binding Endothelial cells (2H11) or macrophages (RAW264.7) that expose PS were incubated with 10 nM Alexa 647-labeled chimeric 8-18C5 mixed with 20 nM MOG-Seldeg-PS, MOG-Seldeg-PS(DN) or Fc-Syt1 (no MOG) for 2 hours Mean fluorescence intensities (MFI) of Alexa 647-labeled chimeric 8-18C5 (made by fusing the variable domains of the mouse antibody, 8-18C5, to the constant regions of human IgG1, Cκ, using methods well known to those skilled in the art) for triplicate samples were determined by flow cytometry.

This exemplary PS-binding Seldeg is calcium-dependent and therefore dissociates in endosomes where the calcium concentration is much lower. Not all PS-targeting Seldegs are expected to be calcium-dependent, but some, also such as those comprising annexin V will have this property, as would be understood by skilled persons. In addition, several antibodies can bind to beta-2 glycoprotein I that can in turn bind to PS.

Figure 8:
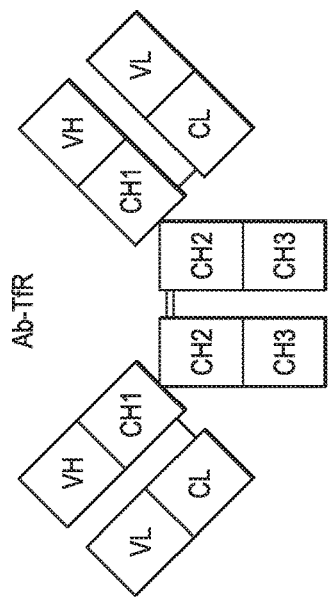
Figure 8:
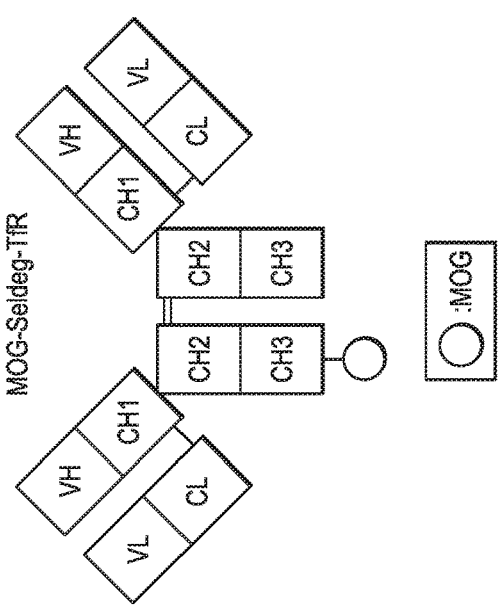
Figure 8:
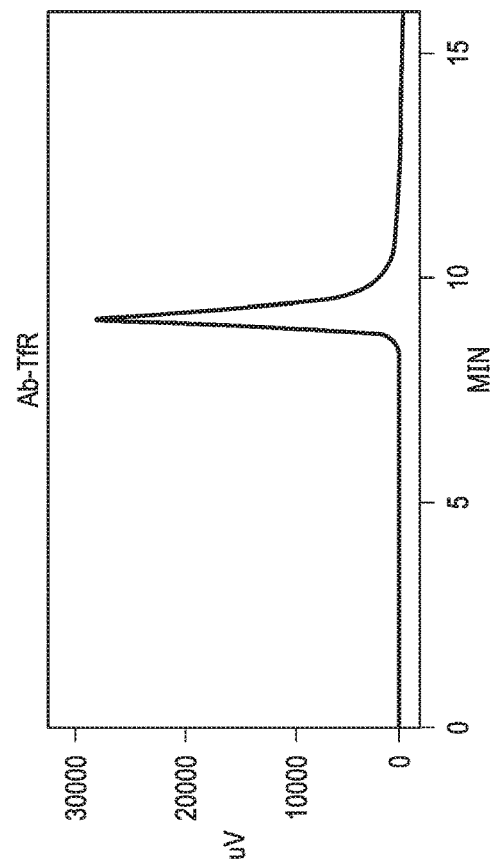
Figure 8:
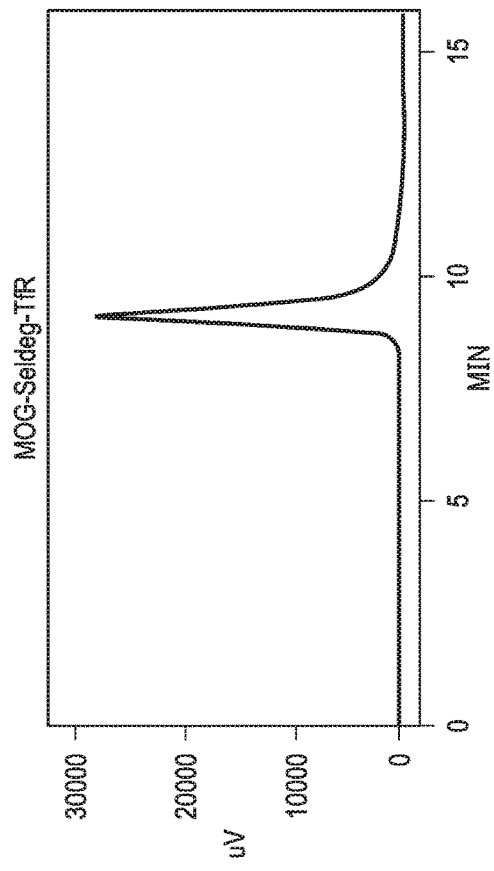
Figure 9:
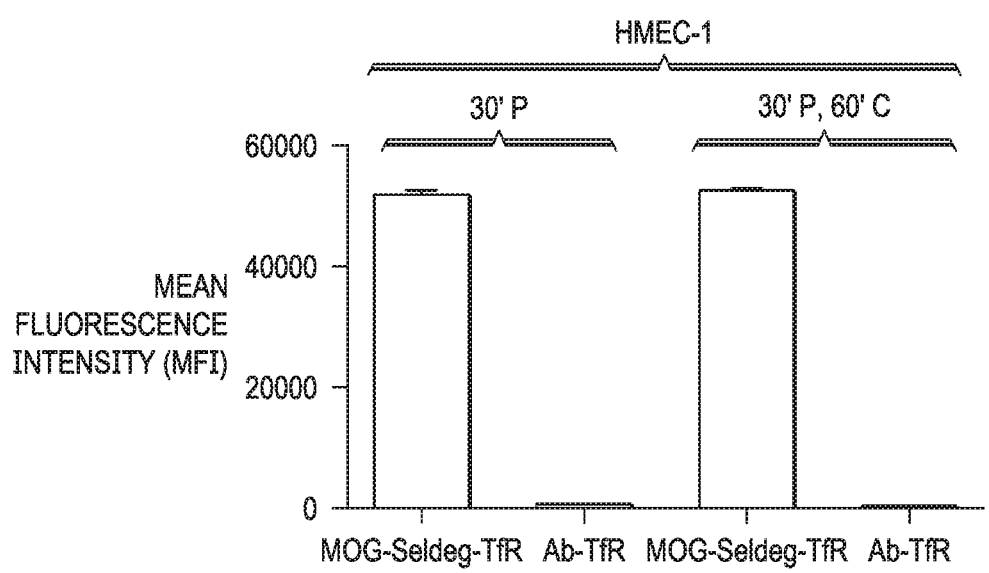
Figure 10A:
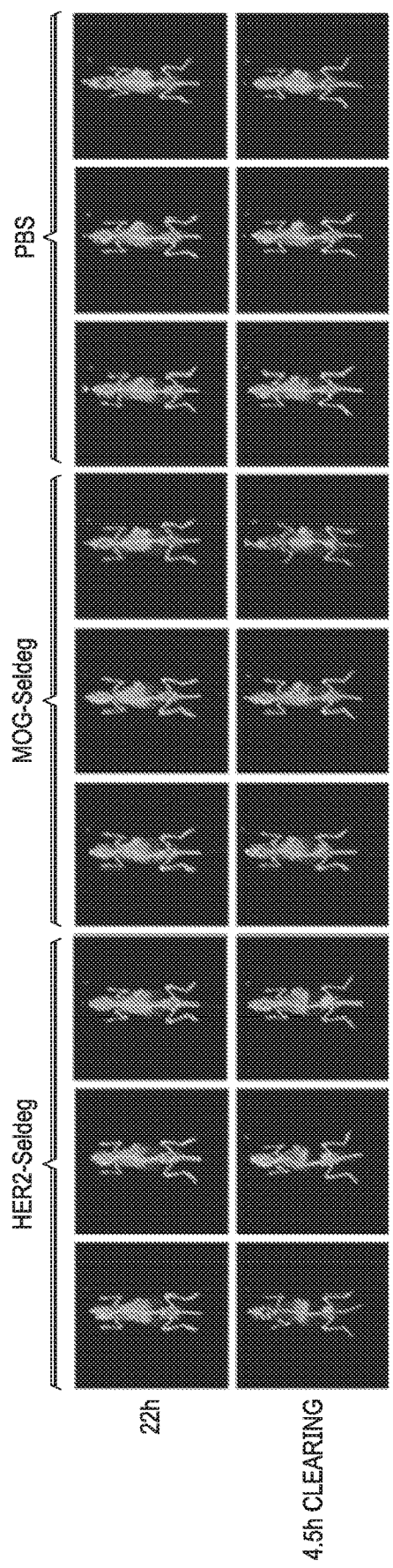
Figure 10B:
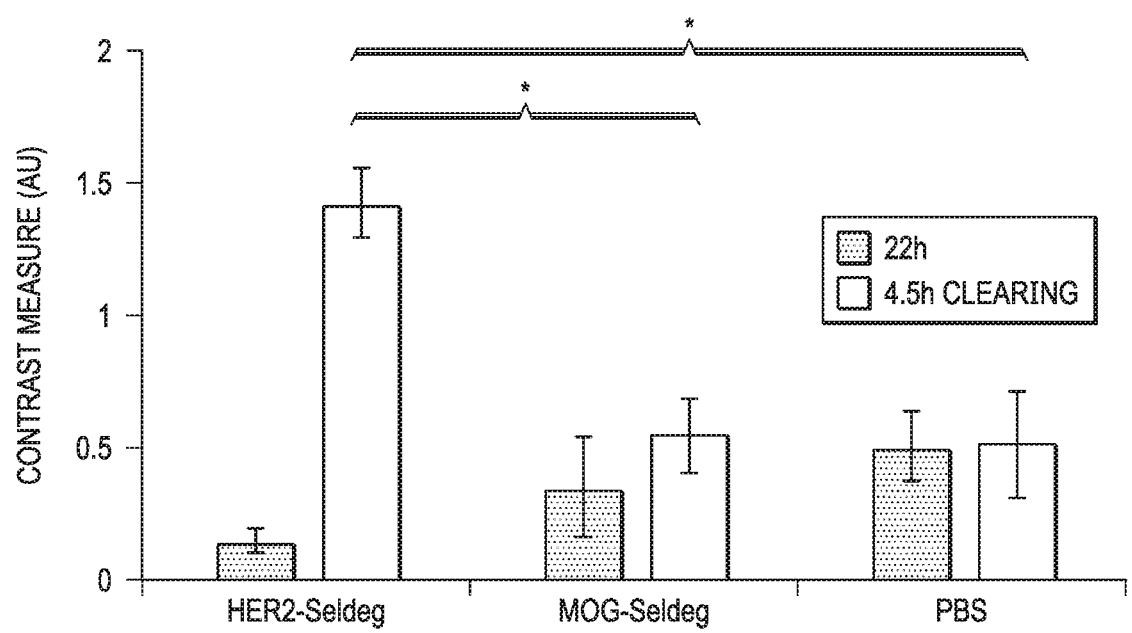

Example 8—Ability of Seldegs that Target the Transferrin Receptor to Efficiently Internalize Target Antigen-Specific Antibodies into Cells Expressing the Human Transferrin Receptor A Seldeg comprising antigen (MOG) fused to an antibody that targets the transferrin receptor (MOG-Seldeg-TfR) has been generated and is shown schematically in FIG. 8. MOG-Seldeg-TfR and control antibody, Ab-TfR (no MOG present), were purified from culture supernatants of transfected HEK-293F cells using protein G-Sepharose and standard methods MOG-Seldeg-TfR efficiently internalizes MOG-specific antibodies (chimeric 8-18C5) into endothelial (HMEC-1) cells and uptake is dependent on the presence of MOG in the Seldeg (FIG. 9). HMEC-1 cells that express human TfR were incubated with 50 nM Alexa 647-labeled chimeric 8-18C5 (specific for MOG) mixed with 200 nM MOG-Seldeg-TfR, or TfR-specific antibody (Ab-TfR; no MOG) for 30 minutes followed by washing and no chase (30'P), or for 30 minutes followed by washing and a 60 minute chase period (30'P, 60'C). Mean fluorescence intensities (MFI) of Alexa 647-labeled 8-18C5 for triplicate samples were determined by flow cytometry (FIG. 9).

Example 9—Ability to Seldegs that Target FcRn to Clear Background During Positron Emission Tomographic Analyses of Tumors Using Radiolabeled Antibodies Fcmale BALB/c SCID mice were implanted in the mammary fat pad ($0.5\times10^6$ cells/mouse; cells were suspended in RPM1-1640/Matrigel prior to injection) with the HER2-positive breast cancer cell line, HCC1954. 6-7 days later, mice were injected with 124-I labeled TZB (60 μg/mouse) and analyzed using positron emission tomography (PET) 22 hours later Mice were injected with a molar equivalent of HER2-Seldeg (51 μg/mouse) or, as controls, MOG-Seldeg (31 μg/mouse) or PBS vehicle (n=3 mice/group). Mice were analyzed using PET 4 hours following injection of the Seldegs or PBS. Imaging of mice was carried out using a Siemens Inveon PET-computed tomography (CT) Multimodality System.

To generate the date shown in FIG. 10A, mice were imaged at 22 hours following injection of 124-I labeled TZB (‘22*h*’) and at 4.5-5 hours post-injection (‘4.5*h* clearing’) of HER2-Seldeg, MOG-Seldeg or PBS. PET and CT images were co-registered in the AMIDE software package. FIG. 10B provides graphs of contrast measures for radiolabel intensity for 22 hours post-injection of 124-I labeled TZB and 4.5-5 hours post-injection of HER2-Seldeg, MOG-Seldeg or PBS. To determine contrast measures, two regions of interest were identified in the thoracic region (background) and tumor. The mean values (n=3 mice/group) for the ratios of mean intensity in the tumor to mean intensity in the thoracic regions are plotted. Error bars indicate standard errors. Statistically significant differences ($p<0.05$) between mice treated with HER2-Seldeg vs. MOG-Seldeg or PBS are shown. The data show that delivery of HER2-Seldeg reduces the background in the thoracic region of the mice.

Example 10 DNA and Proteins Sequences of Exemplary Seldegs and Controls and Variants Thereof Having Mutations Such as Knobs-into-Holes Mutations, Arginine Mutations and Electrostatic Steering Mutations Table 1 shows DNA sequences of polynucleotides encoding exemplary proteins described herein, and Table 2 shows amino acid sequences of exemplary proteins encoded by the polynucleotides shown in Table 1, wherein the DNA sequence of SEQ ID NO: 1 encodes the protein of SEQ ID NO: 2, the DNA sequence of SEQ ID NO: 3 encodes the protein of SEQ ID NO: 4, the DNA sequence of SEQ ID NO: 5 encodes the protein of SEQ ID NO: 6, the DNA sequence of SEQ ID NO: 7 encodes the protein of SEQ ID NO: 8, the DNA sequence of SEQ ID NO: 9 encodes the protein of SEQ ID NO: 10, the DNA sequence of SEQ ID NO: 11 encodes the protein of SEQ ID NO: 12, the DNA sequence of SEQ ID NO: 13 encodes the protein of SEQ ID NO: 14, the DNA sequence of SEQ ID NO: 15 encodes the protein of SEQ ID NO: 16, the DNA sequence of SEQ ID NO: 17 encodes the protein of SEQ ID NO: 18, the DNA sequence of SEQ ID NO: 19 encodes the protein of SEQ ID NO: 20, the DNA sequence of SEQ ID NO: 21 encodes the protein of SEQ ID NO: 22, the DNA sequence of SEQ ID NO: 23 encodes the protein of SEQ ID NO: 24, the DNA sequence of SEQ ID NO: 25 encodes the protein of SEQ ID NO: 26, the DNA sequence of SEQ ID NO: 27 encodes the protein of SEQ ID NO: 28, the DNA sequence of SEQ ID NO: 29 encodes the protein of SEQ ID NO: 30, the DNA sequence of SEQ ID NO: 31 encodes the protein of SEQ ID NO: 32, the DNA sequence of SEQ ID NO: 33 encodes the protein of SEQ ID NO: 34.

TABLE 1

DNA sequences of polynucleotides encoding exemplary proteins.

| Polynucleotide encoding protein | DNA sequence | SEQ ID NO: |
|---|---|---|
| MOG-Seldeg with MST-HN, knobs-into-holes and arginine mutations | GGACAATTCAGAGTGATAGGACCAGGGTATCCCATCCGG<br>GCTTTAGTTGGGGATGAAGCAGAGCTGCCGTGCCGCATC<br>TCTCCTGGGAAAAATGCCACGGGCATGGAGGTGGGTTGG<br>TACCGTTCTCCCTTCTCAAGAGTGGTTCACCTCTACCGAA<br>ATGGCAAGGACCAAGATGCAGAGCAAGCACCTGAATACC<br>GGGGACGCACAGAGCTTCTGAAAGAGACTATCAGTGAGG<br>GAAAGGTTACCCTTAGGATTCAGAACGTGAGATTCTCAG | 1 |

TABLE 1-continued DNA sequences of polynucleotides encoding exemplary proteins.

| Polynucleotide encoding protein | DNA sequence | SEQ ID NO: |
|---|---|---|
| | ATGAAGGAGGCTACACCTGCTTCTTCAGAGACCACTCTTA CCAAGAAGAGGCAGCAATGGAGTTGAAAGTGGAAGATG GAGGCGGTGGATCAGTTGAGCCCAAATCTTCTGACAAAA CTCACACATGCCCACCGTGCCCAGCACCTGAACTCCTGA GGGGACCGTCAGTCTTCCTCTTCCCCCCAAAACCCAAGGA CACCCTCTACATCACTCGGGAACCTGAGGTCACATGCGTG GTGGTGGACGTGAGCCACGAAGACCCTGAGGTCAAGTTC AACTGGTACGTGGACGGCGTGGAGGTGCATAATGCCAAG ACAAAGCCGCGGGAGGAGCAGTACAACAGCACGTACCGT GTGGTCAGCGTCCTCACCGTCCTGCACCAGGACTGGCTGA ATGGCAAGGAGTACAAGTGCAAGGTCTCCAACAAAGCCC GCCCAGCCCCCATCGAGAAAACCATCTCCAAAGCCAAAG GGCAGCCCCGAGAACCACAGGTGACCACCCTGCCCCCAT CCCGGGATGAGCTGACCAAGAACCAGGTCAGCCTGACCT GCCTGGTCAAAGGCTTCTATCCCAGCGACATCGCCGTGG AGTGGGAGAGCAATGGGCAGCCGGAGAACAACTACAAG ACCTTCCCTCCCGTGCTGGACTCCGACGGCTCCTTCTTCCT CTACAGCAAGCTCACCGTGGACAAGAGCAGGTGGCAGCA GGGGAACGTCTTCTCATGCTCTGTGATGCATGAGGCTCTG AAATTCCACTACACGCAGAAGAGCCTCTCCCTGTCTCCGG GTAAA | |
| HER2-Seldeg with MST-HN, knobs-into-holes and arginine mutations | ACCCAAGTGTGCACCGGCACAGACATGAAGCTGCGGCTC CCTGCCAGTCCCGAGACCCACCTGGACATGCTCCGCCAC CTCTACCAGGGCTGCCAGGTGGTGCAGGGAAACCTGGAA CTCACCTACCTGCCCACCAATGCCAGCCTGTCCTTCCTGC AGGATATCCAGGAGGTGCAGGGCTACGTGCTCATCGCTC ACAACCAAGTGAGGCAGGTCCCACTGCAGAGGCTGCGGA TTGTGCGAGGCACCCAGCTCTTTGAGGACAACTATGCCCT GGCCGTGCTAGACAATGGAGACCCGCTGAACAATACCAC CCCTGTCACAGGGGCCTCCCCAGGAGGCCTGCGGGAGCT GCAGCTTCGAAGCCTCACAGAGATCTTGAAAGGAGGGGT CTTGATCCAGCGGAACCCCCAGCTCTGCTACCAGGACAC GATTTTGTGGAAGGACATCTTCCACAAGAACAACCAGCT GGCTCTCACACTGATAGACACCAACCGCTCTCGGGCCTGC CACCCCTGTTCTCCGATGTGTAAGGGCTCCCGCTGCTGGG GAGAGAGTTCTGAGGATTGTCAGAGCCTGACGCGCACTG TCTGTGCCGGTGGCTGTGCCCGCTGCAAGGGGCCACTGCC CACTGACTGCTGCCATGAGCAGTGTGCTGCCGGCTGCAC GGGCCCCAAGCACTCTGACTGCCTGGCCTGCCTCCACTTC AACCACAGTGGCATCTGTGAGCTGCACTGCCCAGCCCTG GTCACCTACAACACAGACACGTTTGAGTCCATGCCCAATC CCGAGGGCCGGTATACATTCGGCGCCAGCTGTGTGACTG CCTGTCCCTACAACTACCTTTCTACGGACGTGGGATCCTG CACCCTCGTCTGCCCCCTGCACAACCAAGAGGTGACAGC AGAGGATGGAACACAGCGGTGTGAGAAGTGCAGCAAGC CCTGTGCCCGAGTGTGCTATGGTCTGGGCATGGAGCACTT GCGAGAGGTGAGGGCAGTTACCAGTGCCAATATCCAGGA GTTTGCTGGCTGCAAGAAGATCTTTGGGAGCCTGGCATTT CTGCCGGAGAGCTTTGATGGGGACCCAGCCTCCAACACT GCCCCGCTCCAGCCAGAGCAGCTCCAAGTGTTTGAGACT CTGGAAGAGATCACAGGTTACCTATACATCTCAGCATGG CCGGACAGCCTGCCTGACCTCAGCGTCTTCCAGAACCTGC AAGTAATCCGGGGACGAATTCTGCACAATGGCGCCTACT CGCTGACCCTGCAAGGGCTGGGCATCAGCTGGCTGGGGC TGCGCTCACTGAGGGAACTGGGCAGTGGACTGGCCCTCA TCCACCATAACACCCACCTCTGCTTCGTGCACACGGTGCC CTGGGACCAGCTCTTTCGGAACCCGCACCAAGCTCTGCTC CACACTGCCAACCGGCCAGAGGACGAGTGTGTGGGCGAG GGCCTGGCCTGCCACCAGCTGTGCGCCCGAGGGCACTGC TGGGGTCCAGGGCCCACCCAGTGTGTCAACTGCAGCCAG TTCCTTCGGGGCCAGGAGTGCGTGGAGGAATGCCGAGTA CTGCAGGGGCTCCCCAGGGAGTATGTGAATGCCAGGCAC TGTTTGCCGTGCCACCCTGAGTGTCAGCCCCAGAATGGCT CAGTGACCTGTTTTGGACCGGAGGCTGACCAGTGTGTGG CCTGTGCCCACTATAAGGACCCTCCCTTCTGCGTGGCCCG CTGCCCCAGCGGTGTGAAACCTGACCTCTCCTACATGCCC ATCTGGAAGTTTCCAGATGAGGAGGGCGCATGCCAGCCT TGCCCCATCAACTGCACCCACTCCTGTGTGGACCTGGATG ACAAGGGCTGCCCCGCCGAGCAGAGAGCCAGCCCTCTGA CGATTGAAGGCCGCATGGATCCCAAATCTTCTGACAAAA CTCACACATGCCCACCGTGCCCAGCACCTGAACTCCTGA GGGGACCGTCAGTCTTCCTCTTCCCCCCAAAACCCAAGGA CACCCTCTACATCACTCGGGAACCTGAGGTCACATGCGTG | 3 |

TABLE 1-continued

DNA sequences of polynucleotides encoding exemplary proteins.

| Polynucleotide encoding protein | DNA sequence | SEQ ID NO: |
|---|---|---|
| | GTGGTGGACGTGAGCCACGAAGACCCTGAGGTCAAGTTC AACTGGTACGTGGACGGCGTGGAGGTGCATAATGCCAAG ACAAAGCCGCGGGAGGAGCAGTACAACAGCACGTACCGT GTGGTCAGCGTCCTCACCGTCCTGCACCAGGACTGGCTGA ATGGCAAGGAGTACAAGTGCAAGGTCTCCAACAAAGCCC GCCCAGCCCCCATCGAGAAAACCATCTCCAAAGCCAAAG GGCAGCCCCGAGAACCACAGGTGACCACCCTGCCCCCAT CCCGGGATGAGCTGACCAAGAACCAGGTCAGCCTGACCT GCCTGGTCAAAGGCTTCTATCCCAGCGACATCGCCGTGG AGTGGGAGAGCAATGGGCAGCCGGAGAACAACTACAAG ACCTTCCCTCCCGTGCTGGACTCCGACGGCTCCTTCTTCCT CTACAGCAAGCTCACCGTGGACAAGAGCAGGTGGCAGCA GGGGAACGTCTTCTCATGCTCTGTGATGCATGAGGCTCTG AAATTCCACTACACGCAGAAGAGCCTCTCCCTGTCTCCTG GTAAA | |
| Fc with MST-HN, knobs-into-holes and arginine mutations | GTTGAGCCCAAATCTTCTGACAAAACTCACACATGCCCAC CGTGCCCAGCACCTGAACTCCTGAGGGGACCGTCAGTCTT CCTCTTCCCCCCAAAACCCAAGGACACCCTCTACATCACT CGGGAACCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCGCCCAGCCCCCAT CGAGAAAACCATCTCCAAAGCCAAAGGGCAGCCCCGAGA ACCACAGGTGTACACCCTGCCCCCATCCCGGGATGAGCT GACCAAGAACCAGGTCCACCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGGACTCCGACGGCTCCTTCGCCCTCTACAGCAAGCTC ACCGTGGACAAGAGCAGGTGGCAGCAGGGGAACGTCTTC TCATGCTCCGTGATGCATGAGGCTCTGAAATTCCACTACA CGCAGAAGAGCCTCTCCCTGTCTCCGGGTAAA | 5 |
| MOG-Seldeg-PS with knobs-into-holes and arginine mutations | GGACAATTCAGAGTGATAGGACCAGGGTATCCCATCCGG GCTTTAGTTGGGGATGAAGCAGAGCTGCCGTGCCGCATC TCTCCTGGGAAAAATGCCACGGGCATGGAGGTGGGTTGG TACCGTTCTCCCTTCTCAAGAGTGGTTCACCTCTACCGAA ATGGCAAGGACCAAGATGCAGAGCAAGCACCTGAATACC GGGGACGCACAGAGCTTCTGAAAGAGACTATCAGTGAGG GAAAGGTTACCCTTAGGATTCAGAACGTGAGATTCTCAG ATGAAGGAGGCTACACCTGCTTCTTCAGAGACCACTCTTA CCAAGAAGAGGCAGCAATGGAGTTGAAAGTGGAAGATG GAGGCGGTGGATCAGTTGAGCCCAAATCTTCTGACAAAA CTCACACATGCCCACCGTGCCCAGCACCTGAACTCCTGA GGGGACCGTCAGTCTTCCTCTTCCCCCCAAAACCCAAGGA CACCCTCATGATCTCCCGGACCCCTGAGGTCACATGCGTG GTGGTGGACGTGAGCCACGAAGACCCTGAGGTCAAGTTC AACTGGTACGTGGACGGCGTGGAGGTGCATAATGCCAAG ACAAAGCCGCGGGAGGAGCAGTACAACAGCACGTACCGT GTGGTCAGCGTCCTCACCGTCCTGCACCAGGACTGGCTGA ATGGCAAGGAGTACAAGTGCAAGGTCTCCAACAAAGCCC GCCCAGCCCCCATCGAGAAAACCATCTCCAAAGCCAAAG GCAGCCCCGAGAACCACAGGTGACCACCCTGCCCCCAT CCCGGGATGAGCTGACCAAGAACCAGGTCAGCCTGACCT GCCTGGTCAAAGGCTTCTATCCCAGCGACATCGCCGTGG AGTGGGAGAGCAATGGGCAGCCGGAGAACAACTACAAG ACCTTCCCTCCCGTGCTGGACTCCGACGGCTCCTTCTTCCT CTACAGCAAGCTCACCGTGGACAAGAGCAGGTGGCAGCA GGGGAACGTCTTCTCATGCTCTGTGATGCATGAGGCTCTG CATAACCACTACACGCAGAAGAGCCTCTCCCTGTCTCCGG GTAAAGGAGGCGGTGGATCAGAGAAACTGGGAAACTTC AGTATTCACTGGATTATGATTTCCAAAATAACCAGCTGCT GGTAGGGATCATTCAGGCTGCCGAACTGCCCGCCTTGGA CATGGGGGGCACATCTGATCCTTACGTGAAAGTGTTTCTG CTACCTGATAAGAAGAAGAAATTTGAGACAAAAGTCCAC CGAAAAACCCTTAATCCTGTCTTCAATGAGCAATTTACTT TCAAGGTACCATACTCGGAATTGGGTGGCAAAACCCTAG TGATGGCTGTATATGATTTTGATCGTTTCTCTAAGCATGA CATCATTGGAGAATTTAAAGTCCCTATGAACACAGTGGA TTTTGGCCATGTAACTGAGGAATGGCGTGACCTGCAAAG TGCT | 7 |

TABLE 1-continued

DNA sequences of polynucleotides encoding exemplary proteins.

| Polynucleotide encoding protein | DNA sequence | SEQ ID NO: |
|---|---|---|
| Fc-Syt1 with knobs-into-holes and arginine mutations | GTTGAGCCCAAATCTTCTGACAAAACTCACACATGCCCAC CGTGCCCAGCACCTGAACTCCTGAGGGGACCGTCAGTCTT CCTCTTCCCCCCAAAACCCAAGGACACCCTCATGATCTCC CGGACCCCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCGCCCAGCCCCCAT CGAGAAAACCATCTCCAAAGCCAAAGGGCAGCCCCGAGA ACCACAGGTGTACACCCTGCCCCCATCCCGGGATGAGCT GACCAAGAACCAGGTCCACCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGGACTCCGACGGCTCCTTCGCCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAAGGAGGCG GTGGATCAGAGAAACTGGGAAAACTTCAGTATTCACTGG ATTATGATTTCCAAAATAACCAGCTGCTGGTAGGGATCAT TCAGGCTGCCGAACTGCCCGCCTTGGACATGGGGGGCAC ATCTGATCCTTACGTGAAAGTGTTTCTGCTACCTGATAAG AAGAAGAAATTTGAGACAAAAGTCCACCGAAAAACCCTT AATCCTGTCTTCAATGAGCAATTTACTTTCAAGGTACCAT ACTCGGAATTGGGTGGCAAAACCCTAGTGATGGCTGTAT ATGATTTTGATCGTTTCTCTAAGCATGACATCATTGGAGA ATTTAAAGTCCCTATGAACACAGTGGATTTTGGCCATGTA ACTGAGGAATGGCGTGACCTGCAAAGTGCT | 9 |
| MOG-Seldeg-PS with knobs-into-holes, electrostatic steering and arginine mutations | GGACAATTCAGAGTGATAGGACCAGGGTATCCCATCCGG GCTTTAGTTGGGGATGAAGCAGAGCTGCCGTGCCGCATC TCTCCTGGGAAAAATGCCACGGGCATGGAGGTGGGTTGG TACCGTTCTCCCTTCTCAAGAGTGGTTCACCTCTACCGAA ATGGCAAGGACCAAGATGCAGAGCAAGCACCTGAATACC GGGGACGCACAGAGCTTCTGAAAGAGACTATCAGTGAGG GAAAGGTTACCCTTAGGATTCAGAACGTGAGATTCTCAG ATGAAGGAGGCTACACCTGCTTCTTCAGAGACCACTCTTA CCAAGAAGAGGCAGCAATGGAGTTGAAAGTGGAAGATG GAGGCGGTGGATCAGTTGAGCCCAAATCTTCTGACAAAA CTCACACATGCCCACCGTGCCCAGCACCTGAACTCCTGA GGGGACCGTCAGTCTTCCTCTTCCCCCCAAAACCCAAGGA CACCCTCATGATCTCCCGGACCCCTGAGGTCACATGCGTG GTGGTGGACGTGAGCCACGAAGACCCTGAGGTCAAGTTC AACTGGTACGTGGACGGCGTGGAGGTGCATAATGCCAAG ACAAAGCCGCGGGAGGAGCAGTACAACAGCACGTACCGT GTGGTCAGCGTCCTCACCGTCCTGCACCAGGACTGGCTGA ATGGCAAGGAGTACAAGTGCAAGGTCTCCAACAAAGCCC GCCCAGCCCCCATCGAGAAAACCATCTCCAAAGCCAAAG GGCAGCCCCGAGAACCACAGGTGACCACCCTGCCCCCAT CCCGGGATGAGCTGACCAAGAACCAGGTCAGCCTGACCT GCCTGGTCAAAGGCTTCTATCCCAGCGACATCGCCGTGG AGTGGGAGAGCAATGGGCAGCCGGAGAACAACTACGAC ACCTTCCCTCCCGTGCTGGACTCCGACGGCTCCTTCTTCCT CTACAGCGACCTCACCGTGGACAAGAGCAGGTGGCAGCA GGGGAACGTCTTCTCATGCTCTGTGATGCATGAGGCTCTG CATAACCACTACACGCAGAAGAGCCTCTCCCTGTCTCCGG GTAAAGGAGGCGGTGGATCAGAGAAACTGGGAAAACTTC AGTATTCACTGGATTATGATTTCCAAAATAACCAGCTGCT GGTAGGGATCATTCAGGCTGCCGAACTGCCCGCCTTGGA CATGGGGGCACATCTGATCCTTACGTGAAAGTGTTTCTG CTACCTGATAAGAAGAAGAAATTTGAGACAAAAGTCCAC CGAAAAACCCTTAATCCTGTCTTCAATGAGCAATTTACTT TCAAGGTACCATACTCGGAATTGGGTGGCAAAACCCTAG TGATGGCTGTATATGATTTTGATCGTTTCTCTAAGCATGA CATCATTGGAGAATTTAAAGTCCCTATGAACACAGTGGA TTTTGGCCATGTAACTGAGGAATGGCGTGACCTGCAAAG TGCT | 11 |

TABLE 1-continued

DNA sequences of polynucleotides encoding exemplary proteins.

| Polynucleotide encoding protein | DNA sequence | SEQ ID NO: |
|---|---|---|
| Fc-Syt1 with knobs-into-holes, electrostatic steering and arginine mutations | GTTGAGCCCAAATCTTCTGACAAAACTCACACATGCCCAC CGTGCCCAGCACCTGAACTCCTGAGGGGACCGTCAGTCTT CCTCTTCCCCCCAAAACCCAAGGACACCCTCATGATCTCC CGGACCCCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCGCCCAGCCCCCAT CGAGAAAACCATCTCCAAAGCCAAAGGGCAGCCCCGAGA ACCACAGGTGTACACCCTGCCCCCATCCCGGGATAAGCT GACCAAGAACCAGGTCCACCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGAAGTCCGACGGCTCCTTCGCCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAAGGAGGCG GTGGATCAGAGAAACTGGGAAAACTTCAGTATTCACTGG ATTATGATTTCCAAAATAACCAGCTGCTGGTAGGGATCAT TCAGGCTGCCGAACTGCCCGCCTTGGACATGGGGGGCAC ATCTGATCCTTACGTGAAAGTGTTTCTGCTACCTGATAAG AAGAAGAAATTTGAGACAAAAGTCCACCGAAAAACCCTT AATCCTGTCTTCAATGAGCAATTTACTTTCAAGGTACCAT ACTCGGAATTGGGTGGCAAAACCCTAGTGATGGCTGTAT ATGATTTTGATCGTTTCTCTAAGCATGACATCATTGGAGA ATTTAAAGTCCCTATGAACACAGTGGATTTTGGCCATGTA ACTGAGGAATGGCGTGACCTGCAAAGTGCT | 13 |
| MOG-Seldeg-TfR with knobs-into-holes mutations | GAGGTGCAGCTGGTGCAGTCCGGCGCCGAGGTGAAGAAG CCCGGCGCCTCCGTGAAGGTGTCCTGCAAGGCCTCCGGCT ACACCTTCACCTCCTACTGGATGCACTGGGTGCGGCAGGC CCCCGGCCAGCGGCTGGAGTGGATCGGCGAGATCAACCC CACCAACGGCCGGACCAACTACATCGAGAAGTTCAAGTC CCGGGCCACCCTGACCGTGGACAAGTCCGCCTCCACCGC CTACATGGAGCTGTCCTCCCTGCGGTCCGAGGACACCGCC GTGTACTACTGCGCCCGGGGCACCCGGGCCTACCACTACT GGGGCCAGGGCACCATGGTGACCGTGTCCTCCGCCTCCA CCAAGGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGC TGTCCTACAGTCCTCAGGACTCTACTCCCTCAGCAGCGTG GTGACTGTGCCCTCCAGCAGCTTGGGCACCCAGACCTAC ATCTGCAACGTGAATCACAAGCCCAGCAACACCAAGGTG GACAAGAAAGTTGAGCCCAAATCTTGTGACAAAACTCAC ACATGCCCACCGTGCCCAGCACCTGAACTCCTGGGGGGA CCGTCAGTCTTCCTCTTCCCCCCAAAACCCAAGGACACCC TCATGATCTCCCGGACCCCTGAGGTCACATGCGTGGTGGT GGACGTGAGCCACGAAGACCCTGAGGTCAAGTTCAACTG GTACGTGGACGGCGTGGAGGTGCATAATGCCAAGACAAA GCCGCGGGAGGAGCAGTACAACAGCACGTACCGTGTGGT CAGCGTCCTTACCGTCCTGCACCAGGACTGGCTGAATGGC AAGGAGTACAAGTGCAAGGTCTCCAACAAAGCCCTCCCA GCCCCCATCGAGAAAACCATCTCCAAAGCCAAAGGGCAG CCCCGAGAACCACAGGTGACCACCCTGCCCCCATCCCGG GATGAGCTGACCAAGAACCAGGTCAGCCTGACCTGCCTG GTCAAAGGCTTCTATCCCAGCGACATCGCCGTGGAGTGG GAGAGCAATGGGCAGCCGGAGAACAACTACAAGACCTTC CCTCCCGTGCTGGACTCCGACGGCTCCTTCTTCCTCTACA GCAAGCTCACCGTGGACAAGAGCAGGTGGCAGCAGGGG AACGTCTTCTCATGCTCCGTGATGCATGAGGCTCTGCACA ACCACTACACGCAGAAGAGCCTCTCCCTGTCTCCGGGTA AAGGAGGCGGTGGATCAGGACAATTCAGAGTGATAGGAC CAGGGTATCCCATCCGGGCTTTAGTTGGGGATGAAGCAG AGCTGCCGTGCCGCATCTCTCCTGGGAAAAATGCCACGG GCATGGAGGTGGGTTGGTACCGTTCTCCCTTCTCAAGAGT GGTTCACCTCTACCGAAATGGCAAGGACCAAGATGCAGA GCAAGCACCTGAATACCGGGGACGCACAGAGCTTCTGAA AGAGACTATCAGTGAGGGAAAGGTTACCCTTAGGATTCA GAACGTGAGATTCTCAGATGAAGGAGGCTACACCTGCTT CTTCAGAGACCACTCTTACCAAGAAGAGGCAGCAATGGA GTTGAAAGTGGAAGAT | 15 |

TABLE 1-continued

DNA sequences of polynucleotides encoding exemplary proteins.

| Polynucleotide encoding protein | DNA sequence | SEQ ID NO: |
|---|---|---|
| TfR Ab with knobs-into-holes mutations | GAGGTGCAGCTGGTGCAGTCCGGCGCCGAGGTGAAGAAG CCCGGCGCCTCCGTGAAGGTGTCCTGCAAGGCCTCCGGCT ACACCTTCACCTCCTACTGGATGCACTGGGTGCGGCAGGC CCCCGGCCAGCGGCTGGAGTGGATCGGCGAGATCAACCC CACCAACGGCCGGACCAACTACATCGAGAAGTTCAAGTC CCGGGCCACCCTGACCGTGGACAAGTCCGCCTCCACCGC CTACATGGAGCTGTCCTCCCTGCGGTCCGAGGACACCGCC GTGTACTACTGCGCCCGGGGCACCCGGGCCTACCACTACT GGGGCCAGGGCACCATGGTGACCGTGTCCTCCGCCTCCA CCAAGGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGC TGTCCTACAGTCCTCAGGACTCTACTCCCTCAGCAGCGTG GTGACTGTGCCCTCCAGCAGCTTGGGCACCCAGACCTAC ATCTGCAACGTGAATCACAAGCCCAGCAACACCAAGGTG GACAAGAAAGTTGAGCCCAAATCTTGTGACAAAACTCAC ACATGCCCACCGTGCCCAGCACCTGAACTCCTGGGGGGA CCGTCAGTCTTCCTCTTCCCCCCAAAACCCAAGGACACCC TCATGATCTCCCGGACCCCTGAGGTCACATGCGTGGTGGT GGACGTGAGCCACGAAGACCCTGAGGTCAAGTTCAACTG GTACGTGGACGGCGTGGAGGTGCATAATGCCAAGACAAA GCCGCGGGAGGAGCAGTACAACAGCACGTACCGTGTGGT CAGCGTCCTCACCGTCCTGCACCAGGACTGGCTGAATGG CAAGGAGTACAAGTGCAAGGTCTCCAACAAAGCCCTCCC AGCCCCCATCGAGAAAACCATCTCCAAAGCCAAAGGGCA GCCCCGAGAACCACAGGTGTACACCCTGCCCCCATCCCG GGATGAGCTGACCAAGAACCAGGTCCACCTGACCTGCCT GGTCAAAGGCTTCTATCCCAGCGACATCGCCGTGGAGTG GGAGAGCAATGGGCAGCCGGAGAACAACTACAAGACCA CGCCTCCCGTGCTGGACTCCGACGGCTCCTTCGCCCTCTA CAGCAAGCTCACCGTGGACAAGAGCAGGTGGCAGCAGG GGAACGTCTTCTCATGCTCCGTGATGCATGAGGCTCTGCA CAACCACTACACGCAGAAGAGCCTCTCCCTGTCTCCGGGT AAA | 17 |
| TfR Ab LC | GACATCCAGATGACCCAGTCCCCCTCCTCCCTGTCCGCCT CCGTGGGCGACCGGGTGACCATCACCTGCCGGGCCTCCG ACAACCTGTACTCCAACCTGGCCTGGTACCAGCAGAAGC CCGGCAAGTCCCCCAAGCTGCTGGTGTACGACGCCACCA ACCTGGCCGACGGCGTGCCCTCCCGGTTCTCCGGCTCCGG CTCCGGCACCGACTACACCCTGACCATCTCCTCCCTGCAG CCCGAGGACTTCGCCACCTACTACTGCCAGCACTTCTGGG GCACCCCCCTGACCTTCGGCCAGGGCACCAAGGTGGAGA TCAAGACTGTGGCTGCACCATCTGTCTTCATCTTCCCGCC ATCTGATGAGCAGTTGAAATCTGGAACTGCCTCTGTTGTG TGCCTGCTGAATAACTTCTATCCCAGAGAGGCCAAAGTA CAGTGGAAGGTGGATAACGCCCTCCAATCGGGTAACTCC CAGGAGAGTGTCACAGAGCAGGACAGCAAGGACAGCAC CTACAGCCTCAGCAGCACCCTGACGCTGAGCAAAGCAGA CTACGAGAAACACAAAGTCTACGCCTGCGAAGTCACCCA TCAGGGCCTGAGTTCGCCCGTCACAAAGAGCTTCAACAG GGGAGAGTGT | 19 |
| MOG-Seldeg-TfR with knobs-into-holes and arginine mutations | GAGGTGCAGCTGGTGCAGTCCGGCGCCGAGGTGAAGAAG CCCGGCGCCTCCGTGAAGGTGTCCTGCAAGGCCTCCGGCT ACACCTTCACCTCCTACTGGATGCACTGGGTGCGGCAGGC CCCCGGCCAGCGGCTGGAGTGGATCGGCGAGATCAACCC CACCAACGGCCGGACCAACTACATCGAGAAGTTCAAGTC CCGGGCCACCCTGACCGTGGACAAGTCCGCCTCCACCGC CTACATGGAGCTGTCCTCCCTGCGGTCCGAGGACACCGCC GTGTACTACTGCGCCCGGGGCACCCGGGCCTACCACTACT GGGGCCAGGGCACCATGGTGACCGTGTCCTCCGCCTCCA CCAAGGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGC TGTCCTACAGTCCTCAGGACTCTACTCCCTCAGCAGCGTG GTGACTGTGCCCTCCAGCAGCTTGGGCACCCAGACCTAC ATCTGCAACGTGAATCACAAGCCCAGCAACACCAAGGTG GACAAGAAAGTTGAGCCCAAATCTTGTGACAAAACTCAC ACATGCCCACCGTGCCCAGCACCTGAACTCCTGAGGGGA CCGTCAGTCTTCCTCTTCCCCCCAAAACCCAAGGACACCC | 21 |

TABLE 1-continued

DNA sequences of polynucleotides encoding exemplary proteins.

| Polynucleotide encoding protein | DNA sequence | SEQ ID NO: |
|---|---|---|
| | TCATGATCTCCCGGACCCCTGAGGTCACATGCGTGGTGGT GGACGTGAGCCACGAAGACCCTGAGGTCAAGTTCAACTG GTACGTGGACGGCGTGGAGGTGCATAATGCCAAGACAAA GCCGCGGGAGGAGCAGTACAACAGCACGTACCGTGTGGT CAGCGTCCTTACCGTCCTGCACCAGGACTGGCTGAATGGC AAGGAGTACAAGTGCAAGGTCTCCAACAAAGCCCGCCCA GCCCCCATCGAGAAAACCATCTCCAAAGCCAAAGGGCAG CCCCGAGAACCACAGGTGACCACCCTGCCCCCATCCCGG GATGAGCTGACCAAGAACCAGGTCAGCCTGACCTGCCTG GTCAAAGGCTTCTATCCCAGCGACATCGCCGTGGAGTGG GAGAGCAATGGGCAGCCGGAGAACAACTACAAGACCTTC CCTCCCGTGCTGGACTCCGACGGCTCCTTCTTCCTCTACA GCAAGCTCACCGTGGACAAGAGCAGGTGGCAGCAGGGG AACGTCTTCTCATGCTCCGTGATGCATGAGGCTCTGCACA ACCACTACACGCAGAAGAGCCTCTCCCTGTCTCCGGGTA AAGGAGGCGGTGGATCAGGACAATTCAGAGTGATAGGAC CAGGGTATCCCATCCGGGCTTTAGTTGGGGATGAAGCAG AGCTGCCGTGCCGCATCTCTCCTGGGAAAAATGCCACGG GCATGGAGGTGGGTTGGTACCGTTCTCCCTTCTCAAGAGT GGTTCACCTCTACCGAAATGGCAAGGACCAAGATGCAGA GCAAGCACCTGAATACCGGGGACGCACAGAGCTTCTGAA AGAGACTATCAGTGAGGGAAAGGTTACCCTTAGGATTCA GAACGTGAGATTCTCAGATGAAGGAGGCTACACCTGCTT CTTCAGAGACCACTCTTACCAAGAAGAGGCAGCAATGGA GTTGAAAGTGGAAGAT | |
| TfR Ab with knobs-into-holes and arginine mutations | GAGGTGCAGCTGGTGCAGTCCGGCGCCGAGGTGAAGAAG CCCGGCGCCTCCGTGAAGGTGTCCTGCAAGGCCTCCGGCT ACACCTTCACCTCCTACTGGATGCACTGGGTGCGGCAGGC CCCCGGCCAGCGGCTGGAGTGGATCGGCGAGATCAACCC CACCAACGGCCGGACCAACTACATCGAGAAGTTCAAGTC CCGGGCCACCCTGACCGTGGACAAGTCCGCCTCCACCGC CTACATGGAGCTGTCCTCCCTGCGGTCCGAGGACACCGCC GTGTACTACTGCGCCCGGGGCACCCGGGCCTACCACTACT GGGGCCAGGGCACCATGGTGACCGTGTCCTCCGCCTCCA CCAAGGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGC TGTCCTACAGTCCTCAGGACTCTACTCCCTCAGCAGCGTG GTGACTGTGCCCTCCAGCAGCTTGGGCACCCAGACCTAC ATCTGCAACGTGAATCACAAGCCCAGCAACACCAAGGTG GACAAGAAAGTTGAGCCCAAATCTTGTGACAAAACTCAC ACATGCCCACCGTGCCCAGCACCTGAACTCCTGAGGGGA CCGTCAGTCTTCCTCTTCCCCCCAAAACCCAAGGACACCC TCATGATCTCCCGGACCCCTGAGGTCACATGCGTGGTGGT GGACGTGAGCCACGAAGACCCTGAGGTCAAGTTCAACTG GTACGTGGACGGCGTGGAGGTGCATAATGCCAAGACAAA GCCGCGGGAGGAGCAGTACAACAGCACGTACCGTGTGGT CAGCGTCCTCACCGTCCTGCACCAGGACTGGCTGAATGG CAAGGAGTACAAGTGCAAGGTCTCCAACAAAGCCCGCCC AGCCCCCATCGAGAAAACCATCTCCAAAGCCAAAGGGCA GCCCCGAGAACCACAGGTGTACACCCTGCCCCCATCCCG GGATGAGCTGACCAAGAACCAGGTCCACCTGACCTGCCT GGTCAAAGGCTTCTATCCCAGCGACATCGCCGTGGAGTG GGAGAGCAATGGGCAGCCGGAGAACAACTACAAGACCA CGCCTCCCGTGCTGGACTCCGACGGCTCCTTCGCCCTCTA CAGCAAGCTCACCGTGGACAAGAGCAGGTGGCAGCAGG GGAACGTCTTCTCATGCTCCGTGATGCATGAGGCTCTGCA CAACCACTACACGCAGAAGAGCCTCTCCCTGTCTCCGGGT AAA | 23 |
| HER2-ECD-Fc with MST-HN and knobs-into-holes | ACCCAAGTGTGCACCGGCACAGACATGAAGCTGCGGCTC CCTGCCAGTCCCGAGACCCACCTGGACATGCTCCGCCAC CTCTACCAGGGCTGCCAGGTGGTGCAGGGAAACCTGGAA CTCACCTACCTGCCCACCAATGCCAGCCTGTCCTTCCTGC AGGATATCCAGGAGGTGCAGGGCTACGTGCTCATCGCTC ACAACCAAGTGAGGCAGGTCCCACTGCAGAGGCTGCGGA TTGTGCGAGGCACCCAGCTCTTTGAGGACAACTATGCCCT GGCCGTGCTAGACAATGGAGACCCGCTGAACAATACCAC CCCTGTCACAGGGGCCTCCCCAGGAGGCCTGCGGGAGCT GCAGCTTCGAAGCCTCACAGAGATCTTGAAAGGAGGGGT CTTGATCCAGCGGAACCCCCAGCTCTGCTACCAGGACAC GATTTTGTGGAAGGACATCTTCCACAAGAACAACCAGCT | 25 |

TABLE 1-continued

DNA sequences of polynucleotides encoding exemplary proteins.

| Polynucleotide encoding protein | DNA sequence | SEQ ID NO: |
|---|---|---|
| | GGCTCTCACACTGATAGACACCAACCGCTCTCGGGCCTGC CACCCCTGTTCTCCGATGTGTAAGGGCTCCCGCTGCTGGG GAGAGAGTTCTGAGGATTGTCAGAGCCTGACGCGCACTG TCTGTGCCGGTGGCTGTGCCCGCTGCAAGGGGCCACTGCC CACTGACTGCTGCCATGAGCAGTGTGCTGCCGGCTGCAC GGGCCCCAAGCACTCTGACTGCCTGGCCTGCCTCCACTTC AACCACAGTGGCATCTGTGAGCTGCACTGCCCAGCCCTG GTCACCTACAACACAGACACGTTTGAGTCCATGCCCAATC CCGAGGGCCGGTATACATTCGGCGCCAGCTGTGTGACTG CCTGTCCCTACAACTACCTTTCTACGGACGTGGGATCCTG CACCCTCGTCTGCCCCCTGCACAACCAAGAGGTGACAGC AGAGGATGGAACACAGCGGTGTGAGAAGTGCAGCAAGC CCTGTGCCCGAGTGTGCTATGGTCTGGGCATGGAGCACTT GCGAGAGGTGAGGGCAGTTACCAGTGCCAATATCCAGGA GTTTGCTGGCTGCAAGAAGATCTTTGGGAGCCTGGCATTT CTGCCGGAGAGCTTTGATGGGGACCCAGCCTCCAACACT GCCCCGCTCCAGCCAGAGCAGCTCCAAGTGTTTGAGACT CTGGAAGAGATCACAGGTTACCTATACATCTCAGCATGG CCGGACAGCCTGCCTGACCTCAGCGTCTTCCAGAACCTGC AAGTAATCCGGGGACGAATTCTGCACAATGGCGCCTACT CGCTGACCCTGCAAGGGCTGGGCATCAGCTGGCTGGGGC TGCGCTCACTGAGGGAACTGGGCAGTGGACTGGCCCTCA TCCACCATAACACCCACCTCTGCTTCGTGCACACGGTGCC CTGGGACCAGCTCTTTCGGAACCCGCACCAAGCTCTGCTC CACACTGCCAACCGGCCAGAGGACGAGTGTGTGGGCGAG GGCCTGGCCTGCCACCAGCTGTGCGCCCGAGGGCACTGC TGGGGTCCAGGGCCCACCCAGTGTGTCAACTGCAGCCAG TTCCTTCGGGGCCAGGAGTGCGTGGAGGAATGCCGAGTA CTGCAGGGGCTCCCCAGGGAGTATGTGAATGCCAGGCAC TGTTTGCCGTGCCACCCTGAGTGTCAGCCCCAGAATGGCT CAGTGACCTGTTTTGGACCGGAGGCTGACCAGTGTGTGG CCTGTGCCCACTATAAGGACCCTCCCTTCTGCGTGGCCCG CTGCCCCAGCGGTGTGAAACCTGACCTCTCCTACATGCCC ATCTGGAAGTTTCCAGATGAGGAGGGCGCATGCCAGCCT TGCCCCATCAACTGCACCCACTCCTGTGTGGACCTGGATG ACAAGGGCTGCCCCGCCGAGCAGAGAGCCAGCCCTCTGA CGATTGAAGGCCGCATGGATCCCAAATCTTCTGACAAAA CTCACACATGCCCACCGTGCCCAGCACCTGAACTCCTGG GGGGACCGTCAGTCTTCCTCTTCCCCCCAAAACCCAAGGA CACCCTCTACATCACTCGGGAACCTGAGGTCACATGCGTG GTGGTGGACGTGAGCCACGAAGACCCTGAGGTCAAGTTC AACTGGTACGTGGACGGCGTGGAGGTGCATAATGCCAAG ACAAAGCCGCGGGAGGAGCAGTACAACAGCACGTACCGT GTGGTCAGCGTCCTCACCGTCCTGCACCAGGACTGGCTGA ATGGCAAGGAGTACAAGTGCAAGGTCTCCAACAAAGCCC TCCCAGCCCCCATCGAGAAAACCATCTCCAAAGCCAAAG GGCAGCCCCGAGAACCACAGGTGACCACCCTGCCCCCAT CCCGGGATGAGCTGACCAAGAACCAGGTCAGCCTGACCT GCCTGGTCAAAGGCTTCTATCCCAGCGACATCGCCGTGG AGTGGGAGAGCAATGGGCAGCCGGAGAACAACTACAAG ACCTTCCCTCCCGTGCTGGACTCCGACGGCTCCTTCTTCCT CTACAGCAAGCTCACCGTGGACAAGAGCAGGTGGCAGCA GGGGAACGTCTTCTCATGCTCTGTGATGCATGAGGCTCTG AAATTCCACTACACGCAGAAGAGCCTCTCCCTGTCTCCTG GTAAA | |
| Fc with MST-HN and knobs-into-holes mutations | GTTGAGCCCAAATCTTCTGACAAAACTCACACATGCCCAC CGTGCCCAGCACCTGAACTCCTGGGGGGACCGTCAGTCTT CCTCTTCCCCCCAAAACCCAAGGACACCCTCTACATCACT CGGGAACCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCTCCCAGCCCCCAT CGAGAAAACCATCTCCAAAGCCAAAGGGCAGCCCCGAGA ACCACAGGTGTACACCCTGCCCCCATCCCGGGATGAGCT GACCAAGAACCAGGTCCACCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGGACTCCGACGGCTCCTTCGCCCTCTACAGCAAGCTC ACCGTGGACAAGAGCAGGTGGCAGCAGGGGAACGTCTTC TCATGCTCCGTGATGCATGAGGCTCTGAAATTCCACTACA CGCAGAAGAGCCTCTCCCTGTCTCCGGGTAAA | 27 |

TABLE 1-continued

DNA sequences of polynucleotides encoding exemplary proteins.

| Polynucleotide encoding protein | DNA sequence | SEQ ID NO: |
|---|---|---|
| PSMA-Seldeg with MST-HN, knobs-into-holes and arginine mutations | GTTGAGCCCAAATCTTCTGACAAAACTCACACATGCCCAC CGTGCCCAGCACCTGAACTCCTGAGGGGACCGTCAGTCTT CCTCTTCCCCCCAAAACCCAAGGACACCCTCTACATCACT CGGGAACCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCGCCCAGCCCCCAT CGAGAAAACCATCTCCAAAGCCAAAGGGCAGCCCCGAGA ACCACAGGTGACCACCCTGCCCCCATCCCGGGATGAGCT GACCAAGAACCAGGTCAGCCTGACCTGCCTGGTCAAAGG CTTCTATCCCAGCGACATCGCCGTGGAGTGGGAGAGCAA TGGGCAGCCGGAGAACAACTACAAGACCTTCCCTCCCGT GCTGGACTCCGACGGCTCCTTCTTCCTCTACAGCAAGCTC ACCGTGGACAAGAGCAGGTGGCAGCAGGGGAACGTCTTC TCATGCTCTGTGATGCATGAGGCTCTGAAATTCCACTACA CGCAGAAGAGCCTCTCCCTGTCTCCGGGTAAAGGAGGCG GTGGATCAAAATCCTCCAATGAAGCTACTAACATTACTCC AAAGCATAATATGAAAGCATTTTTGGATGAATTGAAAGC TGAGAACATCAAGAAGTTCTTATATAATTTTACACAGATA CCACATTTAGCAGGAACAGAACAAAACTTTCAGCTTGCA AAGCAAATTCAATCCCAGTGGAAAGAATTTGGCCTGGAT TCTGTTGAGCTAGCACATTATGATGTCCTGTTGTCCTACC CAAATAAGACTCATCCCAACTACATCTCAATAATTAATGA AGATGGAAATGAGATTTTCAACACATCATTATTTGAACCA CCTCCTCCAGGATATGAAAATGTTTCGGATATTGTACCAC CTTTCAGTGCTTTCTCTCCTCAAGGAATGCCAGAGGGCGA TCTAGTGTATGTTAACTATGCACGAACTGAAGACTTCTTT AAATTGGAACGGGACATGAAAATCAATTGCTCTGGGAAA ATTGTAATTGCCAGATATGGGAAAGTTTTCAGAGGAAAT AAGGTTAAAAATGCCCAGCTGGCAGGGGCCAAAGGAGTC ATTCTCTACTCCGACCCTGCTGACTACTTTGCTCCTGGGG TGAAGTCCTATCCAGATGGTTGGAATCTTCCTGGAGGTGG TGTCCAGCGTGGAAATATCCTAAATCTGAATGGTGCAGG AGACCCTCTCACACCAGGTTACCCAGCAAATGAATATGC TTATAGGCGTGGAATTGCAGAGGCTGTTGGTCTTCCAAGT ATTCCTGTTCATCCAATTGGATACTATGATGCACAGAAGC TCCTAGAAAAAATGGGTGGCTCAGCACCACCAGATAGCA GCTGGAGAGGAAGTCTCAAAGTGCCCTACAATGTTGGAC CTGGCTTTACTGGAAACTTTTCTACACAAAAAGTCAAGAT GCACATCCACTCTACCAATGAAGTGACAAGAATTTACAA TGTGATAGGTACTCTCAGAGGAGCAGTGGAACCAGACAG ATATGTCATTCTGGGAGGTCACCGGGACTCATGGGTGTTT GGTGGTATTGACCCTCAGAGTGGAGCAGCTGTTGTTCATG AAATTGTGAGGAGCTTTGGAACACTGAAAAAGGAAGGGT GGAGACCTAGAAGAACAATTTTGTTTGCAAGCTGGGATG CAGAAGAATTTGGTCTTCTTGGTTCTACTGAGTGGGCAGA GGAGAATTCAAGACTCCTTCAAGAGCGTGGCGTGGCTTA TATTAATGCTGACTCATCTATAGAAGGAAACTACACTCTG AGAGTTGATTGTACACCGCTGATGTACAGCTTGGTACACA ACCTAACAAAAGAGCTGAAAAGCCCTGATGAAGGCTTTG AAGGCAAATCTCTTTATGAAAGTTGGACTAAAAAAAGTC CTTCCCCAGAGTTCAGTGGCATGCCAGGATAAGCAAAT TGGGATCTGGAAATGATTTTGAGGTGTTCTTCCAACGACT TGGAATTGCTTCAGGCAGAGCACGGTATACTAAAAATTG GGAAACAAACAAATTCAGCGGCTATCCACTGTATCACAG TGTCTATGAAACATATGAGTTGGTGGAAAAGTTTTATGAT CCAATGTTTAAATATCACCTCACTGTGGCCCAGGTTCGAG GAGGGATGGTGTTTGAGCTAGCCAATTCCATAGTGCTCCC TTTTGATTGTCGAGATTATGCTGTAGTTTTAAGAAAGTAT GCTGACAAAATCTACAGTATTTCTATGAAACATCCACAG GAAATGAAGACATACAGTGTATCATTTGATTCACTTTTTT CTGCAGTAAAGAATTTTACAGAAATTGCTTCCAAGTTCAG TGAGAGACTCCAGGACTTTGACAAAAGCAACCCAATAGT ATTAAGAATGATGAATGATCAACTCATGTTTCTGGAAAG AGCATTTATTGATCCATTAGGGTTACCAGACAGGCCTTTT TATAGGCATGTCATCTATGCTCCAAGCAGCCACAACAAG TATGCAGGGGAGTCATTCCCAGGAATTTATGATGCTCTGT TTGATATTGAAAGCAAAGTGGACCCTTCCAAGGCCTGGG GAGAAGTGAAGAGACAGATTTATGTTGCAGCCTTCACAG TGCAGGCAGCTGCAGAGACTTTGAGTGAAGTAGCC | 29 |

TABLE 1-continued

DNA sequences of polynucleotides encoding exemplary proteins.

| Polynucleotide encoding protein | DNA sequence | SEQ ID NO: |
|---|---|---|
| GAD65-Seldeg with MST-HN, knobs-into-holes and arginine mutations | ATGGCATCTCCGGGCTCTGGCTTTTGGTCTTTCGGGTCGG AAGATGGCTCTGGGGATTCCGAGAATCCCGGCACAGCGC GAGCCTGGTGCCAAGTGGCTCAGAAGTTCACGGGCGGCA TCGGAAACAAACTGTGCGCCCTGCTCTACGGAGACGCCG AGAAGCCGGCGGAGAGCGGCGGGAGCCAACCCCCGCGG GCCGCCGCCCGGAAGGCCGCCTGCGCCTGCGACCAGAAG CCCTGCAGCTGCTCCAAAGTGGATGTCAACTACGCGTTTC TCCATGCAACAGACCTGCTGCCGGCGTGTGATGGAGAAA GGCCCACTTTGGCGTTTCTGCAAGATGTTATGAACATTTT ACTTCAGTATGTGGTGAAAAGTTTCGATAGATCAACCAA AGTGATTGATTTCCATTATCCTAATGAGCTTCTCCAAGAA TATAATTGGGAATTGGCAGACCAACCACAAAATTTGGAG GAAATTTTGATGCATTGCCAAACAACTCTAAAATATGCA ATTAAAACAGGGCATCCTAGATACTTCAATCAACTTTCTA CTGGTTTGGATATGGTTGGATTAGCAGCAGACTGGCTGAC ATCAACAGCAAATACTAACATGTTCACCTATGAAATTGCT CCAGTATTTGTGCTTTTGGAATATGTCACACTAAAGAAAA TGAGAGAAATCATTGGCTGGCAGGGGGCTCTGGCGATG GGATATTTTCTCCCGGTGGCGCCATATCTAACATGTATGC CATGATGATCGCACGCTTTAAGATGTTCCCAGAAGTCAA GGAGAAAGGAATGGCTGCTCTTCCCAGGCTCATTGCCTTC ACGTCTGAACATAGTCATTTTTCTCTCAAGAAGGGAGCTG CAGCCTTAGGGATTGGAACAGACAGCGTGATTCTGATTA AATGTGATGAGAGAGGGAAAATGATTCCATCTGATCTTG AAAGAAGGATTCTTGAAGCCAAACAGAAAGGGTTTGTTC CTTTCCTCGTGAGTGCCACAGCTGGAACCACCGTGTACGG AGCATTTGACCCCCTCTTAGCTGTCGCTGACATTTGCAAA AAGTATAAGATCTGGATGCATGTGGATGCAGCTTGGGGT GGGGGATTACTGATGTCCCGAAAACACAAGTGGAAACTG AGTGGCGTGGAGAGGGCCAACTCTGTGACGTGGAATCCA CACAAGATGATGGGAGTCCCTTTGCAGTGCTCTGCTCTCC TGGTTAGAGAAGAGGGATTGATGCAGAATTGCAACCAAA TGCATGCCTCCTACCTCTTTCAGCAAGATAAACATTATGA CCTGTCCTATGACACTGGAGACAAGGCCTTACAGTGCGG ACGCCACGTTGATGTTTTAAACTATGGCTGATGTGGAGG GCAAAGGGACTACCGGGTTTGAAGCGCATGTTGATAAA TGTTTGGAGTTGGCAGAGTATTTATACAACATCATAAAAA ACCGAGAAGGATATGAGATGGTGTTTGATGGGAAGCCTC AGCACACAAATGTCTGCTTCTGGTACATTCCTCCAAGCTT GCGTACTCTGGAAGACAATGAAGAGAGAATGAGTCGCCT CTCGAAGGTGGCTCCAGTGATTAAAGCCAGAATGATGGA GTATGGAACCACAATGGTCAGCTACCAACCCTTGGGAGA CAAGGTCAATTTCTTCCGCATGGTCATCTCAAACCCAGCG GCAACTCACCAAGACATTGACTTCCTGATTGAAGAAATA GAACGCCTTGGACAAGATTTAGGAGGCGGTGGATCAGTT GAGCCCAAATCTTCTGACAAAACTCACACATGCCCACCG TGCCCAGCACCTGAACTCCTGAGGGGACCGTCAGTCTTCC TCTTCCCCCCAAAACCCAAGGACACCCTCTACATCACTCG GGAACCTGAGGTCACATGCGTGGTGGTGGACGTGAGCCA CGAAGACCCTGAGGTCAAGTTCAACTGGTACGTGGACGG CGTGGAGGTGCATAATGCCAAGACAAAGCCGCGGGAGG AGCAGTACAACAGCACGTACCGTGTGGTCAGCGTCCTCA CCGTCCTGCACCAGGACTGGCTGAATGGCAAGGAGTACA AGTGCAAGGTCTCCAACAAAGCCCGCCCAGCCCCCATCG AGAAAACCATCTCCAAAGCCAAAGGGCAGCCCCGAGAAC CACAGGTGACCACCCTGCCCCCATCCCGGGATGAGCTGA CCAAGAACCAGGTCAGCCTGACCTGCCTGGTCAAAGGCT TCTATCCCAGCGACATCGCCGTGGAGTGGGAGAGCAATG GGCAGCCGGAGAACAACTACAAGACCTTCCCTCCCGTGC TGGACTCCGACGGCTCCTTCTTCCTCTACAGCAAGCTCAC CGTGGACAAGAGCAGGTGGCAGCAGGGGAACGTCTTCTC ATGCTCTGTGATGCATGAGGCTCTGAAATTCCACTACACG CAGAAGAGCCTCTCCCTGTCTCCGGGTAAA | 31 |
| AQP4-Seldeg with MST-HN, knobs-into-holes and arginine mutations | ATGAGTGACAGACCCACAGCAAGGCGGTGGGGTAAGTGT GGACCTTTGTGTACCAGAGAGAACATCATGGTGGCTTTCA AAGGGGTCTGGACTCAAGCTTTCTGGAAAGCAGTCACAG CGGAATTTCTGGCCATGCTTATTTTTGTTCTCCTCAGCCTG GGATCCACCATCAACTGGGGTGGAACAGAAAAGCCTTTA CCGGTCGACATGGTTCTCATCTCCCTTTGCTTTGGACTCA GCATTGCAACCATGGTGCAGTGCTTTGGCCATATCAGCGG TGGCCACATCAACCCTGCAGTGACTGTGGCCATGGTGTGC ACCAGGAAGATCAGCATCGCCAAGTCTGTCTTCTACATCG CAGCCCAGTGCCTGGGGGCCATCATTGGAGCAGGAATCC | 33 |

TABLE 1-continued

DNA sequences of polynucleotides encoding exemplary proteins.

| Polynucleotide encoding protein | DNA sequence | SEQ ID NO: |
|---|---|---|
| | TCTATCTGGTCACACCTCCCAGTGTGGTGGGAGGCCTGGG AGTCACCATGGTTCATGGAAATCTTACCGCTGGTCATGGT CTCCTGGTTGAGTTGATAATCACATTTCAATTGGTGTTTA CTATCTTTGCCAGCTGTGATTCCAAACGGACTGATGTCAC TGGCTCAATAGCTTTAGCAATTGGATTTTCTGTTGCAATT GGACATTTATTTGCAATCAATTATACTGGTGCCAGCATGA ATCCCGCCCGATCCTTTGGACCTGCAGTTATCATGGGAAA TTGGGAAAACCATTGGATATATTGGGTTGGGCCCATCATA GGAGCTGTCCTCGCTGGTGGCCTTTATGAGTATGTCTTCT GTCCAGATGTTGAATTCAAACGTCGTTTTAAAGAAGCCTT CAGCAAAGCTGCCCAGCAAACAAAAGGAAGCTACATGG AGGTGGAGGACAACAGGAGTCAGGTAGAGACGGATGAC CTGATTCTAAAACCTGGAGTGGTGCATGTGATTGACGTTG ACCGGGGAGAGGAGAAGAAGGGGAAAGACCAATCTGGA GAGGTATTGTCTTCAGTAGGAGGCGGTGGATCAGTTGAG CCCAAATCTTCTGACAAAACTCACACATGCCCACCGTGCC CAGCACCTGAACTCCTGAGGGGACCGTCAGTCTTCCTCTT CCCCCCAAAACCCAAGGACACCCTCTACATCACTCGGGA ACCTGAGGTCACATGCGTGGTGGTGGACGTGAGCCACGA AGACCCTGAGGTCAAGTTCAACTGGTACGTGGACGGCGT GGAGGTGCATAATGCCAAGACAAAGCCGCGGGAGGAGC AGTACAACAGCACGTACCGTGTGGTCAGCGTCCTCACCG TCCTGCACCAGGACTGGCTGAATGGCAAGGAGTACAAGT GCAAGGTCTCCAACAAAGCCCGCCCAGCCCCATCGAGA AAACCATCTCCAAAGCCAAAGGGCAGCCCCGAGAACCAC AGGTGACCACCCTGCCCCCATCCCGGGATGAGCTGACCA AGAACCAGGTCAGCCTGACCTGCCTGGTCAAAGGCTTCT ATCCCAGCGACATCGCCGTGGAGTGGGAGAGCAATGGGC AGCCGGAGAACAACTACAAGACCTTCCCTCCCGTGCTGG ACTCCGACGGCTCCTTCTTCCTCTACAGCAAGCTCACCGT GGACAAGAGCAGGTGGCAGCAGGGGAACGTCTTCTCATG CTCTGTGATGCATGAGGCTCTGAAATTCCACTACACGCAG AAGAGCCTCTCCCTGTCTCCGGGTAAA | |

TABLE 2

Amino acid sequences of exemplary proteins.

| Protein | Amino acid sequence | SEQ ID NO: |
|---|---|---|
| MOG-Seldeg with MST-HN, knobs-into-holes and arginine mutations | GQFRVIGPGYPIRALVGDEAELPCRISPGKNATGMEVGWYRS PFSRVVHLYRNGKDQDAEQAPEYRGRTELLKETISEGKVTLRI QNVRFSDEGGYTCFFRDHSYQEEAAMELKVEDGGGGSVEPK SSDKTHTCPPCPAPELLRGPSVFLFPPKPKDTLYITREPEVTCV VVDVSHEDPEVKFNWYVDGVEVHNAKTKPREEQYNSTYRV VSVLTVLHQDWLNGKEYKCKVSNKARPAPIEKTISKAKGQPR EPQVTTLPPSRDELTKNQVSLTCLVKGFYPSDIAVEWESNGQP ENNYKTFPPVLDSDGSFFLYSKLTVDKSRWQQGNVFSCSVMH EALKFHYTQKSLSLSPGK | 2 |
| HER2-Seldeg with MST-HN, knobs-into-holes and arginine mutations | TQVCTGTDMKLRLPASPETHLDMLRHLYQGCQVVQGNLELT YLPTNASLSFLQDIQEVQGYVLIAHNQVRQVPLQRLRIVRGTQ LFEDNYALAVLDNGDPLNNTTPVTGASPGGLRELQLRSLTEIL KGGVLIQRNPQLCYQDTILWKDIFHKNNQLALTLIDTNRSRAC HPCSPMCKGSRCWGESSEDCQSLTRTVCAGGCARCKGPLPTD CCHEQCAAGCTGPKHSDCLACLHFNHSGICELHCPALVTYNT DTFESMPNPEGRYTFGASCVTACPYNYLSTDVGSCTLVCPLH NQEVTAEDGTQRCEKCSKPCARVCYGLGMEHLREVRAVTSA NIQEFAGCKKIFGSLAFLPESFDGDPASNTAPLQPEQLQVFETL EEITGYLYISAWPDSLPDLSVFQNLQVIRGRILHNGAYSLTLQG LGISWLGLRSLRELGSGLALIHHNTHLCFVHTVPWDQLFRNP HQALLHTANRPEDECVGEGLACHQLCARGHCWGPGPTQCVN CSQFLRGQECVEECRVLQGLPREYVNARHCLPCHPECQPQNG SVTCFGPEADQCVACAHYKDPPFCVARCPSGVKPDLSYMPIW KFPDEEGACQPCPINCTHSCVDLDDKGCPAEQRASPLTIEGRM DPKSSDKTHTCPPCPAPELLRGPSVFLFPPKPKDTLYITREPEV TCVVVDVSHEDPEVKFNWYVDGVEVHNAKTKPREEQYNST YRVVSVLTVLHQDWLNGKEYKCKVSNKARPAPIEKTISKAK GQPREPQVTTLPPSRDELTKNQVSLTCLVKGFYPSDIAVEWES | 4 |

TABLE 2-continued

Amino acid sequences of exemplary proteins.

| Protein | Amino acid sequence | SEQ ID NO: |
|---|---|---|
| | NGQPENNYKTFPPVLDSDGSFFLYSKLTVDKSRWQQGNVFSC SVMHEALKFHYTQKSLSLSPGK | |
| Fc with MST-HN, knobs-into-holes and arginine mutations | VEPKSSDKTHTCPPCPAPELLRGPSVFLFPPKPKDTLYITREPE VTCVVVDVSHEDPEVKFNWYVDGVEVHNAKTKPREEQYNS TYRVVSVLTVLHQDWLNGKEYKCKVSNKARPAPIEKTISKAK GQPREPQVYTLPPSRDELTKNQVHLTCLVKGFYPSDIAVEWE SNGQPENNYKTTPPVLDSDGSFALYSKLTVDKSRWQQGNVFS CSVMHEALKFHYTQKSLSLSPGK | 6 |
| MOG-Seldeg-PS with knobs-into-holes and arginine mutations | GQFRVIGPGYPIRALVGDEAELPCRISPGKNATGMEVGWYRS PFSRVVHLYRNGKDQDAEQAPEYRGRTELLKETISEGKVTLRI QNVRFSDEGGYTCFFRDHSYQEEAAMELKVEDGGGGSVEPK SSDKTHTCPPCPAPELLRGPSVFLFPPKPKDTLMISRTPEVTCV VVDVSHEDPEVKFNWYVDGVEVHNAKTKPREEQYNSTYRV VSVLTVLHQDWLNGKEYKCKVSNKARPAPIEKTISKAKGQPR EPQVTTLPPSRDELTKNQVSLTCLVKGFYPSDIAVEWESNGQP ENNYKTFPPVLDSDGSFFLYSKLTVDKSRWQQGNVFSCSVMH EALHNHYTQKSLSLSPGKGGGGSEKLGKLQYSLDYDFQNNQ LLVGIIQAAELPALDMGGTSDPYVKVFLLPDKKKKFETKVHR KTLNPVFNEQFTFKVPYSELGGKTLVMAVYDFDRFSKHDIIGE FKVPMNTVDFGHVTEEWRDLQSA | 8 |
| Fc-Syt1 with knobs-into-holes and arginine mutations | VEPKSSDKTHTCPPCPAPELLRGPSVFLFPPKPKDTLMISRTPE VTCVVVDVSHEDPEVKFNWYVDGVEVHNAKTKPREEQYNS TYRVVSVLTVLHQDWLNGKEYKCKVSNKARPAPIEKTISKAK GQPREPQVYTLPPSRDELTKNQVHLTCLVKGFYPSDIAVEWE SNGQPENNYKTTPPVLDSDGSFALYSKLTVDKSRWQQGNVFS CSVMHEALHNHYTQKSLSLSPGKGGGGSEKLGKLQYSLDYD FQNNQLLVGIIQAAELPALDMGGTSDPYVKVFLLPDKKKKFE TKVHRKTLNPVFNEQFTFKVPYSELGGKTLVMAVYDFDRFSK HDIIGEFKVPMNTVDFGHVTEEWRDLQSA | 10 |
| MOG-Seldeg-PS with knobs-into-holes, electrostatic steering and arginine mutations | GQFRVIGPGYPIRALVGDEAELPCRISPGKNATGMEVGWYRS PFSRVVHLYRNGKDQDAEQAPEYRGRTELLKETISEGKVTLRI QNVRFSDEGGYTCFFRDHSYQEEAAMELKVEDGGGGSVEPK SSDKTHTCPPCPAPELLRGPSVFLFPPKPKDTLMISRTPEVTCV VVDVSHEDPEVKFNWYVDGVEVHNAKTKPREEQYNSTYRV VSVLTVLHQDWLNGKEYKCKVSNKARPAPIEKTISKAKGQPR EPQVTTLPPSRDELTKNQVSLTCLVKGFYPSDIAVEWESNGQP ENNYDTFPPVLDSDGSFFLYSDLTVDKSRWQQGNVFSCSVMH EALHNHYTQKSLSLSPGKGGGGSEKLGKLQYSLDYDFQNNQ LLVGIIQAAELPALDMGGTSDPYVKVFLLPDKKKKFETKVHR KTLNPVFNEQFTFKVPYSELGGKTLVMAVYDFDRFSKHDIIGE FKVPMNTVDFGHVTEEWRDLQSA | 12 |
| Fc-Syt1 with knobs-into-holes, electrostatic steering and arginine mutations | VEPKSSDKTHTCPPCPAPELLRGPSVFLFPPKPKDTLMISRTPE VTCVVVDVSHEDPEVKFNWYVDGVEVHNAKTKPREEQYNS TYRVVSVLTVLHQDWLNGKEYKCKVSNKARPAPIEKTISKAK GQPREPQVYTLPPSRDKLTKNQVHLTCLVKGFYPSDIAVEWE SNGQPENNYKTTPPVLKSDGSFALYSKLTVDKSRWQQGNVFS CSVMHEALHNHYTQKSLSLSPGKGGGGSEKLGKLQYSLDYD FQNNQLLVGIIQAAELPALDMGGTSDPYVKVFLLPDKKKKFE TKVHRKTLNPVFNEQFTFKVPYSELGGKTLVMAVYDFDRFSK HDIIGEFKVPMNTVDFGHVTEEWRDLQSA | 14 |
| MOG-Seldeg-TfR with knobs-into-holes mutations | EVQLVQSGAEVKKPGASVKVSCKASGYTFTSYWMHWVRQA PGQRLEWIGEINPTNGRTNYIEKFKSRATLTVDKSASTAYMEL SSLRSEDTAVYYCARGTRAYHYWGQGTMVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLGGPSVFLFPPKPKDTLMI SRTPEVTCVVVDVSHEDPEVKFNWYVDGVEVHNAKTKPREE QYNSTYRVVSVLTVLHQDWLNGKEYKCKVSNKALPAPIEKTI SKAKGQPREPQVYTLPPSRDELTKNQVSLTCLVKGFYPSDIAV EWESNGQPENNYKTFPPVLDSDGSFFLYSKLTVDKSRWQQG NVFSCSVMHEALHNHYTQKSLSLSPGKGGGGSGQFRVIGPGY PIRALVGDEAELPCRISPGKNATGMEVGWYRSPFSRVVHLYR NGKDQDAEQAPEYRGRTELLKETISEGKVTLRIQNVRFSDEG GYTCFFRDHSYQEEAAMELKVED | 16 |

TABLE 2-continued

Amino acid sequences of exemplary proteins.

| Protein | Amino acid sequence | SEQ ID NO: |
|---|---|---|
| TfR Ab with knobs-into-holes mutations | EVQLVQSGAEVKKPGASVKVSCKASGYTFTSYWMEIWVRQA PGQRLEWIGEINPTNGRTNYIEKFKSRATLTVDKSASTAYMEL SSLRSEDTAVYYCARGTRAYHYWGQGTMVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLGGPSVFLFPPKPKDTLMI SRTPEVTCVVVDVSHEDPEVKFNWYVDGVEVHNAKTKPREE QYNSTYRVVSVLTVLHQDWLNGKEYKCKVSNKALPAPIEKTI SKAKGQPREPQVYTLPPSRDELTKNQVHLTCLVKGFYPSDIA VEWESNGQPENNYKTTPPVLDSDGSFALYSKLTVDKSRWQQ GNVFSCSVMHEALHNHYTQKSLSLSPGK | 18 |
| TfR Ab LC | DIQMTQSPSSLSASVGDRVTITCRASDNLYSNLAWYQQKPGK SPKLLVYDATNLADGVPSRFSGSGSGTDYTLTISSLQPEDFAT YYCQHFWGTPLTFGQGTKVEIKTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSFNRGE C | 20 |
| MOG-Seldeg-TfR with knobs-into-holes and arginine mutations | EVQLVQSGAEVKKPGASVKVSCKASGYTFTSYWMEIWVRQA PGQRLEWIGEINPTNGRTNYIEKFKSRATLTVDKSASTAYMEL SSLRSEDTAVYYCARGTRAYHYWGQGTMVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLRGPSVFLFPPKPKDTLMI SRTPEVTCVVVDVSHEDPEVKFNWYVDGVEVHNAKTKPREE QYNSTYRVVSVLTVLHQDWLNGKEYKCKVSNKARPAPIEKTI SKAKGQPREPQVTTLPPSRDELTKNQVSLTCLVKGFYPSDIAV EWESNGQPENNYKTFPPVLDSDGSFFLYSKLTVDKSRWQQG NVFSCSVMHEALHNHYTQKSLSLSPGKGGGGSGQFRVIGPGY PIRALVGDEAELPCRISPGKNATGMEVGWYRSPFSRVVHLYR NGKDQDAEQAPEYRGRTELLKETISEGKVTLRIQNVRFSDEG GYTCFFRDHSYQEEAAMELKVED | 22 |
| TfR Ab with knobs-into-holes and arginine mutations | EVQLVQSGAEVKKPGASVKVSCKASGYTFTSYWMHWVRQA PGQRLEWIGEINPTNGRTNYIEKFKSRATLTVDKSASTAYMEL SSLRSEDTAVYYCARGTRAYHYWGQGTMVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLRGPSVFLFPPKPKDTLMI SRTPEVTCVVVDVSHEDPEVKFNWYVDGVEVHNAKTKPREE QYNSTYRVVSVLTVLHQDWLNGKEYKCKVSNKARPAPIEKTI SKAKGQPREPQVYTLPPSRDELTKNQVHLTCLVKGFYPSDIA VEWESNGQPENNYKTTPPVLDSDGSFALYSKLTVDKSRWQQ GNVFSCSVMHEALHNHYTQKSLSLSPGK | 24 |
| HER2-ECD-Fc with MST-HN and knobs-into-holes | TQVCTGTDMKLRLPASPETHLDMLRHLYQGCQVVQGNLELT YLPTNASLSFLQDIQEVQGYVLIAHNQVRQVPLQRLRIVRGTQ LFEDNYALAVLDNGDPLNNTTPVTGASPGGLRELQLRSLTEIL KGGVLIQRNPQLCYQDTILWKDIFHKNNQLALTLIDTNRSRAC HPCSPMCKGSRCWGESSEDCQSLTRTVCAGGCARCKGPLPTD CCHEQCAAGCTGPKHSDCLACLHFNHSGICELHCPALVTYNT DTFESMPNPEGRYTFGASCVTACPYNYLSTDVGSCTLVCPLH NQEVTAEDGTQRCEKCSKPCARVCYGLGMEHLREVRAVTSA NIQEFAGCKKIFGSLAFLPESFDGDPASNTAPLQPEQLQVFETL EEITGYLYISAWPDSLPDLSVFQNLQVIRGRILHNGAYSLTLQG LGISWLGLRSLRELGSGLALIHHNTHLCFVHTVPWDQLFRNP HQALLHTANRPEDECVGEGLACHQLCARGHCWGPGPTQCVN CSQFLRGQECVEECRVLQGLPREYVNARHCLPCHPECQPQNG SVTCFGPEADQCVACAHYKDPPFCVARCPSGVKPDLSYMPIW KFPDEEGACQPCPINCTHSCVDLDDKGCPAEQRASPLTIEGRM DPKSSDKTHTCPPCPAPELLGGPSVFLFPPKPKDTLYITREPEV TCVVVDVSHEDPEVKFNWYVDGVEVHNAKTKPREEQYNST YRVVSVLTVLHQDWLNGKEYKCKVSNKALPAPIEKTISKAKG QPREPQVTTLPPSRDELTKNQVSLTCLVKGFYPSDIAVEWESN GQPENNYKTFPPVLDSDGSFFLYSKLTVDKSRWQQGNVFScS VMHEALKFHYTQKSLSLSPGK | 26 |

TABLE 2-continued

Amino acid sequences of exemplary proteins.

| Protein | Amino acid sequence | SEQ ID NO: |
|---|---|---|
| Fc with MST-HN and knobs-into-holes mutations | VEPKSSDKTHTCPPCPAPELLGGPSVFLFPPKPKDTLYITREPE<br>VTCVVVDVSHEDPEVKFNWYVDGVEVHNAKTKPREEQYNS<br>TYRVVSVLTVLHQDWLNGKEYKCKVSNKALPAPIEKTISKAK<br>GQPREPQVYTLPPSRDELTKNQVHLTCLVKGFYPSDIAVEWE<br>SNGQPENNYKTTPPVLDSDGSFALYSKLTVDKSRWQQGNVFS<br>CSVMHEALKFHYTQKSLSLSPGK | 28 |
| PSMA-Seldeg with MST-HN, knobs-into-holes and arginine mutations | VEPKSSDKTHTCPPCPAPELLRGPSVFLFPPKPKDTLYITREPE<br>VTCVVVDVSHEDPEVKFNWYVDGVEVHNAKTKPREEQYNS<br>TYRVVSVLTVLHQDWLNGKEYKCKVSNKARPAPIEKTISKAK<br>GQPREPQVTTLPPSRDELTKNQVSLTCLVKGFYPSDIAVEWES<br>NGQPENNYKTFPPVLDSDGSFFLYSKLTVDKSRWQQGNVFSC<br>SVMHEALKFHYTQKSLSLSPGKGGGGSKSSNEATNITPKHNM<br>KAFLDELKAENIKKFLYNFTQIPHLAGTEQNFQLAKQIQSQW<br>KEFGLDSVELAHYDVLLSYPNKTHPNYISTINEDGNEIFNTSLF<br>EPPPPGYENVSDIVPPFSAFSPQGMPEGDLVYVNYARTEDFFK<br>LERDMKINCSGKIVIARYGKVFRGNKVKNAQLAGAKGVILYS<br>DPADYFAPGVKSYPDGWNLPGGGVQRGNILNLNGAGDPLTP<br>GYPANEYAYRRGIAEAVGLPSIPVHPIGYYDAQKLLEKMGGS<br>APPDSSWRGSLKVPYNVGPGFTGNFSTQKVKMHIHSTNEVTR<br>IYNVIGTLRGAVEPDRYVILGGHRDSWVFGGIDPQSGAAVVH<br>EIVRSFGTLKKEGWRPRRTILFASWDAEEFGLLGSTEWAEENS<br>RLLQERGVAYINADSSIEGNYTLRVDCTPLMYSLVHNLTKEL<br>KSPDEGFEGKSLYESWTKKSPSPEFSGMPRISKLGSGNDFEVF<br>FQRLGIASGRARYTKNWETNKFSGYPLYHSVYETYELVEKFY<br>DPMFKYHLTVAQVRGGMVFELANSIVLPFDCRDYAVVLRKY<br>ADKIYSISMKHPQEMKTYSVSFDSLFSAVKNFTEIASKFSERLQ<br>DFDKSNPIVLRMMNDQLMFLERAFIDPLGLPDRPFYRHVIYAP<br>SSHNKYAGESFPGIYDALFDIESKVDPSKAWGEVKRQIYVAAF<br>TVQAAAETLSEVA | 30 |
| GAD65-Seldeg with MST-HN, knobs-into-holes and arginine mutations | MASPGSGFWSFGSEDGSGDSENPGTARAWCQVAQKFTGGIG<br>NKLCALLYGDAEKPAESGGSQPPRAAARKAACACDQKPCSC<br>SKVDVNYAFLHATDLLPACDGERPTLAFLQDVMNILLQYVV<br>KSFDRSTKVIDFHYPNELLQEYNWELADQPQNLEEILMHCQT<br>TLKYAIKTGHPRYFNQLSTGLDMVGLAADWLTSTANTNMFT<br>YEIAPVFVLLEYVTLKKMREIIGWPGGSGDGIFSPGGAISNMY<br>AMMIARFKMFPEVKEKGMAALPRLIAFTSEHSHFSLKKGAAA<br>LGIGTDSVILIKCDERGKMIPSDLERRILEAKQKGFVPFLVSAT<br>AGTTVYGAFDPLLAVADICKKYKIWMHVDAAWGGGLLMSR<br>KHKWKLSGVERANSVTWNPHKMMGVPLQCSALLVREEGLM<br>QNCNQMHASYLFQQDKHYDLSYDTGDKALQCGRHVDVFKL<br>WLMWRAKGTTGFEAHVDKCLELAEYLYNIIKNREGYEMVFD<br>GKPQHTNVCFWYIPPSLRTLEDNEERMSRLSKVAPVIKARMM<br>EYGTTMVSYQPLGDKVNFFRMVISNPAATHQDIDFLIEEIERL<br>GQDLGGGGSVEPKSSDKTHTCPPCPAPELLRGPSVFLFPPKPK<br>DTLYITREPEVTCVVVDVSHEDPEVKFNWYVDGVEVHNAKT<br>KPREEQYNSTYRVVSVLTVLHQDWLNGKEYKCKVSNKARPA<br>PIEKTISKAKGQPREPQVTTLPPSRDELTKNQVSLTCLVKGFYP<br>SDIAVEWESNGQPENNYKTFPPVLDSDGSFFLYSKLTVDKSR<br>WQQGNVFSCSVMHEALKFHYTQKSLSLSPGK | 32 |
| AQP4-Seldeg with MST-HN, knobs-into-holes and arginine mutations | MSDRPTARRWGKCGPLCTRENIMVAFKGVWTQAFWKAVTA<br>EFLAMLIFVLLSLGSTINWGGTEKPLPVDMVLISLCFGLSIATM<br>VQCFGHISGGHINPAVTVAMVCTRKISIAKSVFYIAAQCLGAII<br>GAGILYLVTPPSVVGGLGVTMVHGNLTAGHGLLVELIITFQLV<br>FTIFASCDSKRTDVTGSIALAIGFSVAIGHLFAINYTGASMNPA<br>RSFGPAVIMGNWENHWIYWVGPIIGAVLAGGLYEYVFCPDVE<br>FKRRFKEAFSKAAQQTKGSYMEVEDNRSQVETDDLILKPGVV<br>HVIDVDRGEEKKGKDQSGEVLSSVGGGGSVEPKSSDKTHTCP<br>PCPAPELLRGPSVFLFPPKPKDTLYITREPEVTCVVVDVSHEDP<br>EVKFNWYVDGVEVHNAKTKPREEQYNSTYRVVSVLTVLHQ<br>DWLNGKEYKCKVSNKARPAPIEKTISKAKGQPREPQVTTLPPS<br>RDELTKNQVSLTCLVKGFYPSDIAVEWESNGQPENNYKTFPP<br>VLDSDGSFFLYSKLTVDKSRWQQGNVFSCSVMHEALKFHYT<br>QKSLSLSPGK | 34 |

The DNA sequence of SEQ ID NO: 1 is of a polynucleotide encoding an exemplary MOG-Seldeg fusion protein (SEQ ID NO: 2) having mutations to increase FcRn binding, knobs-into-holes mutations and arginine mutations. The exemplary DNA and amino acid sequences of the MOG respectively of SEQ ID NO: 1 and 2 are of mouse origin.

In particular, the amino acid sequence of the exemplary MOG-Seldeg of SEQ ID NO: 2 forms a fusion protein having, in order from N- to C-terminus, residues 1-117 of mouse (m) MOG, a first linker at residues 118-122, an immunoglobulin hinge (human IgG1-derived) at residues 123-138, an immunoglobulin CH2 domain (human IgG1-derived) at residues 139-248, an immunoglobulin CH3 domain (human IgG1-derived) at residues 249-355. The exemplary MOG-Seldeg of SEQ ID NO: 2 has mutations that increase FcRn binding at residues 160, 162, 164, 341 and 342, arginine mutations at residues 144 and 236, and 'knobs-into-holes' mutations at residues 257 and 302. The cysteine residue (128) that usually pairs with an immunoglobulin light chain is mutated to serine. The amino acid residue numbers referred to in SEQ ID NO: 2 are those of the protein sequence, and do not refer to the EU numbering convention.

The DNA sequence of SEQ ID NO: 3 is of a polynucleotide encoding an exemplary HER2-Seldeg fusion protein (SEQ ID NO: 4) having mutations to increase FcRn binding, knobs-into-holes mutations and arginine mutations.

In particular, the amino acid sequence of the exemplary HER2-Seldeg of SEQ ID NO: 4 forms a fusion protein having, in order from N- to C-terminus, residues 1-630 of HER2, a first linker at residues 631-636, an immunoglobulin hinge (human IgG1-derived) at residues 637-650, an immunoglobulin CH2 domain (human IgG1-derived) at residues 651-760, an immunoglobulin CH3 domain (human IgG1-derived) at residues 761-867. The exemplary HER2-Seldeg of SEQ ID NO: 4 has mutations that increase FcRn binding at residues 672, 674, 676, 853 and 854, arginine mutations at residues 656 and 748, and 'knobs-into-holes' mutations at residues 769 and 814. The cysteine residue (640) that usually pairs with an immunoglobulin light chain is mutated to serine. The amino acid residue numbers referred to in SEQ ID NO: 4 are those of the protein sequence, and do not refer to the EU numbering convention.

The DNA sequence of SEQ ID NO: 5 is of a polynucleotide encoding an exemplary Fc fragment (SEQ ID NO: 6), having mutations to increase FcRn binding, knobs-into-holes mutations and arginine mutations. The fusion protein of SEQ ID NO: 6 is configured, for example, for heterodimer formation with the MOG-Seldeg (SEQ ID NO: 2) or HER2-Seldeg (SEQ ID NO: 4) fusion.

In particular, the amino acid sequence of the exemplary Fc fragment of SEQ ID NO: 6 has, in order from N- to C-terminus, an immunoglobulin hinge (human IgG1-derived) at residues 1-16, an immunoglobulin CH2 domain (human IgG1-derived) at residues 17-126, an immunoglobulin C113 domain (human IgG1l-derived) at residues 127-233. The exemplary Fc fragment of SEQ ID NO: 6 has mutations that increase FcRn binding at residues 38, 40, 42, 219 and 220, arginine mutations at residues 22 and 114, and 'knobs-into-holes' mutations at residues 150 and 191. The cysteine residue (6) that usually pairs with an immunoglobulin light chain is mutated to serine. The amino acid residue numbers referred to in SEQ ID NO: 6 are those of the protein sequence, and do not refer to the EU numbering convention.

The DNA sequence of SEQ ID NO: 7 is of a polynucleotide encoding an exemplary MOG-Seldeg-PS fusion having knobs-into-holes mutations and arginine mutations, and the corresponding amino acid sequence of the encoded fusion protein is SEQ ID NO: 8.

In particular, the amino acid sequence of the exemplary MOG-Seldeg-PS fusion of SEQ ID NO: 8 has, in order from N- to C-terminus, residues 1-117 of mMOG, a first linker at residues 118-122, an immunoglobulin hinge (human IgG1-derived) at residues 123-138, an immunoglobulin C12 domain (human IgG1-derived) at residues 139-248, an immunoglobulin C13 domain (human IgG1-derived) at residues 249-355. The exemplary MOG-Seldeg-PS of SEQ ID NO: 8 has arginine mutations at residues 144 and 236, and 'knobs-into-holes' mutations at residues 257 and 302. The cysteine residue (128) that pairs with an immunoglobulin light chain is mutated to serine Residues 141-266 of the C2A PS-binding domain of synaptotagmin (Syt1) (shown as residues 361486) are fused to the C-terminus of the CH3 domain via a GGGGS (SEQ ID NO: 38) linker peptide (residues 356-360). The amino acid residue numbers referred to in SEQ ID NO: 8 are those of the protein sequence, and do not refer to the EU numbering convention.

The DNA sequence of SEQ ID NO: 9 is of a polynucleotide encoding an exemplary Fc-Syt1 fusion (SEQ ID NO: 10) having knobs-into-holes mutations and arginine mutations, configured for heterodimer formation, for example, with the MOG-Seldeg-PS (SEQ ID NO: 8).

In particular, the amino acid sequence of the exemplary Fc-Syt1 fusion of SEQ ID NO: 10 has, in order from N- to C-terminus, an immunoglobulin hinge (human IgG1-derived) at residues 1-16, an immunoglobulin C12 domain (human IgG1-derived) at residues 17-126, an immunoglobulin CH3 domain (human IgG1-derived) at residues 126-233. The exemplary Fc-Syt1 fusion protein of SEQ ID NO: 10 has arginine mutations at residues 22 and 114 and 'knobs-into-holes' mutations at residues 150 and 191. The cysteine residue (6) that usually pairs with an immunoglobulin light chain is mutated to serine Residues 141-266 of the C2A PS-binding domain of synaptotagmin (Syt1) (shown as residues 239-364) are fused to the C-terminus of the CH3 domain via a GGGGS (SEQ ID NO: 38) linker peptide (residues 234-238). The amino acid residue numbers referred to in SEQ ID NO: 10 are those of the protein sequence, and do not refer to the EU numbering convention.

The DNA sequence of SEQ ID NO: 11 is of a polynucleotide encoding an exemplary MOG-Seldeg-PS fusion (SEQ ID NO: 12) having knobs-into-holes mutations, electrostatic steering mutations and arginine mutations.

In particular, the amino acid sequence of the exemplary MOG-Seldeg-PS fusion of SEQ ID NO: 12 has, in order from N- to C-terminus, residues 1-117 of mMOG, a first linker at residues 118-122, an immunoglobulin hinge (human IgG1-derived) at residues 123-138, an immunoglobulin C112 domain (human IgG1-derived) at residues 139-248, an immunoglobulin C13 domain (human IgG1-derived) at residues 249-355. The exemplary MOG-Seldeg-PS of SEQ ID NO: 12 has arginine mutations at residues 144 and 236, electrostatic steering mutations at residues 300 and 317 and 'knobs-into-holes' mutations at residues 257 and 302. The cysteine residue (128) that pairs with an immunoglobulin light chain is mutated to serine Residues 141-266 of the C2A PS-binding domain of synaptotagmin (Syt1) (shown as residues 361-486) are fused to the C-terminus of the C13 domain via a GGGS linker peptide (residues 356-360). The amino acid residue numbers referred to in SEQ ID NO: 12 are those of the protein sequence, and do not refer to the EU numbering convention.

The DNA sequence of SEQ ID NO: 13 is of a polynucleotide encoding an exemplary Fc-Syt1 fusion (SEQ ID NO: 14) having knobs-into-holes mutations, electrostatic steering mutations and arginine mutations, configured, for example, for heterodimer formation with the MOG-Seldeg-PS (SEQ ID NO: 12).

In particular, the amino acid sequence of the exemplary Fc-Syt1 fusion protein of SEQ ID NO: 14 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233. The exemplary MOG-Seldeg-PS of SEQ ID NO: 14 has arginine mutations at residues 22 and 114, electrostatic steering mutations at residues 143 and 185 and 'knobs-into-holes' mutations at residues 150 and 191. The cysteine residue (6) that pairs with an immunoglobulin light chain is mutated to serine. Residues 141-266 of the C2A PS-binding domain of synaptotagmin (Syt1) (shown as residues 239-364) are fused to the C-terminus of the CH3 domain via a GGGGS (SEQ ID NO: 38) linker peptide (residues 234-238) The amino acid residue numbers referred to in SEQ ID NO: 14 are those of the protein sequence, and do not refer to the EU numbering convention.

The DNA sequence of SEQ ID NO: 15 is of a polynucleotide encoding an exemplary MOG-Seldeg-TfR fusion protein (SEQ ID NO: 16) comprising a TfR-specific antibody heavy chain with knobs into holes mutations.

In particular, the amino acid sequence of the exemplary TfR-specific antibody heavy chain-MOG fusion (MOG-Seldeg-TfR) of SEQ ID NO: 16 has, in order from N- to C-terminus, a TfR-specific VH domain at residues 1-116, an immunoglobulin CH1 domain (human IgG1-derived) at residues 117-213, an immunoglobulin hinge (human IgG1-derived) at residues 214-229, an immunoglobulin CH2 domain (human IgG1-derived) at residues 230-339, an immunoglobulin CH3 domain (human IgG1-derived) at residues 340-446. The exemplary TfR-specific antibody heavy chain of SEQ ID NO: 16 has 'knobs-into-holes' mutations at residues 348 and 393. Residues 1-117 of mMOG (shown as residues 452-568) are fused to the C-terminus of the C13 domain via a GGGGS (SEQ ID NO: 38) linker peptide (residues 447-451). The amino acid residue numbers referred to in SEQ ID NO: 16 are those of the protein sequence, and do not refer to the EU numbering convention.

The DNA sequence of SEQ ID NO: 17 is of a polynucleotide encoding an exemplary TfR-specific antibody heavy chain. The encoded fusion protein (SEQ ID NO: 18) having knobs into holes mutations is configured, for example, for heterodimer formation with the MOG-Seldeg-TfR fusion (SEQ ID NO: 16).

In particular, the amino acid sequence of the exemplary TfR-specific antibody heavy chain of SEQ ID NO: 18 for heterodimer formation with the TfR-specific heavy chain-MOG fusion (SEQ ID NO: 16) has, in order from N- to C-terminus, of a TfR-specific VH domain at residues 1-116, an immunoglobulin CH1 domain (human IgG1-derived) at residues 117-213, an immunoglobulin hinge (human IgG1-derived) at residues 214-229 an immunoglobulin CH2 domain (human IgG1-derived) at residues 230-339, an immunoglobulin CH3 domain (human IgG1-derived) at residues 340-446. The exemplary TfR-specific antibody heavy chain of SEQ ID NO: 18 has 'knobs-into-holes' mutations at residues 363 and 404. The amino acid residue numbers referred to in SEQ ID NO: 18 are those of the protein sequence, and do not refer to the EU numbering convention.

The DNA sequence of SEQ ID NO: 19 is of a polynucleotide encoding an exemplary light chain of a TfR-specific antibody (SEQ ID NO: 20) and is configured, for example, for heterodimer formation with the MOG-Seldeg-TfR fusion (SEQ ID NO: 16) and TfR-specific antibody heavy chain (SEQ ID NO: 18).

In particular, the amino acid sequence of the exemplary TfR-specific antibody light chain of SEQ ID NO: 20 has, in order from N- to C-terminus a TfR-specific VL domain at residues 1-107, and an immunoglobulin CL domain (human Cκ) at residues 108-213. The amino acid residue numbers referred to in SEQ ID NO: 20 are those of the protein sequence, and do not refer to the EU numbering convention.

The DNA sequence of SEQ ID NO: 21 is of a polynucleotide encoding an exemplary MOG-Seldeg-TfR fusion protein (SEQ ID NO: 22) having a TfR-specific antibody heavy chain with arginine mutations, and knobs-into-holes mutations.

In particular, the amino acid sequence of the exemplary TfR-specific antibody heavy chain-MOG fusion (MOG-Seldeg-TfR) of SEQ ID NO: 22 has, in order from N- to C-terminus, a TfR-specific VH domain at residues 1-116, an immunoglobulin CH1 domain (human IgG1-derived) at residues 117-213, an immunoglobulin hinge (human IgG1-derived) at residues 214-229, an immunoglobulin CH2 domain (human IgG1-derived) at residues 230-339, an immunoglobulin CH3 domain (human IgG1-derived) at residues 340-446. The exemplary TfR-specific antibody heavy chain of SEQ ID NO: 22 has arginine mutations at residues 235 and 327, and 'knobs-into-holes' mutations at residues 348 and 393. Residues 1-117 of mMOG (shown as residues 452-568) are fused to the C-terminus of the C311 domain via a GGGGS (SEQ ID NO: 38) linker peptide (residues 447-451). The amino acid residue numbers referred to in SEQ ID NO: 22 are those of the protein sequence, and do not refer to the EU numbering convention.

The DNA sequence of SEQ ID NO: 23 is of a polynucleotide encoding an exemplary TfR-specific antibody heavy chain (SEQ ID NO: 24) having arginine mutations, and knobs-into-holes mutations, and is configured, for example, for heterodimer formation with the MOG-Seldeg-TfR fusion (SEQ ID NO: 22).

In particular, the amino acid sequence of the exemplary TfR-specific antibody heavy chain of SEQ ID NO: 24 has, in order from N- to C-terminus, a TfR-specific VH domain at residues 1-116, an immunoglobulin CH1 domain (human IgG1-derived) at residues 117-213, an immunoglobulin hinge (human IgG1-derived) at residues 214-229 an immunoglobulin CH2 domain (human IgG1-derived) at residues 230-339, an immunoglobulin CH3 domain (human IgG1-derived) at residues 340-446. The TfR-specific antibody heavy chain of SEQ ID NO: 24 has arginine mutations at residues 235 and 327, and 'knobs-into-holes' mutations at residues 363 and 404). The amino acid residue numbers referred to in SEQ ID NO: 24 are those of the protein sequence, and do not refer to the EU numbering convention.

The DNA sequence of SEQ TD NO: 25 is of a polynucleotide encoding an exemplary HER2-Seldeg fusion protein (SEQ ID NO: 26) having mutations to increase FcRn binding, and knobs-into-holes mutations.

In particular, the amino acid sequence of the exemplary variant HER2-Seldeg of SEQ ID NO: 26 forms a fusion protein having, in order from N- to C-terminus, residues 1-630 of HER2, a first linker at residues 631-636, an immunoglobulin hinge (human IgG1-derived) at residues 637-650, an immunoglobulin CH2 domain (human IgG1-derived) at residues 651-760, an immunoglobulin C13 domain (human IgG1-derived) at residues 761-867. The HER2-Seldeg of SEQ ID NO: 26 has mutations that increase FcRn binding at residues 672, 674, 676, 853 and 854, and 'knobs-into-holes' mutations at residues 769 and 814. The cysteine residue (640) that usually pairs with an immunoglobulin light chain is mutated to serine. The amino acid residue numbers referred to in SEQ ID NO: 26 are those of the protein sequence, and do not refer to the EU numbering convention.

The DNA sequence of SEQ ID NO: 27 is of a polynucleotide encoding an exemplary Fc fragment (SEQ ID NO: 28) having mutations to increase FcRn binding, and knobs-into-holes mutations, and is configured, for example, for heterodimer formation with the HER2-Seldeg (SEQ ID NO: 26).

In particular, the amino acid sequence of the exemplary variant Fc fragment of SEQ ID NO: 28 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233. The variant Fc fragment of SEQ ID NO: 28 has mutations that increase FcRn binding at residues 38, 40, 42, 219 and 220, and 'knobs-into-holes' mutations at residues 150 and 191. The cysteine residue (6) that usually pairs with an immunoglobulin light chain is mutated to serine. The amino acid residue numbers referred to in SEQ ID NO: 28 are those of the protein sequence, and do not refer to the EU numbering convention.

The DNA sequence of SEQ ID NO: 29 is of a polynucleotide encoding an exemplary prostate-specific membrane antigen (PSMA)-Seldeg fusion protein (SEQ ID NO: 30) having mutations to increase FcRn binding, knobs-into-holes mutations and arginine mutations. This fusion protein will form heterodimers, for example, with an exemplary Fc fragment (SEQ ID NO: 6).

In particular, the amino acid sequence of the exemplary variant PSMA-Seldeg of SEQ ID NO: 30 forms a fusion protein having, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233 fused at the C-terminus via a linker at residues 234-238 to the extracellular domain (residues 239-945) of PSMA The variant PSMA-Seldeg of SEQ ID NO: 30 has mutations that increase FcRn binding at residues 38, 40, 42, 219 and 220, arginine mutations at residues 22 and 114, and 'knobs-into-holes' mutations at residues 135 and 180. The cysteine residue (6) that usually pairs with an immunoglobulin light chain is mutated to serine. The amino acid residue numbers referred to in SEQ ID NO: 30 are those of the protein sequence, and do not refer to the EU numbering convention.

The DNA sequence of SEQ ID NO: 31 is of a polynucleotide encoding an exemplary GAD65-Seldeg fusion protein (SEQ ID NO: 32) having mutations to increase FcRn binding, knobs-into-holes mutations and arginine mutations. This fusion protein will form heterodimers, for example, with an exemplary Fc fragment (SEQ ID NO: 6).

In particular, the amino acid sequence of the exemplary variant GAD65-Seldeg of SEQ ID NO: 32 forms a fusion protein having, in order from N- to C-terminus, residues 1-585 of human glutamic acid carboxylase 65 (GAD6S), a first linker at residues 586-590, an immunoglobulin hinge (human IgG1-derived) at residues 591-606, an immunoglobulin CH2 domain (human IgG1-derived) at residues 607-716, an immunoglobulin CH3 domain (human IgG1-derived) at residues 717-823. The variant GAD65-Seldeg of SEQ ID NO: 32 has mutations that increase FcRn binding at residues 628, 630, 632, 809 and 810, arginine mutations at residues 612 and 704, and 'knobs-into-holes' mutations at residues 725 and 770. The cysteine residue (596) that usually pairs with an immunoglobulin light chain is mutated to serine. The amino acid residue numbers referred to in SEQ ID NO: 32 are those of the protein sequence, and do not refer to the EU numbering convention.

The DNA sequence of SEQ ID NO: 33 is of a polynucleotide encoding an exemplary aquaporin 4-Seldeg fusion protein (SEQ ID NO: 34) having mutations to increase FcRn binding, knobs-into-holes mutations and arginine mutations. This fusion protein will form heterodimers, for example, with an exemplary Fc fragment (SEQ ID NO: 6).

In particular, the amino acid sequence of the exemplary variant aquaporin 4 (AQP4)-Seldeg of SEQ ID NO: 34 forms a fusion protein having, in order from N- to C-terminus, residues 1-323 of human aquaporin 4, a first linker at residues 324-328, an immunoglobulin hinge (human IgG1-derived) at residues 329-344, an immunoglobulin CH2 domain (human IgG1-derived) at residues 345-454, an immunoglobulin CH3 domain (human IgG1-derived) at residues 455-561. The variant AQP4-Seldeg of SEQ ID NO: 34 has mutations that increase FcRn binding at residues 366, 368, 370, 547,548, arginine mutations at residues 350 and 442, and 'knobs-into-holes' mutations at residues 463 and 508. The cysteine residue (334) that usually pairs with an immunoglobulin light chain is mutated to serine. The amino acid residue numbers referred to in SEQ ID NO: 34 are those of the protein sequence, and do not refer to the EU numbering convention.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A Seldeg comprising:
   (A) a targeting component, having a protein or a protein fragment configured to specifically bind to a cell surface receptor or a cell surface molecule; wherein said protein or protein fragment is selected from the group consisting of:
   (1) an antibody Fc fragment, which is
      (i) engineered to have an increased binding affinity for FcRn at a pH greater than 6.8 and less than 7.5; and
      (ii) has a reduced binding affinity for FcγRs and/or complement (C1q), compared with a wild-type Fc fragment;
   (2) an antibody specific for a cell-surface ligand, wherein the Fc fragment of said antibody is engineered to have a reduced binding affinity for FcγRs and/or complement (C1q), compared with a wild-type Fc fragment;
   and
   (3) a ligand for a cell-surface receptor, wherein said ligand is fused to an antibody Fc fragment which is engineered to have a reduced binding affinity for FcγRs and/or complement (C1q), compared with a wild-type Fc fragment;
   and
   (B) a monovalent antigen component, having a single molecule of an antigen, antigen fragment or antigen mimetic configured to specifically bind a target antigen-specific antibody;
   wherein the targeting component is fused directly or indirectly to the antigen component, and wherein said protein or protein fragment comprises an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 20, SEQ ID NO: 22, SEQ ID NO: 24, SEQ ID NO: 30, SEQ ID NO: 32, SEQ ID NO: 34; and a sequence having at least 95% identity thereto.

2. The Seldeg of claim 1, comprising at least a first targeting component and a second targeting component, wherein the protein or protein fragment of the first targeting component is configured to bind to a different cell surface receptor or a different cell surface molecule than the protein or protein fragment of the second targeting component.

3. The Seldeg of claim 2, wherein the targeting protein component comprises a heterodimer of two immunoglobulin Fc fragments in which one immunoglobulin Fc fragment of the heterodimer is fused to the antigen component and the other immunoglobulin Fc fragment is not.

4. The Seldeg of claim 1, wherein the antigen component is fused to one immunoglobulin Fc fragment at an N-terminus or a C-terminus of a hinge-CH2-CH3 domain of the immunoglobulin Fc fragment.

5. The Seldeg of claim 1 wherein said protein or protein fragment comprises a combination selected from the group consisting of i) SEQ ID NO: 2 plus SEQ ID NO: 6, ii) SEQ ID NO: 4 plus SEQ ID NO: 6, iii) SEQ ID NO: 8 plus SEQ ID NO: 10, iv) SEQ ID NO: 12 plus SEQ ID NO: 14, v) SEQ ID NO: 20 plus SEQ ID NO: 22 plus SEQ ID NO: 24, vi) SEQ ID NO: 30 plus SEQ ID NO: 6, vii) SEQ ID NO: 32 plus SEQ ID NO: 6, viii) SEQ ID NO: 34 plus SEQ ID NO: 6, and a sequence having at least 95% identity thereto.

6. The Seldeg of claim 1 wherein:
the target antigen specific antibody is an anti-MOG antibody;
the targeting component comprises a heterodimer of
(i) residues 1-117 of MOG linked either directly or via a linker to an immunoglobulin Fc fragment; and
(ii) an immunoglobulin Fc fragment;
wherein the immunoglobulin Fc fragment is derived from IgG1 and comprises mutations of L234A, L235A, P329G (EU numbering system) to reduce FcγR and C1q binding and M252Y, S254T, T256E, H433K, N434F (EU numbering system) to increase FcRn binding;
and wherein component (i) of the heterodimer has at least 95% sequence identity to SEQ ID NO: 2 and component (ii) of the heterodimer has at least 95% sequence identity to SEQ ID NO: 6.

7. A method of depleting target antigen-specific antibody from a patient, the method comprising:
administering to the patient a Seldeg according to claim 1 in an amount sufficient to remove at least 50% of the target antigen-specific antibody from a circulation or a target tissue in the patient.

8. The method of claim 7, comprising administering the Seldeg in an amount sufficient to remove at least 50% of the target antigen-specific antibody from the circulation or the target tissue in the patient within 24 hours of administration.

9. The method of claim 7, comprising administering the Seldeg in an amount sufficient to remove at least 90% of the target antigen-specific antibody from the circulation or the target tissue in the patient within 48 hours of administration.

10. The method of claim 7, comprising administering the Seldeg in an amount sufficient to remove at least 50% of the target antigen-specific antibody from the circulation or the target tissue in the patient within 48 hours of administration.

11. The method of claim 7, wherein the Seldeg removes less than 10% of non-target antibodies in the circulation or in the tissue targeted by the target antigen-specific antibody.

12. The method of claim 7, wherein the Seldeg removes an amount of non-targeted antibodies in the circulation or in the target tissue of the patient that does not cause a clinically adverse effect in the patient.

13. The method of claim 7, wherein the Seldeg removes less than 1% of non-target antibodies in the circulation or in a tissue targeted by the target antigen-specific antibody.

14. The method of claim 7, wherein the Seldeg causes degradation of the target antigen-specific antibody by a cell expressing the cell surface receptor or cell surface molecule.

15. The method of claim 7, wherein the Seldeg is administered to a patient with an autoimmune disease and the target antigen-specific antibody specifically binds to an autoantigen.

16. The method of claim 7, wherein the Seldeg is administered to a patient receiving a transplanted organ and the target antigen-specific antibody specifically binds to an antigen on the transplanted organ.

17. The method of claim 7, wherein the Seldeg is administered to increase contrast during tumor imaging and the target antigen-specific antibody specifically binds to a tumor antigen.

18. The method of claim 7, wherein the target-specific antibody has been administered to the patient.

19. The method of claim 7, wherein the Seldeg is administered prior to the delivery of a therapeutic agent, if the patient has antibodies specific for the therapeutic agent, and the Seldeg is configured to target the antibodies specific for the therapeutic agent.

20. The method of claim 7, wherein the Seldeg is administered to improve contrast in diagnostic imaging.

* * * * *

SEQUENCE LISTING

```
<160> NUMBER OF SEQ ID NOS: 38

<210> SEQ ID NO 1
<211> LENGTH: 1065
<212> TYPE: DNA
<213> ORGANISM: Homo sapiens

<400> SEQUENCE: 1
ggacaattca gagtgatagg accagggtat cccatccggg ctttagttgg ggatgaagca      60
```

-continued

```
gagctgccgt gccgcatctc tcctgggaaa aatgccacgg gcatggaggt gggttggtac    120
cgttctccct tctcaagagt ggttcacctc taccgaaatg caaggacca agatgcagag    180 caagcacctg aataccgggg acgcacagag cttctgaaag agactatcag tgagggaaag    240
gttaccctta ggattcagaa cgtgagattc tcagatgaag gaggctacac ctgcttcttc    300
agagaccact cttaccaaga gaggcagca atggagttga agtggaaga tggaggcggt      360 ggatcagttg agcccaaatc ttctgacaaa actcacacat gcccaccgtg cccagcacct    420
gaactcctga ggggaccgtc agtcttcctc ttccccccaa acccaagga caccctctac     480 atcactcggg aacctgaggt cacatgcgtg gtggtggacg tgagccacga agaccctgag    540
gtcaagttca actggtacgt ggacggcgtg gaggtgcata atgccaagac aaagccgcgg    600
gaggagcagt acaacagcac gtaccgtgtg gtcagcgtcc tcaccgtcct gcaccaggac    660
tggctgaatg caaggagta caagtgcaag gtctccaaca aagcccgccc agcccccatc    720
gagaaaacca tctccaaagc caagggcag ccccgagaac cacaggtgac caccctgccc     780
ccatcccggg atgagctgac caagaaccag gtcagcctga cctgcctggt caaaggcttc    840
tatcccagcg acatcgccgt ggagtgggag agcaatgggc agccggagaa caactacaag    900
accttccctc ccgtgctgga ctccgacggc tccttcttcc tctacagcaa gctcaccgtg    960
gacaagagca ggtggcagca ggggaacgtc ttctcatgct ctgtgatgca tgaggctctg   1020
aaattccact acacgcagaa gagcctctcc ctgtctccgg gtaaa                   1065
```

<210> SEQ ID NO 2
<211> LENGTH: 355
<212> TYPE: PRT
<213> ORGANISM: Homo sapiens

<400> SEQUENCE: 2

```
Gly Gln Phe Arg Val Ile Gly Pro Gly Tyr Pro Ile Arg Ala Leu Val
1               5                   10                  15

Gly Asp Glu Ala Glu Leu Pro Cys Arg Ile Ser Pro Gly Lys Asn Ala
            20                  25                  30

Thr Gly Met Glu Val Gly Trp Tyr Arg Ser Pro Phe Ser Arg Val Val
        35                  40                  45

His Leu Tyr Arg Asn Gly Lys Asp Gln Asp Ala Glu Gln Ala Pro Glu
    50                  55                  60

Tyr Arg Gly Arg Thr Glu Leu Leu Lys Glu Thr Ile Ser Glu Gly Lys
65                  70                  75                  80

Val Thr Leu Arg Ile Gln Asn Val Arg Phe Ser Asp Glu Gly Gly Tyr
                85                  90                  95

Thr Cys Phe Phe Arg Asp His Ser Tyr Gln Glu Glu Ala Ala Met Glu
            100                 105                 110

Leu Lys Val Glu Asp Gly Gly Gly Ser Val Glu Pro Lys Ser Ser
        115                 120                 125

Asp Lys Thr His Thr Cys Pro Pro Cys Pro Ala Pro Glu Leu Leu Arg
    130                 135                 140

Gly Pro Ser Val Phe Leu Phe Pro Pro Lys Pro Lys Asp Thr Leu Tyr
145                 150                 155                 160

Ile Thr Arg Glu Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190
```

His Asn Ala Lys Thr Lys Pro Arg Glu Glu Gln Tyr Asn Ser Thr Tyr
            195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Arg Pro Ala Pro Ile
225                 230                 235                 240

Glu Lys Thr Ile Ser Lys Ala Lys Gly Gln Pro Arg Glu Pro Gln Val
                245                 250                 255

Thr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Phe Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu Lys Phe His Tyr Thr Gln Lys Ser Leu Ser Leu Ser
            340                 345                 350

Pro Gly Lys
        355

<210> SEQ ID NO 3
<211> LENGTH: 2601
<212> TYPE: DNA
<213> ORGANISM: Homo sapiens

<400> SEQUENCE: 3

```
acccaagtgt gcaccggcac agacatgaag ctgcggctcc ctgccagtcc cgagacccac        60
ctggacatgc tccgccacct ctaccagggc tgccaggtgg tgcagggaaa cctggaactc       120
acctacctgc ccaccaatgc cagcctgtcc ttcctgcagg atatccagga ggtgcagggc       180
tacgtgctca tcgctcacaa ccaagtgagg caggtcccac tgcagaggct gcggattgtg       240
cgaggcaccc agctctttga ggacaactat gccctgccg tgctagacaa tggagacccg       300
ctgaacaata ccacccctgt cacaggggcc tccccaggag cctgcgggga gctgcagctt       360
cgaagcctca cagagatctt gaaggagggg gtcttgatcc agcggaaccc ccagctctgc       420
taccaggaca cgattttgtg aaggacatc ttccacaaga caaccagct ggctctcaca        480
ctgatagaca ccaaccgctc tcgggcctgc cacccctgtt ctccgatgtg taagggctcc       540
cgctgctggg gagagagttc tgaggattgt cagagcctga cgcgcactgt ctgtgccggt       600
ggctgtgccc gctgcaaggg gccactgccc actgactgct ccatgagca gtgtgctgcc        660
ggctgcacgg gccccaagca ctctgactgc ctggcctgcc tccacttcaa ccacagtggc       720
atctgtgagc tgcactgccc agccctggtc acctacaaca cagacacgtt tgagtccatg       780
cccaatcccg agggccggta cattcggc gccagctgtg tgactgcctg tcctacaac          840
taccttttcta cggacgtggg atcctgcacc ctcgtctgcc cctgcacaa ccaagaggtg       900
acagcagagg atgaacaca gcggtgtgag aagtgcagca gccctgtgc cgagtgtgc          960
tatggtctgg gcatggagca cttgcgagag gtgagggcag ttaccagtgc caatatccag      1020
gagtttgctg gctgcaagaa gatctttggg agcctggcat ttctgccgga gagctttgat      1080
ggggacccag cctccaacac tgccccgctc cagccagagc agctccaagt gtttgagact      1140
```

```
ctggaagaga tcacaggtta cctatacatc tcagcatggc cggacagcct gcctgacctc      1200
agcgtcttcc agaacctgca agtaatccgg ggacgaattc tgcacaatgg cgcctactcg      1260
ctgaccctgc aagggctggg catcagctgg ctggggctgc gctcactgag ggaactgggc      1320
agtggactgg ccctcatcca ccataacacc cacctctgct tcgtgcacac ggtgccctgg      1380
gaccagctct ttcggaaccc gcaccaagct ctgctccaca ctgccaaccg gccagaggac      1440
gagtgtgtgg gcgagggcct ggcctgccac cagctgtgcg cccgagggca ctgctggggt      1500
ccagggccca cccagtgtgt caactgcagc cagttccttc ggggccagga gtgcgtggag      1560
gaatgccgag tactgcaggg gctccccagg gagtatgtga atgccaggca ctgtttgccg      1620
tgccaccctg agtgtcagcc ccagaatggc tcagtgacct gttttggacc ggaggctgac      1680
cagtgtgtgg cctgtgccca ctataaggac cctcccttct gcgtggcccg ctgccccagc      1740
ggtgtgaaac ctgacctctc ctacatgccc atctggaagt tccagatgaa ggagggcgca      1800
tgccagcctt gccccatcaa ctgcacccac tcctgtgtgg acctggatga caagggctgc      1860
cccgccgagc agagagccag ccctctgacg attgaaggcc gcatggatcc caaatcttct      1920
gacaaaactc acacatgccc accgtgccca gcacctgaac tcctgagggg accgtcagtc      1980
ttcctcttcc ccccaaaacc caaggacacc ctctacatca ctcgggaacc tgaggtcaca      2040
tgcgtggtgg tggacgtgag ccacgaagac cctgaggtca agttcaactg gtacgtggac      2100
ggcgtggagg tgcataatgc caagacaaag ccgcgggagg agcagtacaa cagcacgtac      2160
cgtgtggtca gcgtcctcac cgtcctgcac caggactggc tgaatggcaa ggagtacaag      2220
tgcaaggtct ccaacaaagc cgcccagcc cccatcgaga aaaccatctc caaagccaaa      2280
gggcagcccc gagaaccaca ggtgaccacc ctgccccat cccgggatga gctgaccaag      2340
aaccaggtca gcctgacctg cctggtcaaa ggcttctatc ccagcgacat cgccgtggag      2400
tgggagagca atgggcagcc ggagaacaac tacaagacct cccctcccgt gctggactcc      2460
gacggctcct tcttcctcta cagcaagctc accgtggaca agagcaggtg gcagcagggg      2520
aacgtcttct catgctctgt gatgcatgag gctctgaaat ccactacac gcagaagagc      2580 ctctccctgt ctcctggtaa a                                                2601
```

<210> SEQ ID NO 4
<211> LENGTH: 867
<212> TYPE: PRT
<213> ORGANISM: Homo sapiens

<400> SEQUENCE: 4

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110
```

-continued

```
Gly Gly Leu Arg Glu Leu Gln Leu Arg Ser Leu Thr Glu Ile Leu Lys
            115                 120                 125
Gly Gly Val Leu Ile Gln Arg Asn Pro Gln Leu Cys Tyr Gln Asp Thr
        130                 135                 140
Ile Leu Trp Lys Asp Ile Phe His Lys Asn Asn Gln Leu Ala Leu Thr
145                 150                 155                 160
Leu Ile Asp Thr Asn Arg Ser Arg Ala Cys His Pro Cys Ser Pro Met
                165                 170                 175
Cys Lys Gly Ser Arg Cys Trp Gly Glu Ser Ser Glu Asp Cys Gln Ser
            180                 185                 190
Leu Thr Arg Thr Val Cys Ala Gly Gly Cys Ala Arg Cys Lys Gly Pro
        195                 200                 205
Leu Pro Thr Asp Cys Cys His Glu Gln Cys Ala Ala Gly Cys Thr Gly
    210                 215                 220
Pro Lys His Ser Asp Cys Leu Ala Cys Leu His Phe Asn His Ser Gly
225                 230                 235                 240
Ile Cys Glu Leu His Cys Pro Ala Leu Val Thr Tyr Asn Thr Asp Thr
                245                 250                 255
Phe Glu Ser Met Pro Asn Pro Glu Gly Arg Tyr Thr Phe Gly Ala Ser
            260                 265                 270
Cys Val Thr Ala Cys Pro Tyr Asn Tyr Leu Ser Thr Asp Val Gly Ser
        275                 280                 285
Cys Thr Leu Val Cys Pro Leu His Asn Gln Glu Val Thr Ala Glu Asp
    290                 295                 300
Gly Thr Gln Arg Cys Glu Lys Cys Ser Lys Pro Cys Ala Arg Val Cys
305                 310                 315                 320
Tyr Gly Leu Gly Met Glu His Leu Arg Glu Val Arg Ala Val Thr Ser
                325                 330                 335
Ala Asn Ile Gln Glu Phe Ala Gly Cys Lys Lys Ile Phe Gly Ser Leu
            340                 345                 350
Ala Phe Leu Pro Glu Ser Phe Asp Gly Asp Pro Ala Ser Asn Thr Ala
        355                 360                 365
Pro Leu Gln Pro Glu Gln Leu Gln Val Phe Glu Thr Leu Glu Glu Ile
    370                 375                 380
Thr Gly Tyr Leu Tyr Ile Ser Ala Trp Pro Asp Ser Leu Pro Asp Leu
385                 390                 395                 400
Ser Val Phe Gln Asn Leu Gln Val Ile Arg Gly Arg Ile Leu His Asn
                405                 410                 415
Gly Ala Tyr Ser Leu Thr Leu Gln Gly Leu Gly Ile Ser Trp Leu Gly
            420                 425                 430
Leu Arg Ser Leu Arg Glu Leu Gly Ser Gly Leu Ala Leu Ile His His
        435                 440                 445
Asn Thr His Leu Cys Phe Val His Thr Val Pro Trp Asp Gln Leu Phe
    450                 455                 460
Arg Asn Pro His Gln Ala Leu Leu His Thr Ala Asn Arg Pro Glu Asp
465                 470                 475                 480
Glu Cys Val Gly Glu Gly Leu Ala Cys His Gln Leu Cys Ala Arg Gly
                485                 490                 495
His Cys Trp Gly Pro Gly Pro Thr Gln Cys Val Asn Cys Ser Gln Phe
            500                 505                 510
Leu Arg Gly Gln Glu Cys Val Glu Glu Cys Arg Val Leu Gln Gly Leu
        515                 520                 525
Pro Arg Glu Tyr Val Asn Ala Arg His Cys Leu Pro Cys His Pro Glu
```

```
Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
            565                 570                 575

Arg Cys Pro Ser Gly Val Lys Pro Asp Leu Ser Tyr Met Pro Ile Trp
        580                 585                 590

Lys Phe Pro Asp Glu Glu Gly Ala Cys Gln Pro Cys Pro Ile Asn Cys
    595                 600                 605

Thr His Ser Cys Val Asp Leu Asp Asp Lys Gly Cys Pro Ala Glu Gln
610                 615                 620

Arg Ala Ser Pro Leu Thr Ile Glu Gly Arg Met Asp Pro Lys Ser Ser
625                 630                 635                 640

Asp Lys Thr His Thr Cys Pro Pro Cys Pro Ala Pro Glu Leu Leu Arg
            645                 650                 655

Gly Pro Ser Val Phe Leu Phe Pro Pro Lys Pro Lys Asp Thr Leu Tyr
        660                 665                 670

Ile Thr Arg Glu Pro Glu Val Thr Cys Val Val Val Asp Val Ser His
    675                 680                 685

Glu Asp Pro Glu Val Lys Phe Asn Trp Tyr Val Asp Gly Val Glu Val
690                 695                 700

His Asn Ala Lys Thr Lys Pro Arg Glu Glu Gln Tyr Asn Ser Thr Tyr
705                 710                 715                 720

Arg Val Val Ser Val Leu Thr Val Leu His Gln Asp Trp Leu Asn Gly
            725                 730                 735

Lys Glu Tyr Lys Cys Lys Val Ser Asn Lys Ala Arg Pro Ala Pro Ile
        740                 745                 750

Glu Lys Thr Ile Ser Lys Ala Lys Gly Gln Pro Arg Glu Pro Gln Val
    755                 760                 765

Thr Thr Leu Pro Pro Ser Arg Asp Glu Leu Thr Lys Asn Gln Val Ser
770                 775                 780

Leu Thr Cys Leu Val Lys Gly Phe Tyr Pro Ser Asp Ile Ala Val Glu
785                 790                 795                 800

Trp Glu Ser Asn Gly Gln Pro Glu Asn Asn Tyr Lys Thr Phe Pro Pro
            805                 810                 815

Val Leu Asp Ser Asp Gly Ser Phe Phe Leu Tyr Ser Lys Leu Thr Val
        820                 825                 830

Asp Lys Ser Arg Trp Gln Gln Gly Asn Val Phe Ser Cys Ser Val Met
    835                 840                 845

His Glu Ala Leu Lys Phe His Tyr Thr Gln Lys Ser Leu Ser Leu Ser
850                 855                 860

Pro Gly Lys
865

<210> SEQ ID NO 5
<211> LENGTH: 699
<212> TYPE: DNA
<213> ORGANISM: Homo sapiens

<400> SEQUENCE: 5
gttgagccca aatcttctga caaaactcac acatgcccac cgtgcccagc acctgaactc      60
ctgaggggac cgtcagtctt cctcttcccc ccaaaaccca aggacaccct ctacatcact     120
cgggaacctg aggtcacatg cgtggtggtg gacgtgagcc acgaagaccc tgaggtcaag     180
```

-continued

```
ttcaactggt acgtggacgg cgtggaggtg cataatgcca agacaaagcc gcgggaggag    240
cagtacaaca gcacgtaccg tgtggtcagc gtcctcaccg tcctgcacca ggactggctg    300
aatggcaagg agtacaagtg caaggtctcc aacaaagccc gcccagcccc catcgagaaa    360
accatctcca aagccaaagg gcagccccga gaaccacagg tgtacaccct gcccccatcc    420
cgggatgagc tgaccaagaa ccaggtccac ctgacctgcc tggtcaaagg cttctatccc    480
agcgacatcg ccgtggagtg ggagagcaat gggcagccgg agaacaacta caagaccacg    540
cctcccgtgc tggactccga cggctccttc gccctctaca gcaagctcac cgtggacaag    600
agcaggtggc agcaggggaa cgtcttctca tgctccgtga tgcatgaggc tctgaaattc    660
cactacacgc agaagagcct ctccctgtct ccgggtaaa                           699
```

<210> SEQ ID NO 6
<211> LENGTH: 233
<212> TYPE: PRT
<213> ORGANISM: Homo sapiens

<400> SEQUENCE: 6

```
Val Glu Pro Lys Ser Ser Asp Lys Thr His Thr Cys Pro Pro Cys Pro
1               5                   10                  15

Ala Pro Glu Leu Leu Arg Gly Pro Ser Val Phe Leu Phe Pro Pro Lys
            20                  25                  30

Pro Lys Asp Thr Leu Tyr Ile Thr Arg Glu Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Arg Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val His Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Ala Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu Lys Phe His Tyr Thr Gln
    210                 215                 220

Lys Ser Leu Ser Leu Ser Pro Gly Lys
225                 230
```

<210> SEQ ID NO 7
<211> LENGTH: 1458
<212> TYPE: DNA
<213> ORGANISM: Homo sapiens

<400> SEQUENCE: 7

```
ggacaattca gagtgatagg accagggtat cccatccggg ctttagttgg ggatgaagca      60
gagctgccgt gccgcatctc tcctgggaaa aatgccacgg gcatggaggt gggttggtac     120
cgttctccct tctcaagagt ggttcacctc taccgaaatg gcaaggacca gatgcagag      180
caagcacctg aataccgggg acgcacagag cttctgaaag agactatcag tgagggaaag     240
gttacccctta ggattcagaa cgtgagattc tcagatgaag gaggctacac ctgcttcttc    300
agagaccact cttaccaaga agaggcagca atggagttga agtggaagat ggaggcggt      360
ggatcagttg agcccaaatc ttctgacaaa actcacacat gcccaccgtg cccagcacct    420
gaactcctga ggggaccgtc agtcttcctc ttccccccaa acccaaggac acccctcatg    480
atctcccgga cccctgaggt cacatgcgtg gtggtggacg tgagccacga agaccctgag    540
gtcaagttca actggtacgt ggacggcgtg gaggtgcata atgccaagac aaagccgcgg    600
gaggagcagt acaacagcac gtaccgtgtg gtcagcgtcc tcaccgtcct gcaccaggac    660
tggctgaatg gcaaggagta caagtgcaag gtctccaaca aagcccgccc agcccccatc    720
gagaaaacca tctccaaagc caagggcagc cccgagaac cacaggtgac caccctgccc    780
ccatcccggg atgagctgac caagaaccag gtcagcctga cctgcctggt caaaggcttc    840
tatcccagcg acatcgccgt ggagtgggag agcaatgggc agccggagaa caactacaag    900
accttccctc ccgtgctgga ctccgacggc tccttcttcc tctacagcaa gctcaccgtg    960
gacaagagca ggtggcagca ggggaacgtc ttctcatgct ctgtgatgca tgaggctctg   1020
cataaccact acacgcagaa gagcctctcc ctgtctccgg gtaaaggagg cggtggatca   1080
gagaaactgg gaaaacttca gtattcactg gattatgatt ccaaaataa ccagctgctg   1140
gtagggatca ttcaggctgc cgaactgccc gccttggaca tgggggcac atctgatcct   1200
tacgtgaaag tgtttctgct acctgataag aagaagaaat ttgagacaaa agtccaccga   1260
aaaaccctta atcctgtctt caatgagcaa tttactttca aggtaccata ctcggaattg   1320
ggtggcaaaa ccctagtgat ggctgtatat gattttgatc gtttctctaa gcatgacatc   1380
attggagaat ttaaagtccc tatgaacaca gtggattttg gccatgtaac tgaggaatgg   1440
cgtgacctgc aaagtgct                                                  1458
```

<210> SEQ ID NO 8
<211> LENGTH: 486
<212> TYPE: PRT
<213> ORGANISM: Homo sapiens

<400> SEQUENCE: 8

```
Gly Gln Phe Arg Val Ile Gly Pro Gly Tyr Pro Ile Arg Ala Leu Val
1               5                   10                  15

Gly Asp Glu Ala Glu Leu Pro Cys Arg Ile Ser Pro Gly Lys Asn Ala
            20                  25                  30

Thr Gly Met Glu Val Gly Trp Tyr Arg Ser Pro Phe Ser Arg Val Val
        35                  40                  45

His Leu Tyr Arg Asn Gly Lys Asp Gln Asp Ala Glu Gln Ala Pro Glu
    50                  55                  60

Tyr Arg Gly Arg Thr Glu Leu Leu Lys Glu Thr Ile Ser Glu Gly Lys
65                  70                  75                  80

Val Thr Leu Arg Ile Gln Asn Val Arg Phe Ser Asp Glu Gly Gly Tyr
                85                  90                  95

Thr Cys Phe Phe Arg Asp His Ser Tyr Gln Glu Glu Ala Ala Met Glu
            100                 105                 110
```

```
Leu Lys Val Glu Asp Gly Gly Gly Ser Val Glu Pro Lys Ser Ser
            115                 120                 125

Asp Lys Thr His Thr Cys Pro Pro Cys Pro Ala Pro Glu Leu Leu Arg
130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Arg Pro Ala Pro Ile
225                 230                 235                 240

Glu Lys Thr Ile Ser Lys Ala Lys Gly Gln Pro Arg Glu Pro Gln Val
                245                 250                 255

Thr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Phe Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Lys Gly Gly Gly Ser Glu Lys Leu Gly Lys Leu Gln Tyr
        355                 360                 365

Ser Leu Asp Tyr Asp Phe Gln Asn Asn Gln Leu Leu Val Gly Ile Ile
    370                 375                 380

Gln Ala Ala Glu Leu Pro Ala Leu Asp Met Gly Gly Thr Ser Asp Pro
385                 390                 395                 400

Tyr Val Lys Val Phe Leu Leu Pro Asp Lys Lys Lys Phe Glu Thr
                405                 410                 415

Lys Val His Arg Lys Thr Leu Asn Pro Val Phe Asn Glu Gln Phe Thr
            420                 425                 430

Phe Lys Val Pro Tyr Ser Glu Leu Gly Gly Lys Thr Leu Val Met Ala
        435                 440                 445

Val Tyr Asp Phe Asp Arg Phe Ser Lys His Asp Ile Ile Gly Glu Phe
    450                 455                 460

Lys Val Pro Met Asn Thr Val Asp Phe Gly His Val Thr Glu Glu Trp
465                 470                 475                 480

Arg Asp Leu Gln Ser Ala
                485

<210> SEQ ID NO 9
<211> LENGTH: 1092
<212> TYPE: DNA
<213> ORGANISM: Homo sapiens

<400> SEQUENCE: 9
```

```
gttgagccca aatcttctga caaaactcac acatgcccac cgtgcccagc acctgaactc    60
ctgagggac  cgtcagtctt cctcttcccc ccaaaaccca aggacaccct catgatctcc   120
cggacccctg aggtcacatg cgtggtggtg gacgtgagcc acgaagaccc tgaggtcaag   180
ttcaactggt acgtggacgg cgtggaggtg cataatgcca agacaaagcc gcgggaggag   240
cagtacaaca gcacgtaccg tgtggtcagc gtcctcaccg tcctgcacca ggactggctg   300
aatggcaagg agtacaagtg caaggtctcc aacaaagccc gcccagcccc catcgagaaa   360
accatctcca aagccaaagg gcagccccga gaaccacagg tgtacaccct gcccccatcc   420
cgggatgagc tgaccaagaa ccaggtcagc ctgacctgcc tggtcaaagg cttctatccc   480
agcgacatcg ccgtggagtg ggagagcaat gggcagccgg agaacaacta caagaccacg   540
cctcccgtgc tggactccga cggctccttc gccctctaca gcaagctcac cgtggacaag   600
agcaggtggc agcaggggaa cgtcttctca tgctccgtga tgcatgaggc tctgcacaac   660
cactacacgc agaagagcct ctccctgtct ccgggtaaag gaggcggtgg atcagagaaa   720
ctgggaaaac ttcagtattc actggattat gatttccaaa ataaccagct gctggtaggg   780
atcattcagg ctgccgaact gcccgccttg gacatggggg gcacatctga tccttacgtg   840
aaagtgtttc tgctacctga taagaagaag aaatttgaga caaaagtcca ccgaaaaacc   900
cttaatcctg tcttcaatga gcaatttact ttcaaggtac atactcgga  attgggtggc   960
aaaaccctag tgatggctgt atatgatttt gatcgtttct ctaagcatga catcattgga  1020
gaatttaaag tccctatgaa cacagtggat tttggccatg taactgagga atggcgtgac  1080
ctgcaaagtg ct                                                      1092
```

<210> SEQ ID NO 10
<211> LENGTH: 364
<212> TYPE: PRT
<213> ORGANISM: Homo sapiens

<400> SEQUENCE: 10

```
Val Glu Pro Lys Ser Ser Asp Lys Thr His Thr Cys Pro Pro Cys Pro
1               5                   10                  15

Ala Pro Glu Leu Leu Arg Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
        50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
                100                 105                 110

Ala Arg Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val His Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175
```

```
Tyr Lys Thr Thr Pro Val Leu Asp Ser Asp Gly Ser Phe Ala Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Gly Gly Gly Ser Glu Lys
225                 230                 235                 240

Leu Gly Lys Leu Gln Tyr Ser Leu Asp Tyr Asp Phe Gln Asn Asn Gln
                245                 250                 255

Leu Leu Val Gly Ile Ile Gln Ala Ala Glu Leu Pro Ala Leu Asp Met
            260                 265                 270

Gly Gly Thr Ser Asp Pro Tyr Val Lys Val Phe Leu Leu Pro Asp Lys
        275                 280                 285

Lys Lys Lys Phe Glu Thr Lys Val His Arg Lys Thr Leu Asn Pro Val
290                 295                 300

Phe Asn Glu Gln Phe Thr Phe Lys Val Pro Tyr Ser Glu Leu Gly Gly
305                 310                 315                 320

Lys Thr Leu Val Met Ala Val Tyr Asp Phe Asp Arg Phe Ser Lys His
                325                 330                 335

Asp Ile Ile Gly Glu Phe Lys Val Pro Met Asn Thr Val Asp Phe Gly
            340                 345                 350

His Val Thr Glu Glu Trp Arg Asp Leu Gln Ser Ala
                355                 360

<210> SEQ ID NO 11
<211> LENGTH: 1458
<212> TYPE: DNA
<213> ORGANISM: Homo sapiens

<400> SEQUENCE: 11
ggacaattca gagtgatagg accagggtat cccatccggg ctttagttgg ggatgaagca     60
gagctgccgt gccgcatctc tcctgggaaa aatgccacgg gcatggaggt gggttggtac   120
cgttctccct tctcaagagt ggttcacctc taccgaaatg caaggacca agatgcagag   180
caagcacctg aataccgggg acgcacagag cttctgaaag agactatcag tgagggaaag   240
gttacccttag ggattcagaa cgtgagattc tcagatgaag gaggctacac ctgcttcttc   300
agagaccact cttaccaaga gaggcagca atggagttga agtggaaga tggaggcggt   360
ggatcagttg agcccaaatc ttctgacaaa actcacacat gcccaccgtg cccagcacct   420
gaactcctga gggaccgtc agtcttcctc ttccccccaa aacccaagga caccctcatg   480
atctcccgga cccctgaggt cacatgcgtg gtggtggacg tgagccacga agaccctgag   540
gtcaagttca actggtacgt ggacggcgtg gaggtgcata atgccaagac aaagccgcgg   600
gaggagcagt acaacagcac gtaccgtgtg gtcagcgtcc tcaccgtcct gcaccaggac   660
tggctgaatg gcaaggagta caagtgcaag gtctccaaca aagcccgccc agcccccatc   720
gagaaaacca tctccaaagc caaagggcag ccccgagaac acaggtgac acccctgccc   780
ccatcccggg atgagctgac caagaaccag gtcagcctga cctgcctggt caaaggcttc   840
tatcccagcg acatcgccgt ggagtgggag agcaatgggc agccggagaa caactacgac   900
accttccctc ccgtgctgga ctccgacggc tccttcttcc tctacagcga cctcaccgtg   960
gacaagagca ggtggcagca ggggaacgtc ttctcatgct ctgtgatgca tgaggctctg  1020
```

```
cataaccact acacgcagaa gagcctctcc ctgtctccgg gtaaaggagg cggtggatca    1080
gagaaactgg gaaaacttca gtattcactg gattatgatt tccaaaataa ccagctgctg    1140
gtagggatca ttcaggctgc cgaactgccc gccttggaca tgggggggcac atctgatcct    1200 tacgtgaaag tgtttctgct acctgataag aagaagaaat ttgagacaaa agtccaccga    1260
aaaaccctta atcctgtctt caatgagcaa tttactttca aggtaccata ctcggaattg    1320
ggtggcaaaa ccctagtgat ggctgtatat gattttgatc gtttctctaa gcatgacatc    1380
attggagaat ttaaagtccc tatgaacaca gtggattttg gccatgtaac tgaggaatgg    1440
cgtgacctgc aaagtgct                                                  1458
```

<210> SEQ ID NO 12
<211> LENGTH: 486
<212> TYPE: PRT
<213> ORGANISM: Homo sapiens

<400> SEQUENCE: 12

```
Gly Gln Phe Arg Val Ile Gly Pro Gly Tyr Pro Ile Arg Ala Leu Val
1               5                   10                  15

Gly Asp Glu Ala Glu Leu Pro Cys Arg Ile Ser Pro Gly Lys Asn Ala
            20                  25                  30

Thr Gly Met Glu Val Gly Trp Tyr Arg Ser Pro Phe Ser Arg Val Val
        35                  40                  45

His Leu Tyr Arg Asn Gly Lys Asp Gln Asp Ala Glu Gln Ala Pro Glu
    50                  55                  60

Tyr Arg Gly Arg Thr Glu Leu Leu Lys Glu Thr Ile Ser Glu Gly Lys
65                  70                  75                  80

Val Thr Leu Arg Ile Gln Asn Val Arg Phe Ser Asp Glu Gly Gly Tyr
                85                  90                  95

Thr Cys Phe Phe Arg Asp His Ser Tyr Gln Glu Glu Ala Ala Met Glu
            100                 105                 110

Leu Lys Val Glu Asp Gly Gly Gly Ser Val Glu Pro Lys Ser Ser
        115                 120                 125

Asp Lys Thr His Thr Cys Pro Pro Cys Pro Ala Pro Glu Leu Leu Arg
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Arg Pro Ala Pro Ile
225                 230                 235                 240

Glu Lys Thr Ile Ser Lys Ala Lys Gly Gln Pro Arg Glu Pro Gln Val
                245                 250                 255

Thr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Asp Thr Phe Pro Pro
```

```
                290                 295                 300
Val Leu Asp Ser Asp Gly Ser Phe Phe Leu Tyr Ser Asp Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
                340                 345                 350

Pro Gly Lys Gly Gly Gly Ser Glu Lys Leu Gly Lys Leu Gln Tyr
                355                 360                 365

Ser Leu Asp Tyr Asp Phe Gln Asn Asn Gln Leu Leu Val Gly Ile Ile
                370                 375                 380

Gln Ala Ala Glu Leu Pro Ala Leu Asp Met Gly Gly Thr Ser Asp Pro
385                 390                 395                 400

Tyr Val Lys Val Phe Leu Leu Pro Asp Lys Lys Lys Phe Glu Thr
                405                 410                 415

Lys Val His Arg Lys Thr Leu Asn Pro Val Phe Asn Glu Gln Phe Thr
                420                 425                 430

Phe Lys Val Pro Tyr Ser Glu Leu Gly Gly Lys Thr Leu Val Met Ala
                435                 440                 445

Val Tyr Asp Phe Asp Arg Phe Ser Lys His Asp Ile Ile Gly Glu Phe
                450                 455                 460

Lys Val Pro Met Asn Thr Val Asp Phe Gly His Val Thr Glu Glu Trp
465                 470                 475                 480

Arg Asp Leu Gln Ser Ala
                485

<210> SEQ ID NO 13
<211> LENGTH: 1092
<212> TYPE: DNA
<213> ORGANISM: Homo sapiens

<400> SEQUENCE: 13
gttgagccca aatcttctga caaaactcac acatgcccac cgtgcccagc acctgaactc      60
ctgagggggac cgtcagtctt cctcttcccc ccaaaaccca aggacaccct catgatctcc     120
cggacccctg aggtcacatg cgtggtggtg gacgtgagcc acgaagaccc tgaggtcaag     180
ttcaactggt acgtggacgg cgtggaggtg cataatgcca agacaaagcc gcggaggag      240
cagtacaaca gcacgtaccg tgtggtcagc gtcctcaccg tcctgcacca ggactggctg     300
aatggcaagg agtacaagtg caaggtctcc aacaaagccc tcccagcccc catcgagaaa     360
accatctcca aagccaaagg cagccccga gaaccacagg tgtacaccct gcccccatcc     420
cgggataagc tgaccaagaa ccaggtccac ctgacctgcc tggtcaaagg cttctatccc     480
agcgacatcg ccgtggagtg ggagagcaat gggcagccgg agaacaacta caagaccacg     540
cctcccgtgc tgaagtccga cggctccttc gccctctaca gcaagctcac cgtggacaag     600
agcaggtggc agcaggggaa cgtcttctca tgctccgtga tgcatgaggc tctgcacaac     660
cactacacgc agaagagcct ctccctgtct ccgggtaaag gaggcggtgg atcagagaaa     720
ctgggaaaac ttcagtattc actggattat gatttccaaa ataaccagct gctggtaggg     780
atcattcagg ctgccgaact gccgccttg gacatggggg gcacatctga tccttacgtg     840
aaagtgtttc tgctacctga taagaagaag aaatttgaga caaaagtcca ccgaaaaacc     900
cttaatcctg tcttcaatga gcaatttact ttcaaggtac atactccgga attgggtggc     960
aaaacccctag tgatggctgt atatgatttt gatcgtttct ctaagcatga catcattgga    1020
```

-continued

```
gaatttaaag tccctatgaa cacagtggat tttggccatg taactgagga atggcgtgac    1080
ctgcaaagtg ct                                                        1092
```

<210> SEQ ID NO 14
<211> LENGTH: 364
<212> TYPE: PRT
<213> ORGANISM: Homo sapiens

<400> SEQUENCE: 14

| | | | | | | | | | | | |
|---|---|---|---|---|---|---|---|---|---|---|---|
| Val | Glu | Pro | Lys | Ser | Ser | Asp | Lys | Thr | His | Thr | Cys | Pro | Cys | Pro |
| 1 | | | | 5 | | | | | 10 | | | | | 15 |

Val Glu Pro Lys Ser Ser Asp Lys Thr His Thr Cys Pro Cys Pro
1               5                   10                  15

Ala Pro Glu Leu Leu Arg Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Arg Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Lys Leu
130                 135                 140

Thr Lys Asn Gln Val His Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Lys Ser Asp Gly Ser Phe Ala Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys Gly Gly Gly Ser Glu Lys
225                 230                 235                 240

Leu Gly Lys Leu Gln Tyr Ser Leu Asp Tyr Asp Phe Gln Asn Asn Gln
                245                 250                 255

Leu Leu Val Gly Ile Ile Gln Ala Ala Glu Leu Pro Ala Leu Asp Met
            260                 265                 270

Gly Gly Thr Ser Asp Pro Tyr Val Lys Val Phe Leu Leu Pro Asp Lys
        275                 280                 285

Lys Lys Lys Phe Glu Thr Lys Val His Arg Lys Thr Leu Asn Pro Val
290                 295                 300

Phe Asn Glu Gln Phe Thr Phe Lys Val Pro Tyr Ser Glu Leu Gly Gly
305                 310                 315                 320

Lys Thr Leu Val Met Ala Val Tyr Asp Phe Asp Arg Phe Ser Lys His
                325                 330                 335

Asp Ile Ile Gly Glu Phe Lys Val Pro Met Asn Thr Val Asp Phe Gly
            340                 345                 350

His Val Thr Glu Glu Trp Arg Asp Leu Gln Ser Ala
            355                 360

<210> SEQ ID NO 15
<211> LENGTH: 1704
<212> TYPE: DNA
<213> ORGANISM: Homo sapiens

<400> SEQUENCE: 15

| | | | | |
|---|---|---|---|---|
| gaggtgcagc | tggtgcagtc | cggcgccgag | gtgaagaagc | ccggcgcctc | cgtgaaggtg | 60 |
| tcctgcaagg | cctccggcta | caccttcacc | tcctactgga | tgcactgggt | gcggcaggcc | 120 |
| cccggccagg | gcctggagtg | gatcggcgag | atcaacccca | ccaacggccg | gaccaactac | 180 |
| atcgagaagt | tcaagtcccg | ggccaccctg | accgtggaca | agtccgcctc | caccgcctac | 240 |
| atggagctgt | cctccctgcg | gtccgaggac | accgccgtgt | actactgcgc | cggggccacc | 300 |
| cgggcctacc | actactgggg | ccagggcacc | atggtgaccg | tgtcctccgc | ctccaccaag | 360 |
| ggcccatcgg | tcttccccct | ggcaccctcc | tccaagagca | cctctggggg | cacagcggcc | 420 |
| ctgggctgcc | tggtcaagga | ctacttcccc | gaaccggtga | cggtgtcgtg | gaactcaggc | 480 |
| gccctgacca | gcggcgtgca | caccttcccg | gctgtcctac | agtcctcagg | actctactcc | 540 |
| ctcagcagcg | tggtgactgt | gccctccagc | agcttgggca | cccagaccta | catctgcaac | 600 |
| gtgaatcaca | agcccagcaa | caccaaggtg | gacaagaaag | ttgagcccaa | atcttgtgac | 660 |
| aaaactcaca | catgcccacc | gtgcccagca | cctgaactcc | tggggggacc | gtcagtcttc | 720 |
| ctcttccccc | caaaacccaa | ggacaccctc | atgatctccc | ggacccctga | ggtcacatgc | 780 |
| gtggtggtgg | acgtgagcca | cgaagaccct | gaggtcaagt | tcaactggta | cgtggacggc | 840 |
| gtggaggtgc | ataatgccaa | gacaaagccg | cgggaggagc | agtacaacag | cacgtaccgt | 900 |
| gtggtcagcg | tccttaccgt | cctgcaccag | gactggctga | atggcaagga | gtacaagtgc | 960 |
| aaggtctcca | acaaagccct | cccagccccc | atcgagaaaa | ccatctccaa | agccaaaggg | 1020 |
| cagccccgag | aaccacaggt | gaccaccctg | cccccatccc | gggatgagct | gaccaagaac | 1080 |
| caggtcagcc | tgacctgcct | ggtcaaaggc | ttctatccca | gcgacatcgc | cgtggagtgg | 1140 |
| gagagcaatg | ggcagccgga | gaacaactac | aagaccttcc | ctcccgtgct | ggactccgac | 1200 |
| ggctccttct | tcctctacag | caagctcacc | gtggacaaga | gcaggtggca | gcagggggaac | 1260 |
| gtcttctcat | gctccgtgat | gcatgaggct | ctgcacaacc | actacacgca | gaagagcctc | 1320 |
| tccctgtctc | cgggtaaagg | aggcggtgga | tcaggacaat | tcagagtgat | aggaccaggg | 1380 |
| tatcccatcc | gggctttagt | tggggatgaa | gcagagctgc | cgtgccgcat | ctctcctggg | 1440 |
| aaaaatgcca | cgggcatgga | ggtgggttgg | taccgttctc | ccttctcaag | agtggttcac | 1500 |
| ctctaccgaa | atggcaagga | ccaagatgca | gagcaagcac | tgaataccg | ggacgcaca | 1560 |
| gagcttctga | agagactat | cagtgaggga | aaggttaccc | ttaggattca | gaacgtgaga | 1620 |
| ttctcagatg | aaggaggcta | cacctgcttc | ttcagagacc | actcttacca | agaagaggca | 1680 |
| gcaatggagt | tgaaagtgga | agat | | | | 1704 |

<210> SEQ ID NO 16
<211> LENGTH: 568
<212> TYPE: PRT
<213> ORGANISM: Homo sapiens

<400> SEQUENCE: 16

Glu Val Gln Leu Val Gln Ser Gly Ala Glu Val Lys Lys Pro Gly Ala
1               5                   10                  15

-continued

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
            35                  40                  45

Gly Glu Ile Asn Pro Thr Asn Gly Arg Thr Asn Tyr Ile Glu Lys Phe
 50                  55                  60

Lys Ser Arg Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
            85                  90                  95

Ala Arg Gly Thr Arg Ala Tyr His Tyr Trp Gly Gln Gly Thr Met Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Phe Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Gly
            435                 440                 445

Gly Gly Ser Gly Gln Phe Arg Val Ile Gly Pro Gly Tyr Pro Ile Arg
450                 455                 460

Ala Leu Val Gly Asp Glu Ala Glu Leu Pro Cys Arg Ile Ser Pro Gly
465                 470                 475                 480

Lys Asn Ala Thr Gly Met Glu Val Gly Trp Tyr Arg Ser Pro Phe Ser
                485                 490                 495

Arg Val Val His Leu Tyr Arg Asn Gly Lys Asp Gln Asp Ala Glu Gln
                500                 505                 510

Ala Pro Glu Tyr Arg Gly Arg Thr Glu Leu Leu Lys Glu Thr Ile Ser
            515                 520                 525

Glu Gly Lys Val Thr Leu Arg Ile Gln Asn Val Arg Phe Ser Asp Glu
530                 535                 540

Gly Tyr Thr Cys Phe Phe Arg Asp His Ser Tyr Gln Glu Glu Ala
545                 550                 555                 560

Ala Met Glu Leu Lys Val Glu Asp
            565

<210> SEQ ID NO 17
<211> LENGTH: 1338
<212> TYPE: DNA
<213> ORGANISM: Homo sapiens

<400> SEQUENCE: 17
gaggtgcagc tggtgcagtc cggcgccgag gtgaagaagc ccggcgcctc cgtgaaggtg    60
tcctgcaagg cctccggcta caccttcacc tcctactgga tgcactgggt gcggcaggcc    120
cccggccagc ggctggagtg gatcggcgag atcaacccca ccaacggccg gaccaactac    180
atcgagaagt tcaagtcccg ggccaccctg accgtggaca gtccgcctc caccgcctac    240 atggagctgt cctccctgcg gtccgaggac accgccgtgt actactgcgc cggggcacc    300 cgggcctacc actactgggg ccagggcacc atggtgaccg tgtcctccgc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgactgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggatgagct gaccaagaac   1080 caggtcacc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttcg ccctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                  1338

<210> SEQ ID NO 18
<211> LENGTH: 446
<212> TYPE: PRT
<213> ORGANISM: Homo sapiens

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asn Pro Thr Asn Gly Arg Thr Asn Tyr Ile Glu Lys Phe
    50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val His Leu Thr Cys Leu Val
        355                 360                 365

Lys Gly Phe Tyr Pro Ser Asp Ile Ala Val Glu Trp Glu Ser Asn Gly
               370                 375                 380

Gln Pro Glu Asn Asn Tyr Lys Thr Thr Pro Pro Val Leu Asp Ser Asp
385                 390                 395                 400

Gly Ser Phe Ala Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 19
<211> LENGTH: 639
<212> TYPE: DNA
<213> ORGANISM: Homo sapiens

<400> SEQUENCE: 19

```
gacatccaga tgacccagtc cccctcctcc ctgtccgcct ccgtgggcga ccgggtgacc      60
atcacctgcc gggcctccga caacctgtac tccaacctgg cctggtacca gcagaagccc     120
ggcaagtccc ccaagctgct ggtgtacgac gccaccaacc tggccgacgg cgtgccctcc     180
cggttctccg gctccggctc cggcaccgac tacaccctga ccatctcctc cctgcagccc     240
gaggacttcg ccacctacta ctgccagcac ttctggggca ccccccctga cttcggccag     300
ggcaccaagg tggagatcaa gactgtggct gcaccatctg tcttcatctt cccgccatct     360
gatgagcagt tgaaatctgg aactgcctct gttgtgtgcc tgctgaataa cttctatccc     420
agagaggcca agtacagtgg aaggtggata acgccctcc aatcgggtaa ctcccaggag      480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agttcgcccg tcacaaagag cttcaacagg ggagagtgt                            639
```

<210> SEQ ID NO 20
<211> LENGTH: 213
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Leu Tyr Ser Asn
            20                  25                  30

Leu Ala Trp Tyr Gln Gln Lys Pro Gly Lys Ser Pro Lys Leu Leu Val
        35                  40                  45

Tyr Asp Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Leu
                85                  90                  95

Thr Phe Gly Gln Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 21
<211> LENGTH: 1704
<212> TYPE: DNA
<213> ORGANISM: Homo sapiens

<400> SEQUENCE: 21

```
gaggtgcagc tggtgcagtc cggcgccgag gtgaagaagc ccggcgcctc cgtgaaggtg    60
tcctgcaagg cctccggcta caccttcacc tcctactgga tgcactgggt gcggcaggcc   120
cccggccagc ggctggagtg gatcggcgag atcaaccccc caacggccg accaactac    180
atcgagaagt tcaagtcccg ggccaccctg accgtggaca gtccgcctc caccgcctac   240
atggagctgt cctccctgcg gtccgaggac accgccgtgt actactgcgc cggggcacc   300
cgggcctacc actactgggg ccagggcacc atggtgaccg tgtcctccgc ctccaccaag   360
ggcccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgactgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tgggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tccttaccgt cctgcaccag gactggctga atggcaagga gtacaagtgc   960
aaggtctcca acaaagcccg cccagccccc atcgagaaaa ccatctccaa agccaaaggg  1020
cagccccgag aaccacaggt gtaccaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccttcc tcccgtgct ggactccgac   1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaagg aggcggtgga tcaggacaat tcagagtgat aggaccaggg  1380
tatcccatcc gggctttagt tgggatgaa gcagagctgc cgtgccgcat ctctcctggg  1440
aaaaatgcca cgggcatgga ggtgggttgg taccgttctc ccttctcaag agtggttcac  1500
ctctaccgaa atggcaagga ccaagatgca gagcaagcac ctgaataccg gggacgcaca  1560
gagcttctga aagagactat cagtgaggga aaggttaccc ttaggattca gaacgtgaga  1620
ttctcagatg aaggaggcta cacctgcttc ttcagagacc actcttacca agaagaggca  1680
```
gcaatggagt tgaaagtgga agat 1704

<210> SEQ ID NO 22
<211> LENGTH: 568
<212> TYPE: PRT
<213> ORGANISM: Homo sapiens

<400> SEQUENCE: 22

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asn Pro Thr Asn Gly Arg Thr Asn Tyr Ile Glu Lys Phe
    50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Arg Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Arg Pro Ala Pro Ile Glu Lys Thr Ile Ser
                325                 330                 335

Lys Ala Lys Gly Gln Pro Arg Glu Pro Gln Val Thr Leu Pro Pro
            340                 345                 350

Ser Arg Asp Glu Leu Thr Lys Asn Gln Val Ser Leu Thr Cys Leu Val
        355                 360                 365

```
Lys Gly Phe Tyr Pro Ser Asp Ile Ala Val Glu Trp Glu Ser Asn Gly
            370                 375                 380

Gln Pro Glu Asn Asn Tyr Lys Thr Phe Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys Gly Gly
            435                 440                 445

Gly Gly Ser Gly Gln Phe Arg Val Ile Gly Pro Gly Tyr Pro Ile Arg
450                 455                 460

Ala Leu Val Gly Asp Glu Ala Glu Leu Pro Cys Arg Ile Ser Pro Gly
465                 470                 475                 480

Lys Asn Ala Thr Gly Met Glu Val Gly Trp Tyr Arg Ser Pro Phe Ser
                485                 490                 495

Arg Val Val His Leu Tyr Arg Asn Gly Lys Asp Gln Asp Ala Glu Gln
                500                 505                 510

Ala Pro Glu Tyr Arg Gly Arg Thr Glu Leu Leu Lys Glu Thr Ile Ser
            515                 520                 525

Glu Gly Lys Val Thr Leu Arg Ile Gln Asn Val Arg Phe Ser Asp Glu
530                 535                 540

Gly Gly Tyr Thr Cys Phe Phe Arg Asp His Ser Tyr Gln Glu Glu Ala
545                 550                 555                 560

Ala Met Glu Leu Lys Val Glu Asp
                565

<210> SEQ ID NO 23
<211> LENGTH: 1338
<212> TYPE: DNA
<213> ORGANISM: Homo sapiens

<400> SEQUENCE: 23
gaggtgcagc tggtgcagtc cggcgccgag gtgaagaagc ccggcgcctc cgtgaaggtg      60
tcctgcaagg cctccggcta caccttcacc tcctactgga tgcactgggt gcggcaggcc     120
cccggccagc ggctggagtg gatcggcgag atcaaccccc ccaacggccg gaccaactac     180
atcgagaagt tcaagtcccg ggccaccctg accgtggaca gtccgcctc accgcctac      240 atggagctgt cctccctgcg gtccgaggac accgccgtgt actactgcgc cggggcacc     300 cgggcctacc actactgggg ccagggcacc atggtgaccg tgtcctccgc ctccaccaag     360
ggcccatcgg tcttcccccc tggcaccctc ctccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgactgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tgggggacc gtcagtcttc     720 ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
```

-continued

```
aaggtctcca acaaagcccg cccagccccc atcgagaaaa ccatctccaa agccaaaggg    1020
cagccccgag aaccacaggt gtacaccctg cccccatccc gggatgagct gaccaagaac    1080
caggtccacc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttcg ccctctacag caagctcacc gtggacaaga gcaggtggca gcagggaac     1260 gtcttctcat gctccgtgat gcatgaggct ctgcacaacc actacacgca gaagagcctc    1320
tccctgtctc cgggtaaa                                                  1338
```

<210> SEQ ID NO 24
<211> LENGTH: 446
<212> TYPE: PRT
<213> ORGANISM: Homo sapiens

<400> SEQUENCE: 24

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Glu Ile Asn Pro Thr Asn Gly Arg Thr Asn Tyr Ile Glu Lys Phe
    50                  55                  60

Lys Ser Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Arg Ala Tyr His Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Arg Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

Leu Thr Val Leu His Gln Asp Trp Leu Asn Gly Lys Glu Tyr Lys Cys
305                 310                 315                 320

Lys Val Ser Asn Lys Ala Arg Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val His Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Ala Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 25
<211> LENGTH: 2601
<212> TYPE: DNA
<213> ORGANISM: Homo sapiens

<400> SEQUENCE: 25

```
acccaagtgt gcaccggcac agacatgaag ctgcggctcc ctgccagtcc cgagacccac      60
ctggacatgc tccgccacct ctaccagggc tgccaggtgg tgcagggaaa cctggaactc     120
acctacctgc ccaccaatgc cagcctgtcc ttcctgcagg atatccagga ggtgcagggc     180
tacgtgctca tcgctcacaa ccaagtgagg caggtcccac tgcagaggct gcggattgtg     240
cgaggcaccc agctctttga ggacaactat gccctggccg tgctagacaa tggagacccg     300
ctgaacaata ccaccccctgt cacaggggcc tccccaggag gcctgcggga gctgcagctt     360
cgaagcctca cagagatctt gaaaggaggg gtcttgatcc agcggaaccc ccagctctgc     420
taccaggaca cgattttgtg gaaggacatc ttccacaaga caaccagct ggctctcaca     480 ctgatagaca ccaaccgctc tcgggcctgc caccccctgtt ctccgatgtg taagggctcc     540
cgctgctggg gagagagttc tgaggattgt cagagcctga cgcgcactgt ctgtgccggt     600
ggctgtgccc gctgcaaggg gccactgccc actgactgct gccatgagca gtgtgctgcc     660
ggctgcacgg gccccaagca ctctgactgc ctggcctgcc tccacttcaa ccacagtggc     720
atctgtgagc tgcactgccc agccctggtc acctacaaca cagacacgtt tgagtccatg     780
cccaatcccg agggccggta cactattcggc gccagctgtg tgactgcctg tccctacaac     840 taccttttcta cggacgtggg atcctgcacc ctcgtctgcc ccctgcacaa ccagaggtg     900 acagcagagg atggaacaca gcggtgtgag aagtgcagca gccctgtgc ccgagtgtgc     960 tatggtctgg gcatggagca cttgcgagag gtgagggcag ttaccagtgc caatatccag    1020
gagtttgctg gctgcaagaa gatctttggg agcctggcat ttctgccgga gagctttgat    1080
ggggacccag cctccaacac tgccccgctc agccagagc agctccaagt gttttgagact    1140 ctggaagaga tcacaggtta cctatacatc tcagcatggc cggacagcct gcctgacctc    1200
agcgtcttcc agaacctgca gtaatccgg ggacgaattc tgcacaatgg cgcctactcg    1260 ctgacccctgc aagggctggg catcagctgg ctggggctgc gctcactgag ggaactgggc    1320
```

-continued

```
agtggactgg ccctcatcca ccataacacc cacctctgct tcgtgcacac ggtgccctgg      1380
gaccagctct ttcggaaccc gcaccaagct ctgctccaca ctgccaaccg gccagaggac      1440
gagtgtgtgg gcgagggcct ggcctgccac cagctgtgcg cccgagggca ctgctggggt      1500
ccagggccca cccagtgtgt caactgcagc cagttccttc ggggccagga gtgcgtggag      1560
gaatgccgag tactgcaggg gctccccagg gagtatgtga atgccaggca ctgtttgccg      1620
tgccaccctg agtgtcagcc ccagaatggc tcagtgacct gttttggacc ggaggctgac      1680
cagtgtgtgg cctgtgccca ctataaggac cctcccttct gcgtggcccg ctgccccagc      1740
ggtgtgaaac ctgacctctc ctacatgccc atctggaagt ttccagatga ggagggcgca      1800
tgccagcctt gccccatcaa ctgcacccac tcctgtgtgg acctggatga caagggctgc      1860
cccgccgagc agagagccag ccctctgacg attgaaggcc gcatggatcc caaatcttct      1920
gacaaaactc acacatgccc accgtgccca gcacctgaac tcctgggggg accgtcagtc      1980
ttcctcttcc ccccaaaacc caaggacacc ctctacatca ctcgggaacc tgaggtcaca      2040
tgcgtggtgg tggacgtgag ccacgaagac cctgaggtca agttcaactg gtacgtggac      2100
ggcgtggagg tgcataatgc caagacaaag ccgcgggagg agcagtacaa cagcacgtac      2160
cgtgtggtca gcgtcctcac cgtcctgcac caggactggc tgaatggcaa ggagtacaag      2220
tgcaaggtct ccaacaaagc cctcccagcc ccatcgaga aaaccatctc caaagccaaa      2280
gggcagcccc gagaaccaca ggtgaccacc ctgcccccat cccgggatga gctgaccaag      2340
aaccaggtca gcctgacctg cctggtcaaa ggcttctatc ccagcgacat cgccgtggag      2400
tgggagagca atgggcagcc ggagaacaac tacaagacct tccctcccgt gctggactcc      2460
gacggctcct tcttcctcta cagcaagctc accgtggaca agagcaggtg gcagcagggg      2520
aacgtcttct catgctctgt gatgcatgag gctctgaaat ccactacac gcagaagagc      2580 ctctcccctgt ctcctggtaa a                                              2601
```

<210> SEQ ID NO 26
<211> LENGTH: 867
<212> TYPE: PRT
<213> ORGANISM: Homo sapiens

<400> SEQUENCE: 26

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140
```

```
Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
            165                 170                 175

Cys Lys Gly Ser Arg Cys Trp Gly Glu Ser Ser Glu Asp Cys Gln Ser
        180                 185                 190

Leu Thr Arg Thr Val Cys Ala Gly Gly Cys Ala Arg Cys Lys Gly Pro
    195                 200                 205

Leu Pro Thr Asp Cys Cys His Glu Gln Cys Ala Ala Gly Cys Thr Gly
210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560
```

Gln Cys Val Ala Cys Ala His Tyr Lys Asp Pro Phe Cys Val Ala
            565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
            595                 600                 605

Thr His Ser Cys Val Asp Leu Asp Asp Lys Gly Cys Pro Ala Glu Gln
            610                 615                 620

Arg Ala Ser Pro Leu Thr Ile Glu Gly Arg Met Asp Pro Lys Ser Ser
625                 630                 635                 640

Asp Lys Thr His Thr Cys Pro Pro Cys Pro Ala Pro Glu Leu Leu Gly
            645                 650                 655

Gly Pro Ser Val Phe Leu Phe Pro Pro Lys Pro Lys Asp Thr Leu Tyr
            660                 665                 670

Ile Thr Arg Glu Pro Glu Val Thr Cys Val Val Val Asp Val Ser His
            675                 680                 685

Glu Asp Pro Glu Val Lys Phe Asn Trp Tyr Val Asp Gly Val Glu Val
            690                 695                 700

His Asn Ala Lys Thr Lys Pro Arg Glu Glu Gln Tyr Asn Ser Thr Tyr
705                 710                 715                 720

Arg Val Val Ser Val Leu Thr Val Leu His Gln Asp Trp Leu Asn Gly
            725                 730                 735

Lys Glu Tyr Lys Cys Lys Val Ser Asn Lys Ala Leu Pro Ala Pro Ile
            740                 745                 750

Glu Lys Thr Ile Ser Lys Ala Lys Gly Gln Pro Arg Glu Pro Gln Val
            755                 760                 765

Thr Thr Leu Pro Pro Ser Arg Asp Glu Leu Thr Lys Asn Gln Val Ser
770                 775                 780

Leu Thr Cys Leu Val Lys Gly Phe Tyr Pro Ser Asp Ile Ala Val Glu
785                 790                 795                 800

Trp Glu Ser Asn Gly Gln Pro Glu Asn Asn Tyr Lys Thr Phe Pro Pro
            805                 810                 815

Val Leu Asp Ser Asp Gly Ser Phe Phe Leu Tyr Ser Lys Leu Thr Val
            820                 825                 830

Asp Lys Ser Arg Trp Gln Gln Gly Asn Val Phe Ser Cys Ser Val Met
            835                 840                 845

His Glu Ala Leu Lys Phe His Tyr Thr Gln Lys Ser Leu Ser Leu Ser
            850                 855                 860

Pro Gly Lys
865

<210> SEQ ID NO 27
<211> LENGTH: 699
<212> TYPE: DNA
<213> ORGANISM: Homo sapiens

<400> SEQUENCE: 27
gttgagccca aatcttctga caaaactcac acatgcccac cgtgcccagc acctgaactc      60
ctggggggac cgtcagtctt cctcttcccc ccaaaaccca aggacaccct ctacatcact     120
cgggaacctg aggtcacatg cgtggtggtg gacgtgagcc acgaagaccc tgaggtcaag     180
ttcaactggt acgtggacgg cgtggaggtg cataatgcca agacaaagcc gcgggaggag     240
cagtacaaca gcacgtaccg tgtggtcagc gtcctcaccg tcctgcacca ggactggctg     300
aatggcaagg agtacaagtg caaggtctcc aacaaagccc tcccagcccc catcgagaaa     360

```
accatctcca aagccaaagg gcagccccga gaaccacagg tgtacaccct gcccccatcc      420
cgggatgagc tgaccaagaa ccaggtccac ctgacctgcc tggtcaaagg cttctatccc      480
agcgacatcg ccgtggagtg ggagagcaat gggcagccgg agaacaacta caagaccacg      540
cctcccgtgc tggactccga cggctccttc gccctctaca gcaagctcac cgtggacaag      600
agcaggtggc agcaggggaa cgtcttctca tgctccgtga tgcatgaggc tctgaaattc      660
cactacacgc agaagagcct ctccctgtct ccgggtaaa                             699
```

<210> SEQ ID NO 28
<211> LENGTH: 233
<212> TYPE: PRT
<213> ORGANISM: Homo sapiens

<400> SEQUENCE: 28

```
Val Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Tyr Ile Thr Arg Glu Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val His Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Ala Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu Lys Phe His Tyr Thr Gln
    210                 215                 220

Lys Ser Leu Ser Leu Ser Pro Gly Lys
225                 230
```

<210> SEQ ID NO 29
<211> LENGTH: 2835
<212> TYPE: DNA
<213> ORGANISM: Homo sapiens

<400> SEQUENCE: 29

```
gttgagccca atcttctga caaaactcac acatgcccac cgtgcccagc acctgaactc       60 ctgagggac cgtcagtctt cctcttcccc ccaaaaccca aggacaccct ctacatcact      120
cgggaacctg aggtcacatg cgtggtggtg gacgtgagcc acgaagaccc tgaggtcaag      180
```

```
ttcaactggt acgtggacgg cgtggaggtg cataatgcca agacaaagcc gcgggaggag    240
cagtacaaca gcacgtaccg tgtggtcagc gtcctcaccg tcctgcacca ggactggctg    300
aatggcaagg agtacaagtg caaggtctcc aacaaagccc gcccagcccc catcgagaaa    360
accatctcca aagccaaagg gcagccccga gaaccacagg tgaccaccct gcccccatcc    420
cgggatgagc tgaccaagaa ccaggtcagc ctgacctgcc tggtcaaagg cttctatccc    480
agcgacatcg ccgtggagtg ggagagcaat gggcagccgg agaacaacta caagaccttc    540
cctcccgtgc tggactccga cggctccttc ttcctctaca gcaagctcac cgtggacaag    600
agcaggtggc agcaggggaa cgtcttctca tgctctgtga tgcatgaggc tctgaaattc    660
cactacacgc agaagagcct ctccctgtct ccgggtaaag gaggcggtgg atcaaaatcc    720
tccaatgaag ctactaacat tactccaaag cataatatga aagcattttt ggatgaattg    780
aaagctgaga acatcaagaa gttcttatat aattttacac agataccaca tttagcagga    840
acagaacaaa actttcagct tgcaaagcaa attcaatccc agtggaaaga atttggcctg    900
gattctgttg agctagcaca ttatgatgtc ctgttgtcct acccaaataa gactcatccc    960
aactacatct caataattaa tgaagatgga atgagatttt caacacatc attatttgaa   1020 ccacctcctc caggatatga aaatgtttcg gatattgtac cacctttcag tgctttctct   1080
cctcaaggaa tgccagaggg cgatctagtg tatgttaact atgcacgaac tgaagacttc   1140
tttaaattgg aacgggacat gaaaatcaat tgctctggga aaattgtaat tgccagatat   1200
gggaaagttt tcagaggaaa taaggttaaa aatgcccagc tggcaggggc caaaggagtc   1260
attctctact ccgaccctgc tgactacttt gctcctgggg tgaagtccta tccagatggt   1320
tggaatcttc ctggaggtgg tgtccagcgt ggaaatatcc taaatctgaa tggtgcagga   1380
gaccctctca caccaggtta cccagcaaat gaatatgctt ataggcgtgg aattgcagag   1440
gctgttggtc ttccaagtat tcctgttcat ccaattggat actatgatgc acagaagctc   1500
ctagaaaaaa tgggtggctc agcaccacca gatagcagct ggagaggaag tctcaaagtg   1560
ccctacaatg ttggacctgg ctttactgga aacttttcta cacaaaaagt caagatgcac   1620
atccactcta ccaatgaagt gacaagaatt tacaatgtga taggtactct cagaggagca   1680
gtggaaccag acagatatgt cattctggga ggtcaccggg actcatgggt gtttggtggt   1740
attgaccctc agagtggagc agctgttgtt catgaaattg tgaggagctt tggaacactg   1800
aaaaaggaag ggtggagacc tagaagaaca attttgtttg caagctggga tgcagaagaa   1860
tttggtcttc ttggttctac tgagtgggca gaggagaatt caagactcct tcaagagcgt   1920
ggcgtggctt atattaatgc tgactcatct atagaaggaa actacactct gagagttgat   1980
tgtacaccgc tgatgtacag cttggtacac aacctaacaa aagagctgaa aagccctgat   2040
gaaggctttg aaggcaaatc tctttatgaa agttggacta aaaaaagtcc ttccccagag   2100
ttcagtggca tgcccaggat aagcaaattg ggatctggaa atgattttga ggtgttcttc   2160
caacgacttg gaattgcttc aggcagagca cggtatacta aaaattggga aacaaacaaa   2220
ttcagcggct atccactgta tcacagtgtc tatgaaacat atgagttggt ggaaaagttt   2280
tatgatccaa tgtttaaata tcacctcact gtggcccagg ttcgaggagg atggtgttt    2340 gagctagcca attccatagt gctccctttt gattgtcgag attatgctgt agttttaaga   2400
aagtatgctg acaaaatcta cagtatttct atgaaacatc cacaggaaat gaagacatac   2460
agtgtatcat ttgattcact ttttttctgca gtaaagaatt ttacagaaat tgcttccaag   2520
```

-continued

```
ttcagtgaga gactccagga ctttgacaaa agcaacccaa tagtattaag aatgatgaat    2580
gatcaactca tgtttctgga aagagcattt attgatccat tagggttacc agacaggcct    2640
ttttataggc atgtcatcta tgctccaagc agccacaaca agtatgcagg ggagtcattc    2700
ccaggaattt atgatgctct gtttgatatt gaaagcaaag tggacccttc caaggcctgg    2760
ggagaagtga agagacagat ttatgttgca gccttcacag tgcaggcagc tgcagagact    2820
ttgagtgaag tagcc                                                     2835
```

```
<210> SEQ ID NO 30
<211> LENGTH: 945
<212> TYPE: PRT
<213> ORGANISM: Homo sapiens

<400> SEQUENCE: 30
```

```
Val Glu Pro Lys Ser Ser Asp Lys Thr His Thr Cys Pro Pro Cys Pro
1               5                   10                  15

Ala Pro Glu Leu Leu Arg Gly Pro Ser Val Phe Leu Phe Pro Pro Lys
            20                  25                  30

Pro Lys Asp Thr Leu Tyr Ile Thr Arg Glu Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Arg Pro Ala Pro Ile Glu Lys Thr Ile Ser Lys Ala Lys Gly Gln
        115                 120                 125

Pro Arg Glu Pro Gln Val Thr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Phe Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu Lys Phe His Tyr Thr Gln
    210                 215                 220

Lys Ser Leu Ser Leu Ser Pro Gly Lys Gly Gly Gly Ser Lys Ser
225                 230                 235                 240

Ser Asn Glu Ala Thr Asn Ile Thr Pro Lys His Asn Met Lys Ala Phe
                245                 250                 255

Leu Asp Glu Leu Lys Ala Glu Asn Ile Lys Lys Phe Leu Tyr Asn Phe
            260                 265                 270

Thr Gln Ile Pro His Leu Ala Gly Thr Glu Gln Asn Phe Gln Leu Ala
        275                 280                 285

Lys Gln Ile Gln Ser Gln Trp Lys Glu Phe Gly Leu Asp Ser Val Glu
    290                 295                 300

Leu Ala His Tyr Asp Val Leu Leu Ser Tyr Pro Asn Lys Thr His Pro
305                 310                 315                 320
```

```
Asn Tyr Ile Ser Ile Ile Asn Glu Asp Gly Asn Glu Ile Phe Asn Thr
                325                 330                 335

Ser Leu Phe Glu Pro Pro Pro Gly Tyr Glu Asn Val Ser Asp Ile
            340                 345                 350

Val Pro Pro Phe Ser Ala Phe Ser Pro Gln Gly Met Pro Glu Gly Asp
        355                 360                 365

Leu Val Tyr Val Asn Tyr Ala Arg Thr Glu Asp Phe Phe Lys Leu Glu
    370                 375                 380

Arg Asp Met Lys Ile Asn Cys Ser Gly Lys Ile Val Ile Ala Arg Tyr
385                 390                 395                 400

Gly Lys Val Phe Arg Gly Asn Lys Val Lys Asn Ala Gln Leu Ala Gly
                405                 410                 415

Ala Lys Gly Val Ile Leu Tyr Ser Asp Pro Ala Asp Tyr Phe Ala Pro
            420                 425                 430

Gly Val Lys Ser Tyr Pro Asp Gly Trp Asn Leu Pro Gly Gly Gly Val
        435                 440                 445

Gln Arg Gly Asn Ile Leu Asn Leu Asn Gly Ala Gly Asp Pro Leu Thr
    450                 455                 460

Pro Gly Tyr Pro Ala Asn Glu Tyr Ala Tyr Arg Arg Gly Ile Ala Glu
465                 470                 475                 480

Ala Val Gly Leu Pro Ser Ile Pro Val His Pro Ile Gly Tyr Tyr Asp
                485                 490                 495

Ala Gln Lys Leu Leu Glu Lys Met Gly Gly Ser Ala Pro Pro Asp Ser
            500                 505                 510

Ser Trp Arg Gly Ser Leu Lys Val Pro Tyr Asn Val Gly Pro Gly Phe
        515                 520                 525

Thr Gly Asn Phe Ser Thr Gln Lys Val Lys Met His Ile His Ser Thr
    530                 535                 540

Asn Glu Val Thr Arg Ile Tyr Asn Val Ile Gly Thr Leu Arg Gly Ala
545                 550                 555                 560

Val Glu Pro Asp Arg Tyr Val Ile Leu Gly Gly His Arg Asp Ser Trp
                565                 570                 575

Val Phe Gly Gly Ile Asp Pro Gln Ser Gly Ala Ala Val Val His Glu
            580                 585                 590

Ile Val Arg Ser Phe Gly Thr Leu Lys Lys Glu Gly Trp Arg Pro Arg
        595                 600                 605

Arg Thr Ile Leu Phe Ala Ser Trp Asp Ala Glu Glu Phe Gly Leu Leu
    610                 615                 620

Gly Ser Thr Glu Trp Ala Glu Glu Asn Ser Arg Leu Leu Gln Glu Arg
625                 630                 635                 640

Gly Val Ala Tyr Ile Asn Ala Asp Ser Ser Ile Glu Gly Asn Tyr Thr
                645                 650                 655

Leu Arg Val Asp Cys Thr Pro Leu Met Tyr Ser Leu Val His Asn Leu
            660                 665                 670

Thr Lys Glu Leu Lys Ser Pro Asp Glu Gly Phe Glu Gly Lys Ser Leu
        675                 680                 685

Tyr Glu Ser Trp Thr Lys Lys Ser Pro Ser Pro Glu Phe Ser Gly Met
    690                 695                 700

Pro Arg Ile Ser Lys Leu Gly Ser Gly Asn Asp Phe Glu Val Phe Phe
705                 710                 715                 720

Gln Arg Leu Gly Ile Ala Ser Gly Arg Ala Arg Tyr Thr Lys Asn Trp
                725                 730                 735
```

| | | | | | | | | | | | |
|---|---|---|---|---|---|---|---|---|---|---|---|
| Glu | Thr | Asn | Lys | Phe | Ser | Gly | Tyr | Pro | Leu | Tyr | His | Ser | Val | Tyr | Glu |
| | | | 740 | | | | | 745 | | | | | 750 | | |

Glu Thr Asn Lys Phe Ser Gly Tyr Pro Leu Tyr His Ser Val Tyr Glu
             740                  745                   750

Thr Tyr Glu Leu Val Glu Lys Phe Tyr Asp Pro Met Phe Lys Tyr His
         755                     760                  765

Leu Thr Val Ala Gln Val Arg Gly Gly Met Val Phe Glu Leu Ala Asn
    770                   775                  780

Ser Ile Val Leu Pro Phe Asp Cys Arg Asp Tyr Ala Val Val Leu Arg
785             790                  795              800

Lys Tyr Ala Asp Lys Ile Tyr Ser Ile Ser Met Lys His Pro Gln Glu
             805                  810              815

Met Lys Thr Tyr Ser Val Ser Phe Asp Ser Leu Phe Ser Ala Val Lys
    820                   825                  830

Asn Phe Thr Glu Ile Ala Ser Lys Phe Ser Glu Arg Leu Gln Asp Phe
         835                     840                  845

Asp Lys Ser Asn Pro Ile Val Leu Arg Met Met Asn Asp Gln Leu Met
850             855                  860

Phe Leu Glu Arg Ala Phe Ile Asp Pro Leu Gly Leu Pro Asp Arg Pro
865             870                  875              880

Phe Tyr Arg His Val Ile Tyr Ala Pro Ser Ser His Asn Lys Tyr Ala
         885                     890                  895

Gly Glu Ser Phe Pro Gly Ile Tyr Asp Ala Leu Phe Asp Ile Glu Ser
             900                  905              910

Lys Val Asp Pro Ser Lys Ala Trp Gly Glu Val Lys Arg Gln Ile Tyr
         915                     920                  925

Val Ala Ala Phe Thr Val Gln Ala Ala Ala Glu Thr Leu Ser Glu Val
    930                   935                  940

Ala
945

<210> SEQ ID NO 31
<211> LENGTH: 2469
<212> TYPE: DNA
<213> ORGANISM: Homo sapiens

<400> SEQUENCE: 31

```
atggcatctc cgggctctgg cttttggtct ttcgggtcgg aagatggctc tggggattcc      60
gagaatcccg gcacagcgcg agcctggtgc caagtggctc agaagttcac gggcggcatc     120
ggaaacaaac tgtgcgccct gctctacgga gacgccgaga gccggcggga gagcggcggg     180
agccaacccc gcgggccgc cgcccggaag gccgcctgcg cctgcgacca gaagccctgc     240
agctgctcca agtggatgt caactacgcg tttctccatg caacagacct gctgccggcg     300
tgtgatggag aaaggcccac tttggcgttt ctgcaagatg ttatgaacat tttacttcag     360
tatgtggtga aaagtttcga tagatcaacc aaagtgattg atttccatta tcctaatgag     420
cttctccaag aatataattg ggaattggca gaccaaccac aaaatttgga ggaaattttg     480
atgcattgcc aaacaactct aaaatatgca attaaaacag gcatcctag atacttcaat     540 caactttcta ctggtttgga tatggttgga ttagcagcag actggctgac atcaacagca     600
aatactaaca tgttcaccta tgaaattgct ccagtatttg tgcttttgga atatgtcaca     660
ctaaagaaaa tgagagaaat cattggctgg ccagggggct ctggcgatgg gatattttct     720
cccggtggcg ccatatctaa catgtatgcc atgatgatcg cacgctttaa gatgttccca     780
gaagtcaagg agaaaggaat ggctgctctt cccaggctca ttgccttcac gtctgaacat     840
agtcattttt ctctcaagaa gggagctgca gccttaggga ttggaacaga cagcgtgatt     900
```

```
ctgattaaat gtgatgagag agggaaaatg attccatctg atcttgaaag aaggattctt    960
gaagccaaac agaaagggtt tgttcctttc ctcgtgagtg ccacagctgg aaccaccgtg   1020
tacggagcat ttgaccccct cttagctgtc gctgacattt gcaaaaagta agatctgg    1080 atgcatgtgg atgcagcttg gggtggggga ttactgatgt cccgaaaaca caagtggaaa   1140
ctgagtggcg tggagagggc caactctgtg acgtggaatc cacacaagat gatgggagtc   1200
cctttgcagt gctctgctct cctggttaga aagagggat tgatgcagaa ttgcaaccaa    1260
atgcatgcct cctacctctt tcagcaagat aaacattatg acctgtccta tgacactgga   1320
gacaaggcct acagtgcgg acgccacgtt gatgttttta actatggct gatgtggagg     1380 gcaaagggga ctaccgggtt tgaagcgcat gttgataaat gtttggagtt ggcagagtat   1440
ttatacaaca tcataaaaaa ccgagaagga tatgagatgg tgtttgatgg aagcctcag    1500 cacacaaatg tctgcttctg gtacattcct ccaagcttgc gtactctgga agacaatgaa   1560
gagagaatga gtcgcctctc gaaggtggct ccagtgatta agccagaat gatggagtat    1620 ggaaccacaa tggtcagcta ccaacccttg ggagacaagg tcaatttctt ccgcatggtc   1680
atctcaaacc cagcggcaac tcaccaagac attgacttcc tgattgaaga aatagaacgc   1740
cttggacaag atttaggagg cggtggatca gttgagccca atcttctga caaaactcac    1800 acatgcccac cgtgcccagc acctgaactc ctgggggac cgtcagtctt cctcttcccc    1860
ccaaaaccca aggacaccct ctacatcact cgggaacctg aggtcacatg cgtggtggtg   1920
gacgtgagcc acgaagaccc tgaggtcaag ttcaactggt acgtggacgg cgtggaggtg   1980
cataatgcca agacaaagcc gcgggaggag cagtacaaca gcacgtaccg tgtggtcagc   2040
gtcctcaccg tcctgcacca ggactggctg aatggcaagg agtacaagtg caaggtctcc   2100
aacaaagccc gcccagcccc catcgagaaa accatctcca aagccaaagg gcagccccga   2160
gaaccacagg tgaccaccct gcccccatcc cgggatgagc tgaccaagaa ccaggtcagc   2220
ctgacctgcc tggtcaaagg cttctatccc agcgacatcg ccgtggagtg ggagagcaat   2280
gggcagccgg agaacaacta caagaccttc cctcccgtgc tggactccga cggctccttc   2340
ttcctctaca gcaagctcac cgtggacaag agcaggtggc agcaggggaa cgtcttctca   2400
tgctctgtga tgcatgaggc tctgaaattc cactacacgc agaagagcct ctccctgtct   2460
ccgggtaaa                                                          2469
```

<210> SEQ ID NO 32
<211> LENGTH: 823
<212> TYPE: PRT
<213> ORGANISM: Homo sapiens

<400> SEQUENCE: 32

```
Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
```

```
                    85                  90                  95
Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
            115                 120                 125

Ser Thr Lys Val Ile Asp Phe His Tyr Pro Asn Glu Leu Leu Gln Glu
            130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
                180                 185                 190

Ala Asp Trp Leu Thr Ser Thr Ala Asn Thr Asn Met Phe Thr Tyr Glu
            195                 200                 205

Ile Ala Pro Val Phe Val Leu Leu Glu Tyr Val Thr Leu Lys Lys Met
            210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
            275                 280                 285

Ala Ala Ala Leu Gly Ile Gly Thr Asp Ser Val Ile Leu Ile Lys Cys
            290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
                340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
            370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
            435                 440                 445

His Val Asp Val Phe Lys Leu Trp Leu Met Trp Arg Ala Lys Gly Thr
            450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510
```

```
Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
    530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu Gly Gly Gly Ser Val Glu
            580                 585                 590

Pro Lys Ser Ser Asp Lys Thr His Thr Cys Pro Pro Cys Pro Ala Pro
        595                 600                 605

Glu Leu Leu Arg Gly Pro Ser Val Phe Leu Phe Pro Pro Lys Pro Lys
        610                 615                 620

Asp Thr Leu Tyr Ile Thr Arg Glu Pro Glu Val Thr Cys Val Val Val
625                 630                 635                 640

Asp Val Ser His Glu Asp Pro Glu Val Lys Phe Asn Trp Tyr Val Asp
                645                 650                 655

Gly Val Glu Val His Asn Ala Lys Thr Lys Pro Arg Glu Glu Gln Tyr
            660                 665                 670

Asn Ser Thr Tyr Arg Val Val Ser Val Leu Thr Val Leu His Gln Asp
        675                 680                 685

Trp Leu Asn Gly Lys Glu Tyr Lys Cys Lys Val Ser Asn Lys Ala Arg
        690                 695                 700

Pro Ala Pro Ile Glu Lys Thr Ile Ser Lys Ala Lys Gly Gln Pro Arg
705                 710                 715                 720

Glu Pro Gln Val Thr Thr Leu Pro Pro Ser Arg Asp Glu Leu Thr Lys
                725                 730                 735

Asn Gln Val Ser Leu Thr Cys Leu Val Lys Gly Phe Tyr Pro Ser Asp
            740                 745                 750

Ile Ala Val Glu Trp Glu Ser Asn Gly Gln Pro Glu Asn Asn Tyr Lys
        755                 760                 765

Thr Phe Pro Pro Val Leu Asp Ser Asp Gly Ser Phe Phe Leu Tyr Ser
    770                 775                 780

Lys Leu Thr Val Asp Lys Ser Arg Trp Gln Gln Gly Asn Val Phe Ser
785                 790                 795                 800

Cys Ser Val Met His Glu Ala Leu Lys Phe His Tyr Thr Gln Lys Ser
                805                 810                 815

Leu Ser Leu Ser Pro Gly Lys
            820

<210> SEQ ID NO 33
<211> LENGTH: 1683
<212> TYPE: DNA
<213> ORGANISM: Homo sapiens

<400> SEQUENCE: 33
atgagtgaca gacccacagc aaggcggtgg ggtaagtgtg gacctttgtg taccagagag      60
aacatcatgg tggcttttcaa aggggtctgg actcaagctt tctggaaagc agtcacagcg    120
gaatttctgg ccatgcttat ttttgttctc ctcagcctgg atccaccat caactggggt      180 ggaacagaaa agcctttacc ggtcgacatg gttctcatct cccttttgctt tggactcagc   240 attgcaacca tggtgcagtg ctttggccat atcagcggtg ccacatcaa ccctgcagtg    300
```

```
actgtggcca tggtgtgcac caggaagatc agcatcgcca agtctgtctt ctacatcgca    360
gcccagtgcc tgggggccat cattggagca ggaatcctct atctggtcac acctcccagt    420
gtggtgggag gcctgggagt caccatggtt catggaaatc ttaccgctgg tcatggtctc    480
ctggttgagt tgataatcac atttcaattg gtgtttacta tctttgccag ctgtgattcc    540
aaacggactg atgtcactgg ctcaatagct ttagcaattg gattttctgt tgcaattgga    600
catttatttg caatcaatta tactggtgcc agcatgaatc ccgcccgatc ctttggacct    660
gcagttatca tgggaaattg ggaaaaccat tggatatatt gggttgggcc catcatagga    720
gctgtcctcg ctggtggcct ttatgagtat gtcttctgtc cagatgttga attcaaacgt    780
cgttttaaag aagccttcag caaagctgcc cagcaaacaa aggaagcta catggaggtg      840
gaggacaaca ggagtcaggt agagacggat gacctgattc taaaacctgg agtggtgcat    900
gtgattgacg ttgaccgggg agaggagaag aaggggaaag accaatctgg agaggtattg    960
tcttcagtag gaggcggtgg atcagttgag cccaaatctt ctgacaaaac tcacacatgc   1020
ccaccgtgcc cagcacctga actcctgagg ggaccgtcag tcttcctctt cccccaaaa    1080
cccaaggaca cctctacat cactcgggaa cctgaggtca catgcgtggt ggtggacgtg    1140
agccacgaag accctgaggt caagttcaac tggtacgtgg acggcgtgga ggtgcataat   1200
gccaagacaa agccgcggga ggagcagtac aacagcacgt accgtgtggt cagcgtcctc   1260
accgtcctgc accaggactg gctgaatggc aaggagtaca agtgcaaggt ctccaacaaa   1320
gcccgcccag cccccatcga gaaaaccatc tccaaagcca agggcagcc ccgagaacca    1380
caggtgacca ccctgccccc atcccgggat gagctgacca gaaccaggt cagcctgacc     1440
tgcctggtca aaggcttcta tcccagcgac atcgccgtgg agtgggagag caatgggcag   1500
ccggagaaca actacaagac cttccctccc gtgctggact ccgacggctc cttcttcctc   1560
tacagcaagc tcaccgtgga caagagcagg tggcagcagg ggaacgtctt ctcatgctct   1620
gtgatgcatg aggctctgaa attccactac acgcagaaga gcctctccct gtctccgggt   1680
aaa                                                                  1683
```

<210> SEQ ID NO 34
<211> LENGTH: 561
<212> TYPE: PRT
<213> ORGANISM: Homo sapiens

<400> SEQUENCE: 34

```
Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45

Val Leu Leu Ser Leu Gly Ser Thr Ile Asn Trp Gly Gly Thr Glu Lys
    50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
            100                 105                 110

Ala Lys Ser Val Phe Tyr Ile Ala Ala Gln Cys Leu Gly Ala Ile Ile
        115                 120                 125
```

```
Gly Ala Gly Ile Leu Tyr Leu Val Thr Pro Ser Val Gly Gly
130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
                180                 185                 190

Ile Gly Phe Ser Val Ala Ile Gly His Leu Phe Ala Ile Asn Tyr Thr
                195                 200                 205

Gly Ala Ser Met Asn Pro Ala Arg Ser Phe Gly Pro Ala Val Ile Met
210                 215                 220

Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
                245                 250                 255

Glu Phe Lys Arg Arg Phe Lys Glu Ala Phe Ser Lys Ala Ala Gln Gln
                260                 265                 270

Thr Lys Gly Ser Tyr Met Glu Val Glu Asp Asn Arg Ser Gln Val Glu
                275                 280                 285

Thr Asp Asp Leu Ile Leu Lys Pro Gly Val Val His Val Ile Asp Val
290                 295                 300

Asp Arg Gly Glu Glu Lys Lys Gly Lys Asp Gln Ser Gly Glu Val Leu
305                 310                 315                 320

Ser Ser Val Gly Gly Gly Ser Val Glu Pro Lys Ser Ser Asp Lys
                325                 330                 335

Thr His Thr Cys Pro Pro Cys Pro Ala Pro Glu Leu Leu Arg Gly Pro
                340                 345                 350

Ser Val Phe Leu Phe Pro Pro Lys Pro Lys Asp Thr Leu Tyr Ile Thr
                355                 360                 365

Arg Glu Pro Glu Val Thr Cys Val Val Val Asp Val Ser His Glu Asp
                370                 375                 380

Pro Glu Val Lys Phe Asn Trp Tyr Val Asp Gly Val Glu Val His Asn
385                 390                 395                 400

Ala Lys Thr Lys Pro Arg Glu Glu Gln Tyr Asn Ser Thr Tyr Arg Val
                405                 410                 415

Val Ser Val Leu Thr Val Leu His Gln Asp Trp Leu Asn Gly Lys Glu
                420                 425                 430

Tyr Lys Cys Lys Val Ser Asn Lys Ala Arg Pro Ala Pro Ile Glu Lys
                435                 440                 445

Thr Ile Ser Lys Ala Lys Gly Gln Pro Arg Glu Pro Gln Val Thr Thr
450                 455                 460

Leu Pro Pro Ser Arg Asp Glu Leu Thr Lys Asn Gln Val Ser Leu Thr
465                 470                 475                 480

Cys Leu Val Lys Gly Phe Tyr Pro Ser Asp Ile Ala Val Glu Trp Glu
                485                 490                 495

Ser Asn Gly Gln Pro Glu Asn Asn Tyr Lys Thr Phe Pro Pro Val Leu
                500                 505                 510

Asp Ser Asp Gly Ser Phe Phe Leu Tyr Ser Lys Leu Thr Val Asp Lys
                515                 520                 525

Ser Arg Trp Gln Gln Gly Asn Val Phe Ser Cys Ser Val Met His Glu
530                 535                 540
```

```
Ala Leu Lys Phe His Tyr Thr Gln Lys Ser Leu Ser Leu Ser Pro Gly
545                 550                 555                 560

Lys

<210> SEQ ID NO 35
<211> LENGTH: 11
<212> TYPE: PRT
<213> ORGANISM: Artificial Sequence
<220> FEATURE:
<223> OTHER INFORMATION: protein sequence - artificial

<400> SEQUENCE: 35

Gly Ser Ser Gly Gly Ser Gly Gly Gly Gly Ser
1               5                   10

<210> SEQ ID NO 36
<211> LENGTH: 15
<212> TYPE: PRT
<213> ORGANISM: Artificial Sequence
<220> FEATURE:
<223> OTHER INFORMATION: protein sequence - artificial

<400> SEQUENCE: 36

Gly Gly Gly Gly Ser Gly Gly Gly Gly Ser Gly Gly Gly Gly Ser
1               5                   10                  15

<210> SEQ ID NO 37
<211> LENGTH: 6
<212> TYPE: PRT
<213> ORGANISM: Artificial Sequence
<220> FEATURE:
<223> OTHER INFORMATION: protein sequence - artificial

<400> SEQUENCE: 37

Ile Glu Gly Arg Met Asp
1               5

<210> SEQ ID NO 38
<211> LENGTH: 5
<212> TYPE: PRT
<213> ORGANISM: Artificial Sequence
<220> FEATURE:
<223> OTHER INFORMATION: protein sequence - artificial

<400> SEQUENCE: 38

Gly Gly Gly Gly Ser
1               5
```